United States Patent
Holzer et al.

(10) Patent No.: US 11,424,007 B2
(45) Date of Patent: Aug. 23, 2022

(54) SELECTION AND MONITORING METHODS FOR XENOTRANSPLANTATION

(71) Applicants: XENOTHERAPEUTICS, INC., Boston, MA (US); ALEXIS BIO, INC., Grantham, NH (US)

(72) Inventors: Paul Holzer, Enfield, NH (US); Rodney L. Monroy, North Fort Myers, FL (US); Andrey Ptitsyn, Revere, MA (US); Elizabeth Chang, Pittsford, NY (US); Jon Adkins, Londonderry, NH (US); Travis Brown, Columbia, MO (US); Kaitlyn Rogers, Madisonville, LA (US)

(73) Assignees: XENOTHERAPEUTICS, INC., Boston, MA (US); ALEXIS BIO, INC., Grantham, NH (US)

( * ) Notice: Subject to any disclaimer, the term of this patent is extended or adjusted under 35 U.S.C. 154(b) by 0 days.

(21) Appl. No.: 17/337,786

(22) Filed: Jun. 3, 2021

(65) Prior Publication Data
US 2021/0383892 A1    Dec. 9, 2021

Related U.S. Application Data

(60) Provisional application No. 63/034,140, filed on Jun. 3, 2020.

(51) Int. Cl.
| | |
|---|---|
| G06G 7/48 | (2006.01) |
| G16B 35/20 | (2019.01) |
| G16B 5/20 | (2019.01) |
| G16B 40/00 | (2019.01) |
| C12N 15/10 | (2006.01) |
| G16H 50/20 | (2018.01) |
| G16H 70/60 | (2018.01) |
| G16H 10/60 | (2018.01) |
| G16H 10/40 | (2018.01) |
| G06N 20/00 | (2019.01) |
| G16H 50/70 | (2018.01) |
| G16H 20/10 | (2018.01) |

(52) U.S. Cl.
CPC .......... *G16B 35/20* (2019.02); *C12N 15/1089* (2013.01); *G06N 20/00* (2019.01); *G16B 5/20* (2019.02); *G16B 40/00* (2019.02); *G16H 10/40* (2018.01); *G16H 10/60* (2018.01); *G16H 50/20* (2018.01); *G16H 50/70* (2018.01); *G16H 70/60* (2018.01); *G16H 20/10* (2018.01)

(58) Field of Classification Search
None
See application file for complete search history.

(56) References Cited

U.S. PATENT DOCUMENTS

| | | | |
|---|---|---|---|
| 8,370,072 B2 | 2/2013 | Fernandez | |
| 9,561,006 B2 | 2/2017 | Elster et al. | |
| 10,336,998 B2 | 7/2019 | Serber et al. | |
| 2016/0208280 A1 | 7/2016 | Fire et al. | |
| 2019/0311781 A1* | 10/2019 | Stratford | G16B 40/00 |
| 2019/0346829 A1 | 11/2019 | Flitsch et al. | |
| 2020/0279616 A1* | 9/2020 | Rooney | A61P 35/00 |

FOREIGN PATENT DOCUMENTS

| | | |
|---|---|---|
| WO | 2014110590 A1 | 7/2014 |
| WO | 2019169042 A1 | 9/2019 |
| WO | 2020118452 A1 | 6/2020 |

OTHER PUBLICATIONS

Choi, Yoonjoo, et al. "Antibody humanization by structure-based computational protein design." MAbs. vol. 7. No. 6. Taylor & Francis, 2015.*
Volk et al. "Biosystems Design by Machine Learning" (ACS Synth. Biol. 2020 vol. 9 pp. 1514-1533).*
Dawson, H. D. et. al., "The porcine translational research database: a manually curated, genomics and proteomics-based research resource", BMC Genomics, 10.1186/s12864-017-4009-7, 2017, 13 pages.
Saini, S.K. et al., "SARS-CoV-2 genome-wide T cell epitope mapping reveals immunodominance and substantial CD8+ T cell activation in COVID-19 patients", Sci. Immunol. 10.1126/sciimmunol.abf7550, 2021, 23 pages.

(Continued)

*Primary Examiner* — Anna Skibinsky
(74) *Attorney, Agent, or Firm* — Rothwell, Figg, Ernst & Manbeck, P.C.

(57) ABSTRACT

A method for predictive engineering of a sample derived from a genetically optimized non-human donor suitable for xenotransplantation into a human having improved quality or performance is provided. The method includes constructing a training data set from a series of libraries, wherein at least one library in the series of libraries comprises genomic, proteomic, and research data specific to non-humans. The method includes developing a predictive machine learning model based on the constructed training data set. The method includes utilizing the predictive machine learning model to obtain a predicted quality or performance of a plurality of sequences for a candidate sample from the non-human donor specific to a human patient or patient population. The method includes selecting a subset of sequences for evaluation from the plurality of sequences based on the predicted quality or performance. The method includes designing candidate samples derived from the non-human donor using the selected subset of sequences. The method includes measuring a respective in silico performance of each designed candidate sample. The method includes selecting a designed candidate sample for manufacture based on the respective in silico performance of each designed candidate sample.

28 Claims, 13 Drawing Sheets

Specification includes a Sequence Listing.

(56) References Cited

OTHER PUBLICATIONS

Sanchez-Trincado, J. et. al., "Fundamentals and Methods for T- and B-Cell Epitope Prediction", Hindawi, Journal of Immunology Research. vol. 2017, 15 pages.
Chen, B. et. al., "Predicting HLA class II antigen presentation through integrated deep learning" Nature Biotechnology, vol. 37, Nov. 2019, 1332-1343.
Lythe, G. et. al., "How Many TCR Clonotypes Does a Body Maintain?", Journal of Theoretical Biology, Jan. 21, 2016, 214-224.
Sanchez-Mazas A. et. al., "Common and well-documented (CWD) HLA alleles over all of Europe and within European sub-regions:a catalogue from the European Federation for Immunogenetics (EFI)", 2017, doi:10.1111/tan.12956, 21 pages.
Sakharkar, M. et. al., "Distributions of Exons and Intrans in the Human Genome", In Silico Biology 4 IOS Press, 2004, 387-393.
De Cassia Salvadori, L. et. al., "Frequency of alleles and haplotypes of the human leukocyte antigen system in Bauru, São Paulo, Brazil", Brazilian Journal of Hematology and Hemotherapy, vol. 36, No. 2, 2013, 108-114.
Maiers, M. et.al., "High-resolution HLA alleles and haplotypes in the United States population", Human Immunology, 2007, 779-788.
Nicosia, M. et. al., "Memory T Cells in Transplantation: Old Challenges Define New Directions", Transplantation, vol. 104, No. 10, 2020, 2024-2034
Kelley, D. R., "Cross-species regulatory sequence activity prediction", PLOS Computational Biology, vol. 16, No. 7, 2020, 27 pages.
Liang, C. et. al., "Structure and Aggregation Mechanism ofb2-Microglobulin (83-99)Peptides Studied by Molecular Dynamics Simulations", Biophysics Journal, vol. 93, 2007, 3353-3362.
Luscombe, N. M. et. al., "Amino acid-base interactions: a three-dimensionalanalysis of protein—DNA interactions at an atomic level", Nucleic Acids Research, vol. 29, No. 13, 2001, 2860-2874.
Lazaro, A. et. al., "Human Leukocyte Antigen (HLA) Typing by DNA Sequencing", Transplantation Immunology: Methods and Protocols, Second Edition, Methods in Molecular Biology, vol. 1034, 2013, 161-195.
Lin, S. et. al., "Stable-isotope-labeled Histone Peptide Libraryfor Histone Post-translational Modification andVariant Quantification by Mass Spectrometry", Technological Innovation and Resources, Molecular & Cellular Proteomics 13.9, 2014, 2450-2466.
Lee, H. et. al., "Bystander CD4+T cells: crossroads between innateand adaptive immunity", Experimental & Molecular Medicine, vol. 52, 2020, 1255-1263.
Gray, B. P. et. al., "Combinatorial Peptide Libraries: Mining for Cell-Binding Peptides", Chem Rev, vol. 114, No. 2, 2014, 1020-1081.
Fleri, W. et. al., "The Immune Epitope Database and Analysis Resource in Epitope Discovery and Synthetic Vaccine Design", Frontiers in Immunology, vol. 8, No. 278, 2017, 16 pages.
Klitz, W. et. al., "New HLA haplotype frequency reference standards: High-resolution and large sample typing of HLA DR-DQ haplotypes in a sample of European Americans", Tissue Antigens, vol. 62, 2003, 296-307.
Kirijas, M. et. al., "HLA profile of the donors in the Macedonian Bone Marrow Donor Registry", Wiley International Journal of Immunogenetics, 2018, 337-346.
Jawdat, D. et. al., "HLA-A, B, C, DRB1 and DQB1 allele and haplotype frequencies in volunteer bone marrow donors from Eastern Region of Saudi Arabia", Wiley Immune Response Genetics, HLA, vol. 94, 2019, 49-56.
Kelley, J. et. al., "IRIS: A database surveying known human immune system genes", Genomics 85, 2005, 503-511.
Guéry, J. C. et. al., "Constitutive presentation of dominant epitopes from endogenous naturally processed self-beta 2-microglobulin to call II-restricted T cells leads to self-tolerance", The Journal of Immunology 154, 1995, 545-554.
Hundrieser, J. et. al., "Role of human and porcine MHC DRB1 alleles in determining the intensity of individual human anti-pig T-cell responses", Xenotransplantation, 2019, 13 pages.

Golubovskaya, V. et. al., "Different Subsets of T Cells, Memory, effector Functions, and CAR-T Immunotherapy", Cancers, vol. 8, No. 36, 2016, 12 pages.
Gragert, L. et. al., "Six-locus high resolution HLA haplotype frequencies derived from mixed-resolution DNA typing for the entire US donor registry", Human Immunology 74, 2013, 1313-1320.
Farber, D. et. al., "Human memory T cells: generation, compartmentalization and homeostasis", Nat Rev Immunol., vol. 14, No. 1, 2014, 24-35.
Sachdeva, S. et. al., "A Rational Approach for Creating peptides Mimicking Antibody Binding", Scientific Reports, vol. 9 , No. 997, 2019, 11 pages.
Shen, W.-J. et. al., "The Utility of Supertype Clustering in Prediction for Class II MHC-Peptide Binding", Molecules, vol. 23, No. 3034, 2018, 18 pages.
Cole, D. et. al., "Modification of MHC Anchor Residues Generates Heteroclitic Peptides That Alter TCR Binding and T Cell Recognition", The Journal of Immunology, 2010, 2600-2610.
Bondinas, G. et. al., "The spectrum of HLA-DQ and HLA-DR alleles, 2006:a listing correlating sequence and structure with function", Immunogenetics 59, 2007, 539-553.
Filippone, E. J. et. al., "The implications of B-lineage Cells in Kidney Allografts", Transplantation, vol. 104, No. 10, 2020, 2011-2023.
Esmaeili, A. et. al., "Frequencies of HLA-A, B and DRB1 alleles in a large normal population living in the city of Mashhad, Northeastern Iran", Iranian Journal of Basic Medical Sciences, vol. 20, No. 8, 2017, 940-943.
De Greef, P. C. et. al., "The naive T-cell receptor repertoire has an extremely broad distribution of clone sizes", eLife, 2020, 24 pages.
Dewolf, S. et. al., "Alloimmune T cells in transplantation", The Journal of Clinical Investigation, vol. 127, No. 7, 2017, 2473-2481.
Poyet, M. et. al., "A Library of Human Gut Bacterial Isolates Paired with Longitudinal Multiomics Data Enables Mechanistic Microbiome Research", Nature Medicine, vol. 25, 2019, 1442-1452.
Chardon, P. et. al., "Sequence of the swine major histocompatibility complex region containing all non-classical class genes", Tissue Antigens, vol. 57, 2001, 55-65.
Betts, M. J. et. al., "Amino Acid Properties and Consequences of Substitutions", Bioinformatics for Geneticists, 2003, 289-316.
Burroughs, N. J. et. al., "Discriminating self from nonself with short peptides from large proteomes", Immunogenetics, vol. 56, 2004, 311-320.
Carey, K. et. al., "Frequency of off-targeting in genome edited pigs produced via direct, injection of the CRISPR/Cas9 system into developing embryos", BMC Biotechnology 19:25, 2019, 8 pages.
Budowle, B. et. al., "Subtyping of the HLA-DQA1 Locus and Independence Testingwith PM and STR/VNTR Loci", Journal of Forensic Sciences, 1998, 657-660.
Alter, I. et. al., "HLA class I haplotype diversityis consistent with selection for frequent existing haplotypes", PLOS Computational Biology, vol. 13, No. 8, 2017, 19 pages.
Basith, S. et. al., "Machine intelligence in peptide therapeutics: Anext-generation tool for rapid disease screening", Med Res Rev. 40, 2020, 1276-1314.
Aminikhah, M. et. al., "HLA Class I and Class II Genes Distribution of the Sistanis in Iran", Iran J of Immunology, vol. 15, No. 2, 2018, 97-111.
Ajay, S. S. et. al., "Accurate and comprehensive sequencing of personal genomes", Genome Research, 2011, 1498-1505.
Warren, R. L. et. al., "Exhaustive T-cell repertoire sequencing of human peripheral blood samples reveals signatures of antigen selection and a directly measured repertoire size of at least 1 million clonotypes", Genome Research, vol. 21, 2011, 790-797.
Stickler, M. et. al., "An In Vitro Human Cell-Based Assay to Rank the Relative Immunogenicity of Proteins", Toxicological Sciences, vol. 77, 2004, 280-289.
Stickler, M. et. al., "Human population-based identification of CD4+ T-cell peptide epitope determinants", Journal of Immunological Methods, vol. 281, 2003, 95-108.

(56) References Cited

OTHER PUBLICATIONS

Tshabalala, M. et. al., "Human Leukocyte Antigen-A, B, C, DRB1, and DQB1 Allele and Haplotype Frequencies in a Subset of 237Donors in the South African Bone Marrow Registry", Journal of Immunology Research, 2018, 8 pages.

Southwood, S. et. al., "Several Common HLA-DR Types Share Largely Overlapping Peptide Binding Repertoires", The Journal of Immunology, vol. 160, 1998, 3363-3373.

Trachtenberg, E. et. al., "HLA class I (A, B, C) and class II (DRB1, DQA1, DQB1, DPB1)alleles and haplotypes in the Han from southern China", Tissue Antigens, vol. 70, 2007, 455-463.

* cited by examiner

SELECTION AND MONITORING METHODS FOR XENOTRANSPLANTATION

CROSS REFERENCE TO RELATED APPLICATIONS

This application claims the benefit of U.S. Provisional Application No. 63/034,140 filed Jun. 3, 2020, the disclosure of which is incorporated herein in its entirety by reference.

INCORPORATION BY REFERENCE OF SEQUENCE LISTING

The present application includes a Sequence Listing filed in electronic format. The Sequence Listing is entitled "4772-109US2_ST25.txt" created on Jul. 7, 2021, and is 3,000 bytes in size. The information in the electronic format of the Sequence Listing is part of the present application and is incorporated herein by reference in its entirety.

TECHNICAL FIELD

The subject matter disclosed herein relates to utilizing artificial intelligence and machine learning in connection with donor selection, monitoring, and desired outcomes with respect to immunogenomic reprogramming of organs for xenotransplantation. The subject matter disclosed herein further relates to utilizing artificial intelligence and machine learning in xenotransplantation for the purpose of donor selection, genome engineering, graft monitoring, prediction of desired outcomes with respect to immunogenomic reprogramming of organs for xenotransplantation.

BACKGROUND

The major histocompatibility complex (MHC) is a set of genes that encodes proteins found on the surface of cells, which helps the immune system recognize foreign substances. The MHC determines histocompatibility, thereby controlling a major part of the immune system in vertebrates. There are two major types of MHC protein molecules—Class I and Class II. Class I protein molecules span the membrane of almost every cell in an organism, while Class II molecules are restricted to cells of the immune system, e.g., antigen-presenting cells such as dendritic cells, mononuclear phagocytes, some endothelial cells, thymic epithelial cells, B cells, macrophages, and lymphocytes. Each gene has a large number of alleles, i.e., alternate forms of a gene that produce alternate forms of the protein. Accordingly, it is very rare for two individuals to have the same set of MHC protein molecules.

MHC molecules allow T lymphocytes to detect cells, e.g. macrophages, which have ingested infectious microorganisms. MHC molecules bind to antigens derived from pathogens and display them on the cell surface for recognition by the appropriate T-cells. An immune response is stimulated when the T lymphocyte recognizes the foreign fragment attached to the MHC molecule and binds to it. Certain MHC molecules may be capable of binding to approximately 10,000 different peptides. In healthy and non-infected cells, the MHC molecule presents peptides from its own cell, to which T cells do not normally react.

Major histocompatibility complex Class I (MHCI) and Class II (MHCII) molecules display peptides on antigen-presenting cell surfaces for subsequent T-cell recognition. Within the human population, allelic variation among the classical MHCI and II gene products is the basis for differential peptide binding, thymic repertoire bias, and allograft rejection. MHC molecules are cell-surface glycoproteins that are central to the process of adaptive immunity, functioning to capture and display peptides on the surface of antigen-presenting cells (APCs). MHC Class I (MHCI) molecules are expressed on most cells, bind endogenously derived peptides with sizes ranging from eight to ten amino acid residues and are recognized by CD8 cytotoxic T-lymphocytes (CTL). On the other hand, MHC Class II (MHCII) peptides are present only on specialized APCs, bind exogenously derived peptides with sizes varying from 9 to 22 residues, and are recognized by CD4 helper T-cells. These differences indicate that MHCI and MHCII molecules engage two distinct arms of the T-cell-mediated immune response, the former targeting invasive pathogens such as viruses for destruction by CD8 CTLs, and the latter inducing cytokine-based inflammatory mediators to stimulate CD4 helper T-cell activities including B-cell activation, maturation, and antibody production.

In human beings, the MHC is called the human leukocyte antigen (HLA) system. The HLA segment is divided into three regions (from centromere to telomere), Class II, Class III, and Class I. Classical Class I and Class II HLA genes are contained in Class I and Class II regions, respectively, whereas the Class III locus bears genes encoding proteins involved in the immune system but not structurally related to MHC molecules. The classical HLA Class I molecules are of three types, HLA-A, HLA-B, and HLA-C. Only the $\alpha$ chains of these mature HLA Class I molecules are encoded within the Class I HLA locus by the respective HLA-A, HLA-B, and HLA-C genes. In contrast, the beta-2 microglobulin $\beta 2m$ chain encoded by the $\beta 2m$ gene is located on chromosome 15. The classical HLA Class II molecules are also of three types (HLA-DP, HLA-DQ, and HLA-DR), with both the $\alpha$ and $\beta$ chains of each encoded by a pair of adjacent loci. In addition to these classical HLA Class I and HLA Class II genes, the human MHC locus includes a long array of HLA pseudogenes as well as genes encoding non-classical MHCI and MHCII molecules. HLA-pseudogenes are an indication that gene duplication is the main driving force for HLA evolution, whereas non-classical MHCI and MHCII molecules often serve a restricted function within the immune system quite distinct from that of antigen presentation to $\alpha\beta$ TCRs. The HLA genes range from highly polymorphic, polymorphic, oligomorphic, and monomorphic, with genes on the polymorphic end having hundreds of allotypes. Each human cell expresses six MHC class I alleles (one HLA-A, -B, and -C allele from each parent) and six to eight MHC class II alleles (one HLA-DP and -DQ, and one or two HLA-DR from each parent, and combinations of these). Any two individuals who are not identical twins will express differing MHC molecules.

HLAs corresponding to MHC Class I (A, B, and C) which all are the HLA Class 1 group present peptides from inside the cell. For example, if the cell is infected by a virus, the HLA system brings fragments of the virus to the surface of the cell so that the cell can be destroyed by the immune system. These peptides are produced from digested proteins that are broken down in the proteasomes. In general, these particular peptides are small polymers, about 9 amino acids in length. Foreign antigens presented by MHC Class I attract killer T-cells (also called CD8 positive- or cytotoxic T-cells) that destroy cells. Foreign antigens presented by MHC Class I interact with CD8 positive-cytotoxic T-cells that destroy cells expressing this antigen. MHC Class I proteins are associated with β2-microglobulin, which unlike the HLA proteins is encoded by a gene on chromosome 15.

In addition to major genes A, B, and C, Class I includes minor genes E, G, and F (aka Class Ib genes). These genes are less polymorphic than HLA A, B, and C, but play an important role as regulators of the immune response. The Class Ib molecules function as ligands for immunomodulatory cell surface receptors expressed by the subsets of cells involved in graft rejection. HLA E can inhibit the cytotoxic function of both CD8+ T-cells and Natural Killer (NK) lymphocytes. HLA G and HLA F can promote graft tolerance by binding to Ig-like receptors of NK cells. Higher expression of HLA G and HLA F leads to higher levels of corresponding peptides on the cell surface which promotes graft tolerance without immunosuppression.1

HLAs corresponding to MHC Class II (DP, DM, DO, DQ, and DR) present antigens from outside of the cell to T-lymphocytes. These particular antigens stimulate the multiplication of T-helper cells (also called CD4 positive T cells), which in turn stimulate antibody-producing B-cells to produce antibodies to that specific antigen. Self-antigens are suppressed by regulatory T cells. The affected genes are known to encode 4 distinct regulatory factors controlling transcription of MHC Class II genes. These transacting factors are the Class II transactivator and 3 subunits of regulatory factor X (RFX): RFX containing ankyrin repeats (RFXANK), the fifth member of the RFX family (RFX5), and RFX-associated protein (RFXAP). Mutations in one of each define 4 distinct complementation groups termed A, B, C, and D, respectively.

HLAs corresponding to MHC Class III encode components of the complement system. HLAs have other roles. They are important in disease defense. They are the major cause of organ transplant rejections. They may protect against or fail to protect (if down-regulated by an infection) against cancers. Mutations in HLA may be linked to autoimmune disease (examples: type I diabetes, coeliac disease). HLA may also be related to people's perception of the odor of other people and may be involved in mate selection, as at least one study found a lower-than-expected rate of HLA similarity between spouses in an isolated community.

Aside from the genes encoding the 6 major antigen-presenting proteins, there are a large number of other genes, many involved in immune function, located on the HLA complex. Diversity of HLAs in the human population is one aspect of disease defense, and, as a result, the chance of two unrelated individuals with identical HLA molecules on all loci is extremely low. HLA genes have historically been identified as a result of the ability to successfully transplant organs between HLA-similar individuals.

In swine, the MHC is called the swine leukocyte antigen (SLA). In the pig (Sus scrofa) genome SLA maps to chromosome 7 where it is divided by the centromere. It consists of three regions: the class I and class III regions mapping to 7p1.1 and the class II region mapping to 7q1.1. The SLA complex spans between 2.4 and 2.7 Mb, depending on haplotype, and encodes approximately 150 loci, with at least 120 functional genes. Swine have long been considered a potential non-human source of organs, tissues, and/or cells for use in human xenotransplantation given that their size and physiology are compatible with humans. Porcine SLAs may include, but are not limited to, antigens encoded by the SLA-1, SLA-2, SLA-3, SLA-4, SLA-5, SLA-6, SLA-8, SLA-9, SLA-11 and SLA-12 loci. Porcine Class II SLAs include antigens encoded by the SLA-DQ and SLA-DR loci.

In organ, tissue, and stem cell transplantation, one challenge in successful transplantation is to find a host and a donor with tissue types as similar as possible. Accordingly, in organ, tissue, and stem cell transplantation, the key to success is finding a host and a donor with tissue types as similar as possible. Histocompatibility, or tissue compatibility, is the property of having the same or sufficiently similar alleles of the MHC such that the recipient's MHC does not trigger the immune system to reject the donor's tissue.

In transplantation, MHC molecules act themselves as antigens, provoking an immune response from a recipient, leading to transplant rejection. Accordingly, eliminating the expression of specific MHC molecules from the donor will serve to reduce immunological rejection of transplanted swine cells, tissues, and/or organs, into a human recipient. However, complete elimination of MHC molecules may also result in rejection due to innate immune response. Human MHC Class I and II are also called human leukocyte antigen (HLA). For the donor animals to survive and thrive, it is necessary to retain certain MHC molecules (e.g., SLAs) that provide the donor animals with a minimally competent immune system. Prior art strategies that rely on the deletion of the MHC gene pose significant risks to the donor animals, e.g., severe combined immune deficiency (SCID). Prior art strategies that do not reprogram the swine genome pose significant risks of rejection to the human recipient or require significant and endless use of immunosuppressants.

Because MHC variation in the human population is very high, it has been difficult or impossible to obtain cells, tissue, or organs for xenotransplantation that express MHC molecules sufficiently identical to the recipient for safe and effective transplantation of organs and tissues. Further, diversity and amino acid variations in non-MHC molecules between human and swine are a cause of immunological rejection of wild-type porcine cells. The immunoreactivity of xenograft may vary with natural variations of MHC in the donor population. On the other hand, natural variation in human MHC also modulates the intensity of immune response.

As alluded to, identification and improvements can be time-consuming and inefficient. The process by its very nature is haphazard and relies upon one stumbling upon an idea, therapeutic, or a body of knowledge that can be combined to have a desirable outcome on the cell, tissue, or organ therapy. Lastly, until only recently, the type and precision of the available gene-modification techniques were insufficient, cost-prohibitive, or did not exist to implement necessary, complex designs that may span multiple genes and chromosomes.

Not only are traditional methods of improvement inefficient, but this process can also lead to dangerous errors in judgment and unsafe medications. These detrimental outcomes and the accumulation of mutations and other mistakes can become significant and may lead to an eventual stagnation in the rate of performance improvement.

Thus, there is a great need in the art for new methods of designing, engineering, and manufacturing cell, tissue, or organ therapies which do not suffer from the aforementioned drawbacks inherent with traditional drug discovery processes and that will greatly accelerate the process of discovering and consolidating the beneficial understanding from bodies of knowledge that is ever-growing.

Further, there is an urgent need for a method by which to rehabilitate or correct current cell, tissue, or organ therapies that are currently employed that need improvements in therapeutic outcomes and enhanced safety.

Current approaches are subject to many limitations that are circumvented using the methods of the present disclosure. For example, traditional recombinant approaches as described above are slow and rely on a relatively small number of random recombination crossover events to introduce mutations and are therefore limited in the number of combinations that can be attempted in any given cycle or time period. In addition, although current natural recombination events are essentially random, they are also subject to positional bias. Most importantly the traditional approaches provide little information about the influence of individual genetic alterations and due to the random distribution of genetic alterations, many specific combinations cannot be generated or evaluated.

SUMMARY OF THE INVENTION

To overcome many of the aforementioned problems associated with the traditional programs, the present disclosure sets forth a unique high throughput genomic engineering platform that is computationally driven and integrates molecular biology automation data analytics and machine learning protocols. This integrated platform utilizes a suite of high throughput molecular toolsets that are used to construct high throughput genetic alteration libraries. These genetic alteration libraries are elaborated upon below.

The high throughput platform and its unique genomic alteration libraries fundamentally shift the paradigm of cell, tissue, or organ therapy development in evolution. For example, traditional mutagenesis-based methods of developing an industrial therapy design candidate sequence will eventually lead to cell, tissue, or organ therapies burdened with a heavy mutagenic load that has been accumulated over years of random mutations, insertions, deletions, and other polymorphisms.

The ability to solve this issue (e.g., identifying and engineering candidate sequences suitable for xenotransplantation) has eluded cell, tissue, or organ therapy researchers for decades. However, utilizing the high throughput platform disclosed herein these design candidate sequences can be rehabilitated and the deleterious mutations can be identified and removed. Concurrently, the genetic mutations that are identified as beneficial can be kept and, in some cases approved upon. The resulting therapy design candidate demonstrates superior phenotypic traits (i.e. improved production of a compound of interest), as compared to their parental sequences.

Furthermore, the high throughput platform taught herein can identify, characterize, and quantify the effect that individual mutation has on cell, tissue, or organ therapy performance. This information, e.g., what effect does a given genetic change X have on host cell phenotype Y (e.g. production of a compound of interest), can generate and then be stored in the cell, tissue, or organ therapy genetic alteration library discussed below. That is, sequence information for each genetic alteration and its effect on the host cell phenotype are stored in one or more databases and are available for subsequent analysis including epistasis (e.g., the interaction of genes that are not alleles, in particular the suppression of the effect of one such gene by another) mapping as discussed below. The present disclosure also teaches methods of physically saving and storing valuable genetic alterations in the form of genetic insertion constructs, or in the form of one or more host cell organisms containing said genetic alterations.

Optimization of cell, tissue, or organ therapies is an important and difficult problem with broad implications for the economy, society, medicine, science, and the natural world. Traditionally, such engineering has been performed through a slow and uncertain process of random alterations.

Such approaches leverage the natural evolutionary capacity of cells to adapt to artificially imposed selection pressure. Such approaches are also limited by the rarity of beneficial mutations, the ruggedness of the underlying fitness landscape, and more generally underutilized the state of the art in cellular and molecular biology.

Modern approaches leverage the new understanding of cellular function at the mechanistic level and new molecular biology tools to perform targeted genetic alterations to specific phenotypic ends. In practice, such rational approaches are confounded by the underlying complexity of biology.

Causal mechanisms are poorly understood particularly when attempting to combine two or more changes that each have an observed beneficial effect. Sometimes such consolidations of genetic alterations yield positive outcomes (measured by increases in desired phenotypic activity), although the net positive outcome may be lower than expected, and in some cases higher than expected. In other instances, such combinations either produce net neutral effect or a net negative effect. This phenomenon is referred to as epistasis and is one of the fundamental challenges to organism-level genomic engineering and genetic engineering in general.

As aforementioned, the present engineering platform solves many of the problems associated with traditional engineering approaches. The present platform uses automation technologies to perform hundreds or thousands of genetic mutations at once. In particular aspects, unlike the rational approaches described above, the disclosed platform enables parallel construction of thousands of mutations to more effectively explore large subsets of the relevant genomic space. By trying "everything" the present platform sidesteps the difficulties induced by our limited biological understanding.

However, at the same time the present platform faces the problem of being fundamentally limited by the combinatorial explosive size of genomic space, the vast array of knowledge available today, and the effectiveness of computational techniques to interpret the generated datasets given the complexity of genetic interactions. Techniques are needed to explore subsets of vast, combinatorial spaces and knowledge in ways that maximize non-random selection of combinations that yield desired outcomes.

The precise configuration is determined by the collective electromagnetic interactions between its constituent atomic components. This combination of short genomic sequence and physically constrained folding problem lends itself specifically to greedy optimization strategies. That is, it is possible to individually mutate the sequence at every residue and shuffle the resulting mutants to effectively sample local sequence space at a resolution compatible with the sequence Activity Response Modeling.

However, for full genomic optimizations for biomolecules and cell, tissue, or organ therapies, such residue-centric approaches are insufficient for some important reasons. First, because of the exponential increase in relevant sequence space associated with genomic optimization. Second, because of the added complexity of regulation, expression, and metabolic interactions in the biomolecule synthesis. The present inventors have solved these problems via the taught sequence prediction techniques disclosed herein.

Accordingly, there is a need for modeling epistatic interactions between a collection of mutations for more efficient and effective consolidation of said mutations into one or more genetic backgrounds.

When describing the epistasis mapping procedure, the terms "more efficient" and "more effective" refer to the avoidance of undesirable epistatic interactions among consolidated design candidate sequences with respect to particular phenotypic objectives.

The present disclosure provides a high throughput genomic engineering platform that does not suffer from the myriad of problems associated with traditional genetic alteration improvement programs. Further, the platform taught herein is able to rehabilitate a cell, tissue, or organ therapy that has accumulated non-beneficial genetic alterations through decades of random mutagenesis and enhanced phenotypic performance measures programs.

The present disclosure provides a genomic engineering platform that is computationally driven and integrates molecular biology automation advanced machine learning protocols. This integrated platform utilizes a suite of high throughput molecular tools and tool sets to create genetic alteration libraries that are derived from, inter alia, scientific insight, and iterative pattern recognition.

The high throughput genetic alteration libraries function as drivers of the genomic engineering process by providing libraries of particular genomic alterations for testing in a cell, tissue, or organ therapy. The cell, tissue, or organ therapy engineered utilizing a particular library or combination of libraries is efficiently screened in a high throughput manner for a resultant outcome, i.e., production of a cell, tissue, or organ therapy.

The process of utilizing high throughput genetic alteration libraries to define particular genomic alterations for testing in a cell, tissue, or organ therapy, and then subsequently screening a cell, tissue, or organ for those alterations, is implemented in an efficient and iterative manner.

Iterative cycle or "rounds" of genomic engineering campaigns can be at least 1, 2, 3, 4, 5, 6, 7, 8, 9, 10, 20, 30, 40, 50, 60, 70, 80, 90, 100, or more iterations.

Thus, the present disclosure teaches methods of conducting at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more "rounds" of high throughput genetic engineering.

In some embodiments, the present disclosure teaches a linear approach in which each subsequent high throughput engineering round is based on genetic variation identified in the previous round of genetic engineering in other embodiments. The present disclosure teaches a nonlinear approach in which subsequent high throughput genetic engineering rounds are based on genetic variation identified in any previous round of genetic engineering including previously conducted analysis and separate high throughput genetic engineering branches.

The data from these iterative cycles enable large-scale data analytics and pattern recognition which is utilized by the integrative platform to inform subsequent rounds of high throughput genetic alteration library implementation. The genetic alteration libraries utilized in the taught platform are highly dynamic tools that benefit from large-scale data and pattern recognition algorithms and become more informative through each iteration of engineering.

In some embodiments, the present disclosure provides illustrative examples and text describing the application of high throughput strain improvement methods to a cell, tissue, or organ therapy.

According to one aspect, a method for predictive engineering of a sample derived from a genetically optimized non-human donor suitable for xenotransplantation into a human having improved quality or performance is provided. The method includes constructing a training data set from a series of libraries, wherein at least one library in the series of libraries comprises genomic, proteomic, and research data specific to non-humans. The method includes developing a predictive machine learning model based on the constructed training data set. The method includes utilizing the predictive machine learning model to obtain a predicted quality or performance of a plurality of sequences for a candidate sample from the non-human donor specific to a human patient or patient population. The method includes selecting a subset of sequences for evaluation from the plurality of sequences based on the predicted quality or performance. The method includes designing candidate samples derived from the non-human donor using the selected subset of sequences. The method includes measuring a respective in silico performance of each designed candidate sample. The method includes selecting a designed candidate sample for manufacture based on the respective in silico performance of each designed candidate sample. According to another aspect, a computer program product is provided that is configured to perform the method. According to yet another aspect, a system comprising a processor and a non-transitory computer-readable memory coupled to the processor is provided, and the processor is configured to perform the method.

BRIEF DESCRIPTION OF THE DRAWINGS

The accompanying drawings, which are incorporated herein and form part of the specification, illustrate various embodiments.

DETAILED DESCRIPTION

Figure 1:
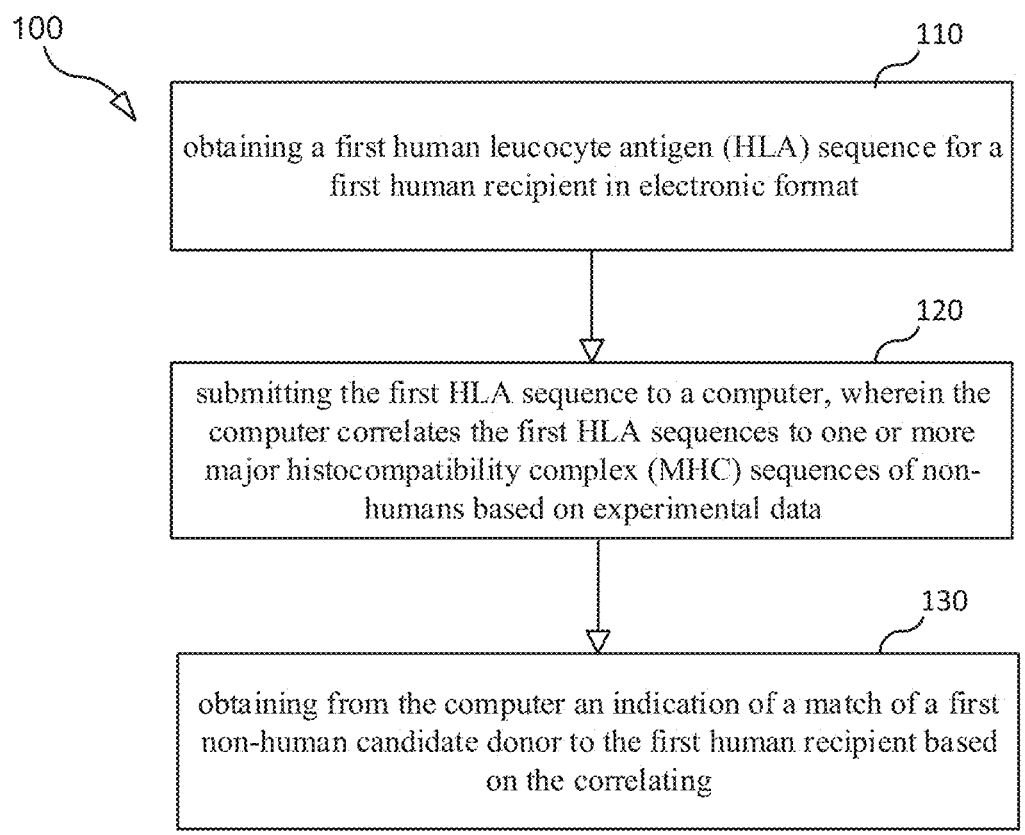
FIG. 1 illustrates an exemplary flow chart according to some embodiments.

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or aspects so described.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. Other features and advantages of the invention will be apparent from the following detailed description and figures, and the claims.

"Alter," "altering," "altered" and grammatical equivalents as used herein include any and/or all modifications to a gene including, but not limited to, deleting, inserting, silencing, modifying, reprogramming, disrupting, mutating, rearranging, increasing expression, knocking-in, knocking out, and/or any or all other such modifications or any combination thereof.

"Best alignment" or "optimum alignment" means the alignment for which the identity percentage determined as described below is the highest. Comparisons of sequences between two nucleic acid sequences are traditionally made by comparing these sequences after aligning them optimally, the said comparison being made by segment or by "comparison window" to identify and compare local regions for similar sequences. For the comparison, sequences may be optimally aligned manually, or by using alignment software, e.g., Smith and Waterman local homology algorithm (1981), the Needleman and Wunsch local homology algorithm (1970), the Pearson and Lipman similarity search method (1988), and computer software using these algorithms (GAP, BESTFIT, BLAST P, BLAST N, FASTA and TFASTA in the Wisconsin Genetics Software Package, Genetics Computer Group, 575 Science Dr., Madison, Wis.). In some aspects, the optimum alignment is obtained using the BLAST program with the BLOSUM 62 matrix or software having similar functionality. The "identity percentage" between two sequences of nucleic acids or amino acids is determined by comparing these two optimally aligned sequences, the sequence of nucleic acids or amino acids to be compared possibly including additions or deletions from the reference sequence for optimal alignment between these two sequences. The identity percentage is calculated by determining the number of positions for which the nucleotide or the amino acid residue is identical between the two sequences, by dividing this number of identical positions by the total number of compared positions and multiplying the result obtained by 100 to obtain the identity percentage between these two sequences.

"Capture sequence" or "reference sequence" and their grammatical equivalents as used herein include a nucleic acid or amino acid sequence that has been obtained, sequenced or otherwise become known from a sample, animal (including humans), or population. For example, a capture sequence from a human patient is a "human patient capture sequence." A capture sequence from a particular human population is a "human population-specific human capture sequence." And a capture sequence from a human allele group is an "allele-group-specific human capture sequence."

"Conservative," and its grammatical equivalents as used herein include a conservative amino acid substitution, including the substitution of an amino acid residue by another amino acid residue having a side chain R group with similar chemical properties (e.g., charge or hydrophobicity). Conservative amino acid substitutions may be achieved by modifying a nucleotide sequence to introduce a nucleotide change that will encode the conservative substitution. In general, a conservative amino acid substitution will not substantially change the functional properties of interest of a protein, for example, the ability of MHC I to present a peptide of interest. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. One skilled in the art would understand that in addition to the nucleic acid residues encoding a human or humanized MHC I polypeptide and/or β2 microglobulin described herein, due to the degeneracy of the genetic code, other nucleic acid sequences may encode the polypeptide(s) disclosed herein. Therefore, in addition to a genetically modified non-human animal that comprises in its genome a nucleotide sequence encoding MHC I and/or β2 microglobulin polypeptide(s) with conservative amino acid substitutions, a non-human animal whose genome comprises a nucleotide sequence(s) that differs from that described herein due to the degeneracy of the genetic code is also provided.

"Conserved" and its grammatical equivalents as used herein include nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. Herein, two or more sequences are said to be "completely conserved" if they are 100% identical to one another. In some embodiments, two or more sequences are said to be "highly conserved" if they are at least 70% identical, at least 80% identical, at least 90% identical, or at least 95% identical, but less than 100% identical, to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical, but less than 100% identical, to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

"Designated pathogen free" and its grammatical equivalents as used herein include reference to animals, animal herds, animal products derived therefrom, and/or animal facilities that are free of one or more specified pathogens. Preferably, such "designated pathogen free" animals, animal herds, animal products derived therefrom, and/or animal facilities are maintained using well-defined routines of testing for such designated pathogens, utilizing proper standard operating procedures (SOPs) and practices of herd husbandry and veterinary care to assure the absence and/or destruction of such designated pathogens, including routines, testing, procedures, husbandry, and veterinary care disclosed and described herein. It will be further understood that as used herein the term "free," and like terms when used in connection with "pathogen free" are meant to indicate that the subject pathogens are not present, not alive, not active, or otherwise not detectable by standard or other testing methods for the subject pathogens. Pathogens can also include, but not be limited to, emerging infectious diseases that have newly appeared in a population or have existed but are rapidly increasing in incidence or geographic range, or that are caused by one of the United States National Institute of Allergy and Infectious Diseases (NIAID) Category A, B, or C priority pathogens.

"Endogenous loci" and its grammatical equivalents as used herein include the natural genetic loci found in the animal to be transformed into the donor animal.

"Functional," e.g., in reference to a functional polypeptide, and its grammatical equivalents as used herein include a polypeptide that retains at least one biological activity normally associated with the native protein. For example, in some embodiments, a replacement at an endogenous locus (e.g., replacement at an endogenous non-human MHC I, MHC II, and/or β2 microglobulin locus) results in a locus that fails to express a functional endogenous polypeptide. Likewise, the term "functional" as used herein in reference to the functional extracellular domain of a protein, can refer to an extracellular domain that retains its functionality, e.g., in the case of MHC I, ability to bind an antigen, ability to bind a T cell co-receptor, etc. In some embodiments, a replacement at the endogenous MHC locus results in a locus that fails to express an extracellular domain (e.g., a functional extracellular domain) of an endogenous MHC while expressing an extracellular domain (e.g., a functional extracellular domain) of a human MHC.

"Genetic or molecular marker," and their grammatical equivalents as used herein include polymorphic locus, i.e. a polymorphic nucleotide (a so-called single nucleotide polymorphism or SNP) or a polymorphic DNA sequence at a specific locus. A marker refers to a measurable, genetic characteristic with a fixed position in the genome, which is normally inherited in a Mendelian fashion, and which can be used for mapping a trait of interest. Thus, a genetic marker may be a short DNA sequence, such as a sequence surrounding a single base-pair change, i.e. a single nucleotide polymorphism or SNP, or a long DNA sequence, such as microsatellites or Simple Sequence Repeats (SSRs). The nature of the marker is dependent on the molecular analysis used and can be detected at the DNA, RNA, or protein level. Genetic mapping can be performed using molecular markers such as, but not limited to, RFLP (restriction fragment length polymorphisms), RAPD, AFLP, SSRs, or microsatellites. Appropriate primers or probes are dictated by the mapping method used.

"Humanized" and its grammatical equivalents as used herein include embodiments wherein all or a portion of an endogenous non-human gene or allele is replaced by a corresponding portion of an orthologous human gene or allele. For example, in some embodiments, the term "humanized" refers to the complete replacement of the coding region (e.g., the exons) of the endogenous non-human MHC gene or allele or fragment thereof with the corresponding capture sequence of the human MHC gene or allele or fragment thereof, while the endogenous non-coding region(s) (such as, but not limited to, the promoter, the 5' and/or 3' untranslated region(s), enhancer elements, etc.) of the non-human animal is not replaced.

"Improving" and its grammatical equivalents as used herein include any improvement recognized by one of skill in the art. For example, improving transplantation can mean lessening hyperacute rejection, which can encompass a decrease, lessening, or diminishing of an undesirable effect or symptom. In some aspects, a clinically relevant improvement is achieved.

"Locus" (loci plural) or "site" and their grammatical equivalents as used herein include a specific place or places on a chromosome where, for example, a gene, a genetic marker or a QTL is found.

"Minimally altered" and its grammatical equivalents as used herein include alteration of a donor animal genome including removing and replacing certain distinct sequences of native base pairs appearing on the donor animal's genome and replacing each such sequence with a synthetic sequence comprising the same number of base pairs, with no net change to the number of base pairs in the donor animal's genome, while not disturbing other aspects of the donor animal's native genome including, for example, introns and other codons naturally existing in the donor animal genome. For example, in the case of a swine as a donor animal, a minimally altered swine can include specific alterations removing or deactivating certain SLA exons to regulate the donor swine cell's extracellular expression or non-expression of MHC Class II, Ia, and/or Ib; reprogramming certain native, naturally occurring swine cell SLA exons to regulate the swine cell's extracellular expression or non-expression of MHC Class II; conserving or otherwise not removing swine introns existing in or in the vicinity of the otherwise engineered sequences; increasing the expression of swine CTLA4 and PD-1; and removing or deactivating alpha-1,3 galactosyltransferase, cytidine monophosphate-N-acetylneuraminic acid hydroxylase, and β1,4-N-acetylgalactosaminyltransferase.

"Minimally manipulated" and its grammatical equivalents as used herein include treatment of source animals, biological products derived from those source animals, and other biological products with minimal physical alteration of the related cells, organs, or tissues such that such animals and products are substantially in their natural state.

"Ortholog," "orthologous," and their grammatical equivalents as used herein include a polynucleotide from one species that corresponds to a polynucleotide in another species, which has the same function as the gene or protein or QTL, but is (usually) diverged in sequence from the time point on when the species harboring the genes or quantitative trait loci diverged (i.e. the genes or quantitative trait loci evolved from a common ancestor by speciation).

"Personalized" or "individualized," and their grammatical equivalents as used herein, include a gene, allele, genome, proteome, cell, cell surface, tissue, or organ from a non-human animal which is adapted to the needs or special circumstances of an individual human recipient or a specific human recipient subpopulation.

"Quantitative trait locus (QTL)" and its grammatical equivalents as used herein include a stretch of DNA (such as a chromosome arm, a chromosome region, a nucleotide sequence, a gene, and the like) that is closely linked to a gene that underlies the trait in question. "QTL mapping" involves the creation of a map of the genome using genetic or molecular markers, like AFLP, RAPD, RFLP, SNP, SSR, and the like, visible polymorphisms and allozymes, and determining the degree of association of a specific region on the genome to the inheritance of the trait of interest. As the markers do not necessarily involve genes, QTL mapping results involve the degree of association of a stretch of DNA with a trait rather than pointing directly at the gene responsible for that trait. Different statistical methods are used to ascertain whether the degree of association is significant or not. A molecular marker is said to be "linked" to a gene or locus if the marker and the gene or locus have a greater association in inheritance than would be expected from independent assortment, i.e. the marker and the locus co-segregate in a segregating population and are located on the same chromosome. "Linkage" refers to the genetic distance of the marker to the locus or gene (or two loci or two markers to each other). The closer the linkage, the smaller the likelihood of a recombination event taking place, which separates the marker from the gene or locus. Genetic distance (map distance) is calculated from recombination frequencies and is expressed in centiMorgans (cM).

"Reprogram," "reprogrammed," including in reference to "immunogenomic reprogramming," and their grammatical equivalents as used herein, refer to the replacement or substitution of endogenous nucleotides in the donor animal with orthologous nucleotides based on a separate reference sequence, wherein frameshift mutations are not introduced by such reprogramming. In addition, reprogramming results in no net loss or net gain in the total number of nucleotides in the donor animal genome, or results in a net loss or net gain in the total number of nucleotides in the donor animal genome that is equal to no more than 1%, no more than 2%, no more than 3%, no more than 4%, no more than 5%, no more than 6%, no more than 7%, no more than 8%, no more than 9%, no more than 10%, no more than 12%, no more than 15%, or no more than 20% of the number of nucleotides in the separate reference sequence. In one example of "reprogramming," an endogenous non-human nucleotide, codon, gene, or fragment thereof is replaced with a corresponding synthetic nucleotide, codon, gene, or fragment thereof based on a human capture sequence, through which the total number of base pairs in the donor animal sequence is equal to the total number of base pairs of the human capture sequence.

"Tolerogenic" and its grammatical equivalents as used herein include characteristics of an organ, cell, tissue, or other biological product that are tolerated by the reduced response by the recipient's immune system upon transplantation.

"Transgenic" and its grammatical equivalents as used herein include donor animal genomes that have been modified to introduce non-native genes from a different species into the donor animal's genome at a non-orthologous, non-endogenous location such that the homologous, endogenous version of the gene (if any) is retained in whole or in part. "Transgene," "transgenic," and grammatical equivalents as used herein do not include reprogrammed genomes, knock-in/knockouts, site-directed mutagenic substitutions or series thereof, or other modifications as described and claimed herein. By way of example, "transgenic" swine include those having or expressing hCD46 ("human membrane cofactor protein," or "MCP"), hCD55 ("human decay-accelerating factor," "DAF"), human B2M (beta-2-microglobulin), and/or other human genes, achieved by insertion of human gene sequences at a non-orthologous, non-endogenous location in the swine genome without the replacement of the endogenous versions of those genes.

Biological products can also include, but are not limited to, those disclosed herein (e.g., in the specific examples), as well as any and all other tissues, organs, and/or purified or substantially pure cells and cell lines harvested from the source animals. In some aspects, tissues that are utilized for xenotransplantation as described herein include, but are not limited to, areolar, blood, adenoid, bone, brown adipose, cancellous, cartilaginous, cartilage, cavernous, chondroid, chromaffin, connective tissue, dartoic, elastic, epithelial, Epithelium, fatty, fibrohyaline, fibrous, Gamgee, Gelatinous, Granulation, gut-associated lymphoid, Haller's vascular, hard hemopoietic, indifferent, interstitial, investing, islet, lymphatic, lymphoid, mesenchymal, mesonephric, mucous connective, multilocular adipose, muscle, myeloid, nasion soft, nephrogenic, nerve, nodal, osseous, osteogenic, osteoid, periapical, reticular, retiform, rubber, skeletal muscle, smooth muscle, and subcutaneous tissue. In some aspects, organs that are utilized for xenotransplantation as described herein include, but are not limited to, skin, kidneys, liver, brain, adrenal glands, anus, bladder, blood, blood vessels, bones, cartilage, cornea, ears, esophagus, eye, glands, gums, hair, heart, hypothalamus, intestines, large intestine, ligaments, lips, lungs, lymph, lymph nodes and lymph vessels, mammary glands, mouth, nails, nose, ovaries, oviducts, pancreas, penis, pharynx, pituitary, pylorus, rectum, salivary glands, seminal vesicles, skeletal muscles, skin, small intestine, smooth muscles, spinal cord, spleen, stomach, suprarenal capsule, teeth, tendons, testes, thymus gland, thyroid gland, tongue, tonsils, trachea, ureters, urethra, uterus, and vagina.

Several types of porcine cells may be used. Porcine cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, porcine cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts.

Viable porcine in which both alleles of the alpha 1,3 galactosyltransferase gene have been inactivated may be provided, as well as organs, tissues, and cells derived from such porcine, which are useful for xenotransplantation. In one embodiment, porcine organs, tissues and/or purified or substantially pure cells or cell lines are obtained from pigs that lack any expression of functional alpha1,3GT. In one embodiment, organs are provided that are useful for xenotransplantation. Any porcine organ can be used, including, but not limited to: brain, heart, lungs, glands, brain, eye, stomach, spleen, pancreas, kidneys, liver, intestines, uterus, bladder, skin, hair, nails, ears, nose, mouth, lips, gums, teeth, tongue, salivary glands, tonsils, pharynx, esophagus, large intestine, small intestine, rectum, anus, pylorus, thyroid gland, thymus gland, suprarenal capsule, bones, cartilage, tendons, ligaments, skeletal muscles, smooth muscles, blood vessels, blood, spinal cord, trachea, ureters, urethra, hypothalamus, pituitary, adrenal glands, ovaries, oviducts, uterus, vagina, mammary glands, testes, seminal vesicles, penis, lymph, lymph nodes and lymph vessels. In another embodiment tissues are provided that are useful for xenotransplantation. Any porcine tissue can be used, including, but not limited to: epithelium, connective tissue, blood, bone, cartilage, muscle, nerve, adenoid, adipose, areolar, bone, brown adipose, cancellous, muscle, cartaginous, cavernous, chondroid, chromaffin, dartoic, elastic, epithelial, fatty, fibrohyaline, fibrous, Gamgee, gelatinous, granulation, gut-associated lymphoid, Haller's vascular, hard hemopoietic, indifferent, interstitial, investing, islet, lymphatic, lymphoid, mesenchymal, mesonephric, mucous connective, multilocular adipose, myeloid, nasion soft, nephrogenic, nodal, osseous, osteogenic, osteoid, periapical, reticular, retiform, rubber, skeletal muscle, smooth muscle, and subcutaneous tissue. In a further embodiment, cells and cell lines from porcine animals that lack expression of functional alpha1, 3GT are provided. In one embodiment, these cells or cell lines can be used for xenotransplantation. Cells from any porcine tissue or organ can be used, including, but not limited to: epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, pancreatic insulin secreting cells, pancreatic alpha-2 cells, pancreatic beta cells, pancreatic alpha-1 cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopamiergic cells, squamous epithelial cells, osteocytes, osteoblasts, osteoclasts, dopaminergic cells, embryonic stem cells, fibroblasts and fetal fibroblasts. In a specific embodiment, pancreatic cells, including, but not limited to, Islets of Langerhans cells, insulin secreting cells, alpha-2 cells, beta cells, alpha-1 cells from pigs that lack expression of functional alpha-1,3-GT are provided. Nonviable derivatives may include tissues stripped of viable cells by enzymatic or chemical treatment these tissue derivatives can be further processed via crosslinking or other chemical treatments prior to use in transplantation. In some embodiments, the derivatives include extracellular matrix derived from a variety of tissues, including skin, urinary, bladder or organ submucosal tissues. Also, tendons, joints and bones stripped of viable tissue to include heart valves and other nonviable tissues as medical devices are provided.

According to some embodiments, the cells can be administered into a host in order in a wide variety of ways. Preferred modes of administration are parenteral, intraperitoneal, intravenous, intradermal, epidural, intraspinal, intrasternal, intra-articular, intra-synovial, intrathecal, intraarterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

Disorders that can be treated by infusion of the disclosed cells include, but are not limited to, diseases resulting from a failure of a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including aplastic anemia, pancytopenia, agranulocytosis, thrombocytopenia, red cell aplasia, Blackfan-Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma; autoimmune diseases including rheumatoid arthritis, diabetes type I, chronic hepatitis, multiple sclerosis, systemic lupus erythematosus;

genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phosphate dehydrogenase) variants 1, 2, 3, pyruvate kinase deficiency, congenital erythropoietin sensitivity, deficiency, sickle cell disease and trait, thalassemia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportionsin lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1-antirypsin deficiency, etc.

Diseases or pathologies may include neurodegenerative diseases, hepatodegenerative diseases, nephrodegenerative disease, spinal cord injury, head trauma or surgery, viral infections that result in tissue, organ, or gland degeneration, and the like. Such neurodegenerative diseases include but are not limited to, AIDS dementia complex; demyeliriating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supranucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multi-system disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Parkinson's Disease, Wernicke-Korsakoff syndrome; chronic alcoholism; Creutzfeldt-Jakob disease; Subacute sclerosing panencephalitis hallerrorden-Spatz disease; and Dementia pugilistica.

As described more fully in U.S. provisional patent application Nos. 16/830,213; 62/975,611, filed Feb. 12, 2020; 62/964,397, filed Jan. 22, 2020; 62/848,272, filed May 15, 2019; 62/823,455, filed Mar. 25, 2019, and U.S. non-provisional patent application Ser. No. 16/593,785, filed Oct. 4, 2019, which claims priority benefit of U.S. provisional application Nos. 62/742,188, filed Oct. 5, 2018; 62/756,925, filed Nov. 7, 2018; U.S. 62/756,955 filed Nov. 7, 2018; U.S. 62/756,977, filed Nov. 7, 2018; U.S. 62/756,993, filed Nov. 7, 2018; U.S. 62/792,282, filed Jan. 14, 2019; U.S. 62/795,527, filed Jan. 22, 2019; U.S. 62/823,455, filed Mar. 25, 2019; and U.S. 62/848,272, filed May 15, 2019, which are incorporated herein by reference in their entireties for all purposes, donor animal cells may be reprogrammed so that full immune functionality in the donor animal is retained, but the cell surface-expressing proteins and glycans are reprogrammed such that they are not recognized as foreign by the human recipient's immune system. Accordingly, only discrete and small portions of the animal's genome may need reprogramming so that the animal retains a functional immune system, but the animal's reprogrammed cells do not express cell surface-expressing proteins and glycans that elicit attack by the human recipient's immune system.

Artificial Intelligence (AI) and Machine Learning (ML) are widely applied in science and technology, including Immunology, Biotechnology, and Biopharmaceutical research and development. One example of AI application in Immunology is using a deep learning algorithm for the prediction of the set of epitopes presented by human MHC Class II from the protein sequence. In transplantation, AI may be applied to predict the outcome of operation based on combined analysis of image and clinical data. The deep learning model demonstrated to be more effective than multidimensional logistic regression in the prediction of short- and long-term outcomes of a heart transplant.

The genetic modification can be made utilizing genome editing techniques such as zinc-finger nucleases (ZFNs), transcription activator-like effector nucleases (TALENs), adeno-associated virus (AAV)-mediated gene editing, and clustered regularly interspaced palindromic repeat Cas9 (CRISPR-Cas9). These programmable nucleases enable the targeted generation of DNA double-stranded breaks (DSB), which promote the upregulation of cellular repair mechanisms, resulting in either the error-prone process of non-homologous end joining (NHEJ) or homology-directed repair (HDR), the latter of which is used to integrate exogenous donor DNA templates. CRISPR-Cas9 may also be used to perform precise modifications of genetic material. For example, the genetic modification via CRISPR-Cas9 can be performed in a manner described in Kelton, W. et. al., "Reprogramming MHC specificity by CRISPR-Cas9-assisted cassette exchange," Nature, Scientific Reports, 7:45775 (2017) ("Kelton"), the entire disclosure of which is incorporated herein by reference. Reprogramming may be performed using CRISPR-Cas9 to mediate rapid and scarless exchange of entire alleles, e.g., MHC, HLA, SLA, etc.

CRISPR-Cas9 may be used to mediate the rapid and scarless exchange of entire MHC alleles at a specific native locus in swine cells. Multiplex targeting of Cas9 with two gRNAs is used to introduce single or double-stranded breaks flanking the MHC allele, enabling replacement with the template HLA/MHC sequence (provided as a single or double-stranded DNA template).

The expression of polymorphic protein motifs of the donor animal's MHC can be further modified by knock-out methods known in the art. For example, knocking out one or more genes may include deleting one or more genes from a genome of a non-human animal. Knocking out may also include removing all or a part of a gene sequence from a non-human animal. It is also contemplated that knocking out can include replacing all or a part of a gene in a genome of a non-human animal with one or more nucleotides. Knocking out one or more genes can also include substituting a sequence in one or more genes thereby disrupting the expression of one or more genes. Knocking out one or more genes can also include replacing a sequence in one or more genes thereby disrupting expression of the one or more genes without frameshifts or frame disruptions in the native donor swine's SLA/MHC gene. For example, replacing a sequence can generate a stop codon at the beginning of one or more genes, which can result in a nonfunctional transcript or protein. For example, if a stop codon is created within one or more genes, the resulting transcription and/or protein can be disrupted, silenced, and rendered nonfunctional.

Alteration by nucleotide replacement of STOP codon at exon regions of the wild-type swine's SLA-DR may be utilized to avoid provocation of natural cellular mediated immune response (CD8+ T Cell) by the recipient, including making cells that lack functional expression of SLA-DR, SLA-1, SLA-2. In some embodiments, TAA is utilized. In other embodiments, TAG is utilized. In other embodiments, TGA is utilized.

Insertion or creation (by nucleotide replacement) of STOP codon at exons regions of the wild-type swine's second, identical duplication B2-microglobulin gene may be utilized to reduce the B2-microglobulin mRNA expression level in pigs. It will be understood that B2-microglobulin is a predominant immunogen, specifically a non-gal xeno-antigen.

The recipient's HLA/MHC gene may be sequenced, and template HLA/MHC sequences are prepared based on the recipient's HLA/MHC genes. A known human HLA/MHC genotype from a World Health Organization (WHO) database may be used for genetic reprogramming of swine of the present disclosure.

CRISPR-Cas9 plasmids are prepared, e.g., using polymerase chain reaction and the recipient's HLA/MHC sequences are cloned into the plasmids as templates. CRISPR cleavage sites at the SLA/MHC locus in the swine cells are identified and gRNA sequences targeting the cleavage sites and are cloned into one or more CRISPR-Cas9 plasmids. CRISPR-Cas9 plasmids are then administered into the swine cells and CRISPR/Cas9 cleavage is performed at the MHC locus of the swine cells.

The SLA/MHC locus in the swine cells is precisely replaced with one or more template HLA/MHC sequences matching the known human HLA/MHC sequences or the recipient's sequenced HLA/MHC genes. Cells of the swine are sequenced after performing the SLA/MHC reprogramming steps in order to determine if the SLA/MHC sequences in the swine cells have been successfully reprogrammed. One or more cells, tissues, and/or organs from the HLA/MHC sequence-reprogrammed swine are transplanted into a human recipient.

The modification to the donor SLA/MHC to match recipient HLA/MHC causes the expression of specific MHC molecules in the new swine cells that are identical, or virtually identical, to the MHC molecules of a known human genotype or the specific human recipient. In one aspect, the present disclosure involves making modifications limited to only specific portions of specific SLA regions of the swine's genome to retain an effective immune profile in the swine while biological products are tolerogenic when transplanted into human recipients such that use of immunosuppressants can be reduced or avoided. In contrast to aspects of the present disclosure, xenotransplantation studies of the prior art required immunosuppressant use to resist rejection. The swine genome may be reprogrammed to disrupt, silence, cause nonfunctional expression of swine genes corresponding to HLA-A, HLA-B, and DR, and to reprogram via substitution of HLA-C, HLA-E, HLA-F, and/or HLA-G. The swine genome may be reprogrammed to knock-out swine genes corresponding to HLA-A, HLA-B, HLA-C, HLA-F, DQ, and DR, and to knock-in HLA-C, HLA-E, HLA-G. The swine genome may be reprogrammed to knock-out swine genes corresponding to HLA-A, HLA-B, HLA-C, HLA-F, DQ, and DR, and to knock-in HLA-C, HLA-E, HLA-G, HLA-F, and DQ. The swine genome may be reprogrammed to knock-out SLA-1; SLA-6,7,8; SLA-MIC2; and SLA-DQA; SLA-DQB1; SLA-DQB2, and to knock-in HLA-C; HLA-E; HLA-G; and HLA-DQ. HLA-C expression may be reduced in the reprogrammed swine genome. By reprogramming the swine cells to be invisible to a human's immune system, this reprogramming thereby minimizes or even eliminates an immune response that would have otherwise occurred based on swine MHC molecules otherwise expressed from the donor swine cells.

Various cellular marker combinations in swine cells are made and tested to prepare biologically reprogrammed swine cells for acceptance by a human patient's body for various uses. For these tests, Porcine Aorta Endothelial Cells, fibroblast, or a transformed porcine macrophage cell line available from ATCC® (3D4/21) are used.

The knockout only and knockout plus knock-in cell pools are generated by designing and synthesizing a guide RNA for the target gene. Each guide RNA is composed of two components, a CRISPR RNA (crRNA) and a trans-activating RNA (tracrRNA). These components may be linked to form a continuous molecule called a single guide RNA (sgRNA) or annealed to form a two-piece guide RNA, to include trans-activating crispr RNA (tracrRNA).

CRISPR components (gRNA and Cas9) can be delivered to cells in DNA, RNA, or ribonucleoprotein (RNP) complex formats. The DNA format involves cloning gRNA and Cas9 sequences into a plasmid, which is then introduced into cells. If permanent expression of gRNA and/or Cas9 is desired, then the DNA can be inserted into the host cell's genome using a lentivirus. Guide RNAs can be produced either enzymatically (via in vitro transcription) or synthetically. Synthetic RNAs are typically purer than IVT-derived RNAs and can be chemically modified to resist degradation. Cas9 can also be delivered as RNA. The ribonucleoproteins (RNP) format consists of gRNA and Cas9 protein. The RNPs are pre-complexed together and then introduced into cells. This format is easy to use and has been shown to be highly effective in many cell types.

After designing and generating the guide RNA, the CRISPR components are introduced into cells via one of several possible transfection methods, such as lipofection, electroporation, nucleofection, or microinjection. After a guide RNA and Cas9 are introduced into a cell culture, they produce a DSB at the target site within some of the cells. The NHEJ pathway then repairs the break, potentially inserting or deleting nucleotides (indels) in the process. Because NHEJ may repair the target site on each chromosome differently, each cell may have a different set of indels or a combination of indels and unedited sequences.

For knock-in cells, the desired sequences are knocked into the cell genome through insertion of genomic material using, e.g., homology-directed repair (HDR).

It will be further understood that disruptions and modifications to the genomes of source animals provided herein can be performed by several methods including, but not limited to, through the use of clustered regularly interspaced short palindromic repeats ("CRISPR"), which can be utilized to create animals having specifically tailored genomes. Such genome modification can include, but not be limited to, any of the genetic modifications disclosed herein, and/or any other tailored genome modifications designed to reduce the bioburden and immunogenicity of products derived from such source animals to minimize immunological rejection.

CRISPR/CRISPR-associated protein (Cas), originally known as a microbial adaptive immune system, has been adapted for mammalian gene editing recently. The CRISPR/Cas system is based on an adaptive immune mechanism in bacteria and archaea to defend the invasion of foreign genetic elements through DNA or RNA interference. Through mammalian codon optimization, CRISPR/Cas has been adapted for precise DNA/RNA targeting and is highly efficient in mammalian cells and embryos. The most commonly used and intensively characterized CRISPR/Cas system for genome editing is the type II CRISPR system from *Streptococcus pyogenes*; this system uses a combination of Cas9 nuclease and a short guide RNA (gRNA) to target specific DNA sequences for cleavage. A 20-nucleotide gRNA complementary to the target DNA that lies immediately 5' of a PAM sequence (e.g., NGG) directs Cas9 to the target DNA and mediates cleavage of double-stranded DNA to form a DSB. Thus, CRISPR/Cas9 can achieve gene targeting in any N20-NGG site.

The human leukocyte antigen (HLA) system or complex is a gene complex encoding the major histocompatibility complex (MHC) proteins in humans. These cell-surface proteins are responsible for the regulation of the immune system in humans. The HLA gene complex resides on a 3 Mbp stretch within chromosome 6p21. HLA genes are highly polymorphic, which means that they have many different alleles, allowing them to fine-tune the adaptive immune system. The proteins encoded by certain genes are also known as antigens, as a result of their historic discovery as factors in organ transplants. Different classes have different functions.

The HLA segment is divided into three regions (from centromere to telomere), Class II, Class III, and Class I. Classical Class I and Class II HLA genes are contained in Class I and Class II regions, respectively, whereas the Class III locus bears genes encoding proteins involved in the immune system but not structurally related to MHC molecules. The classical HLA Class I molecules are of three types, HLA-A, HLA-B, and HLA-C. Only the α chains of these mature HLA Class I molecules are encoded within the Class I HLA locus by the respective HLA-A, HLA-B, and HLA-C genes. In contrast, the beta-2 microglobulin β2m chain encoded by the β2m gene is located on chromosome 15. The classical HLA Class II molecules are also of three types (HLA-DP, HLA-DQ, and HLA-DR), with both the α and β chains of each encoded by a pair of adjacent loci. In addition to these classical HLA Class I and HLA Class II genes, the human MHC locus includes a long array of HLA pseudogenes as well as genes encoding non-classical MHCI and MHCII molecules. HLA-pseudogenes are an indication that gene duplication is the main driving force for HLA evolution, whereas non-classical MHCI and MHCII molecules often serve a restricted function within the immune system quite distinct from that of antigen presentation to αβ TCRs.

Aside from the genes encoding the antigen-presenting proteins, there are a large number of other genes, many involved in immune function, located on the HLA complex. Diversity of HLAs in the human population is one aspect of disease defense, and, as a result, the chance of two unrelated individuals with identical HLA molecules on all loci is extremely low. HLA genes have historically been identified as a result of the ability to successfully transplant organs between HLA-similar individuals.

Class I MHC molecules are expressed on all nucleated cells, including tumor cells. They are expressed specifically on T and B lymphocytes, macrophages, dendritic cells and neutrophils, among other cells, and function to display peptide fragments (typically 8-10 amino acids in length) on the surface to CD8+ cytotoxic T lymphocytes (CTLs). CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide.

MHC Class I protein comprises an extracellular domain (which comprises three domains: $\alpha_1$, $\alpha_2$, and $\alpha_3$), a transmembrane domain, and a cytoplasmic tail. The $\alpha_1$ and $\alpha_2$ domains form the peptide-binding cleft, while the $\alpha_3$ interacts with β2-microglobulin. Class I molecules consist of two chains: a polymorphic α-chain (sometimes referred to as heavy chain) and a smaller chain called β2-microglobulin (also known as light chain), which is generally not polymorphic. These two chains form a non-covalent heterodimer on the cell surface. The α-chain contains three domains (α1, α2, and α3). Exon 1 of the α-chain gene encodes the leader sequence, exons 2 and 3 encode the α1 and α2 domains, exon 4 encodes the α3 domain, exon 5 encodes the transmembrane domain, and exons 6 and 7 encode the cytoplasmic tail. The α-chain forms a peptide-binding cleft involving the α1 and α2 domains (which resemble Ig-like domains) followed by the α3 domain, which is similar to β2-microglobulin.

β2 microglobulin is a non-glycosylated 12 kDa protein; one of its functions is to stabilize the MHC Class I α-chain. Unlike the α-chain, the β2 microglobulin does not span the membrane. The human β2 microglobulin locus is on chromosome 15 and consists of 4 exons and 3 introns. Circulating forms of β2 microglobulin are present in serum, urine, and other body fluids; non-covalently MHC I-associated β2 microglobulin can be exchanged with circulating β2 microglobulin under physiological conditions.

MHC Class II protein comprises an extracellular domain (which comprises three domains: $\alpha_1$, $\alpha_2$, $\beta 1$, and $\beta 1$), a transmembrane domain, and a cytoplasmic tail. The $\alpha_1$ and β1 domains form the peptide-binding cleft, while the $\alpha_1$ and β1 interacts with the transmembrane domain.

In addition to the aforementioned antigens, the Class I antigens include other antigens, termed non-classical Class I antigens, in particular the antigens HLA-E, HLA-F and HLA-G; this latter, in particular, is expressed by the trophoblasts of the normal human placenta in addition to HLA-C.

Artificial Intelligence (AI) is one or a multitude of manifestations of intelligence behavior characterized by logic, comprehension, forward-planning, result in anticipation, problem-solving, learning, etc. demonstrated by man-created mechanical, electric, or computer-simulated machines rather than living creatures. Machine Learning (ML) is typically defined as the use and development of AI capable of learning and adapting without following explicit instructions, by using algorithms and statistical models to analyze and draw inferences from patterns in data.

A Digital Twin (DT) is a digital replica of a living or non-living physical entity (physical assets, processes, people, places, systems and devices) that simulates the behavior of the modeled object in response to changes in the environment or experimental conditions. DT technology can be applied for many purposes such as visualization, simulation, diagnostics, prediction prognostic, and other use cases of complex systems, alone or in combination with the material implementation of modeled objects.

Reinforcement learning (RL) is a form of machine learning that enables an agent, i.e. a computational model to learn by interaction with a natural or simulated environment. Reinforcement learning is one of three basic machine learning paradigms, alongside supervised learning and unsupervised learning. In RL the agent (model) learns from the results of action in repeating the trial-and-error process rather than from being explicitly taught or given a learning set of data. In the process of RL, the agent receives a numerical reward for each action. The reward estimates the degree of success for the actions of the agent. The agent attempts to maximize the reward and it selects its actions on the basis of its past experiences (exploitation) and also as well as by new choices (exploration).

Though both supervised and reinforcement learning use the mapping between input and output, unlike supervised learning where feedback provided to the agent is the correct set of actions for performing a task, reinforcement learning uses rewards and punishment as signals for positive and negative behavior.

As compared to unsupervised learning, reinforcement learning is different in terms of goals. While the goal in unsupervised learning is to find similarities and differences between data points, in reinforcement learning the goal is to find a suitable action model that would maximize the total cumulative reward of the agent.

The present disclosure provides techniques involving artificial intelligence, and specifically machine learning algorithms and models based on experimental data to provide technical improvements in, inter alia, modeling of an animal source/donor, an animal genome responding to gene editing, and/or a grafted engineered cell, tissue, or organ in a transplant recipient in order to, for example, match a donor source to a recipient, reduce or eliminate transplant rejection in a human recipient, increase vitality and reduce rejection, and engage in prognostic monitoring of graft and recipient health status.

In this disclosure, Digital Twin (DT) technology is combined with AI-based on the principles of RL where DT is the learning agent of RL. Training on DT using public, experimental and other data creates an instance of DT helping to guide the development, select optimal parameters, predict the outcomes and drive (monitor with corrections) the process of xenotransplantation of cells, tissues, and organs. Instances of DT can control different stages and aspects of xenotransplantation. Multiple instances of DT can be combined in a structured manner to control the entire process of xenotransplantation.

Embodiments of the disclosure may employ other supervised machine learning techniques when training data is available. In the absence of training data embodiments may employ unsupervised machine learning. Alternatively, embodiments may employ semi-supervised machine learning, using a small amount of label data and a large amount of unlabeled data. Embodiments may also employ feature selection to select the subset of the most relevant features to optimize performance of the machine learning model. Depending on the type of machine learning approach selected, as alternatives or in addition to linear regression, embodiments may employ for example, logistic regression, neural networks, support vector machines, decision trees, hidden Markov models, Bayesian networks, Gram Schmidt, reinforcement-based learning, cluster-based learning, including hierarchical clustering genetic algorithms, and any other suitable learning machines known in the art.

Embodiments may employ graphics processing unit accelerated architectures that have found increasing popularity in performing machine learning tasks particularly in the form of deep neural networks.

Genomic automation of the methods of the present disclosure enables high throughput phenotypic screening and identification of target products from multiple genetic alteration libraries simultaneously.

The aforementioned genomic engineering predictive modeling platform is premised upon the fact that hundreds and thousands of alterations are constructed in a high throughput fashion. The robotic and computer systems described are the structural mechanisms by which such a high throughput process can be carried out.

In some embodiments, the present disclosure teaches methods of improving cell, tissue, or organ therapy productivities, or rehabilitating current design candidates. As a part of this process, the present disclosure teaches methods of assembling DNA, building new therapy design candidate sequences, and screening design candidates for immunogenicity.

According to some embodiments, a donor genome may be digitally modeled using artificial intelligence, including machine learning and deep learning techniques, for matching a source (e.g., non-human animal) of graft organ and tissues to a human recipient or a human subpopulation based on data from genome sequencing, e.g., a capture sequence.

According to some embodiments, a non-human genome responding to gene editing may be digitally modeled using artificial intelligence, including machine learning and deep learning techniques, to reduce or eliminate organ rejection in a human recipient based on sequencing data, e.g., a capture sequence.

According to some embodiments, living tissue of an immunogenomically reprogrammed donor may be digitally modeled using artificial intelligence, including machine learning and deep learning techniques, for increasing vitality and reducing rejection when in contact with human living cells, tissues, and organ in in vitro experiments based on high-throughput instrumental multi-omics data (e.g., genomics, transcriptomics, proteomics, metabolomics, etc.).

According to some embodiments, a grafted engineered cell, tissue, or organ in a transplant recipient may be digitally modeled using artificial intelligence, including machine learning and deep learning techniques, for continuous prognostic monitoring of graft and recipient health status based on heterogeneous accumulated and real-time observation data.

Machine learning may generally refer to algorithms and models that computer-based systems use to perform a specific task, relying on patterns and inference. Machine learning algorithms may build a model based on sample data, or training data, to make predictions or decisions, often without being explicitly programmed to perform such tasks.

Supervised machine learning algorithms build a model out of a set of training data that contains both the inputs and the desired outputs. In some iterations, each training example is represented in a model as a feature vector, and the training data is represented by a matrix. Through iterative optimization of an objective function, a supervised learning algorithm may learn a function that can be used to predict the output associated with new input.

Unsupervised machine learning algorithms build a model out of a set of training data that includes only inputs. The algorithms find structure in the input data through techniques such as grouping or clustering of datapoints. Semi-supervised learning may encompass the use of labeled training data, as in supervised learning, as well as unlabeled data, as in unsupervised learning.

Several different types of models may be used for the machine learning applications described herein, such as but not limited to artificial neural networks, decision trees, support vector machines, regression analysis, Bayesian networks, and genetic algorithms.

It will be understood that, in the context of swine-to-human xenotransplantation, each human recipient will have a major histocompatibility complex (MHC) (Class I, Class II, and/or Class III) that is unique to that individual and will not match the MHC of the donor swine. Accordingly, it will be understood that when a donor swine graft is introduced to the recipient, the swine MHC molecules themselves act as antigens, provoking an immune response from the recipient, leading to transplant rejection.

Human leukocyte antigen (HLA) genes show incredible sequence diversity in the human population. For example, there are >4,000 known alleles for the HLA-B gene alone. The genetic diversity in HLA genes in which different alleles have different efficiencies for presenting different antigens is believed to be a result of evolution conferring better population-level resistance against the wide range of different pathogens to which humans are exposed. This genetic diversity also presents problems during xenotransplantation where the recipient's immune response is the most important factor dictating the outcome of engraftment and survival after transplantation.

In accordance with one aspect, a donor swine is provided with a genome that is biologically engineered to express a specific set of known human HLA molecules. Such HLA sequences can be obtained, e.g., from the IPD-IMGT/HLA database (available at ebi.ac.uk/ipd/imgt/hla/) and the international ImMunoGeneTics information System® (available at imgt.org). For example, HLA-A1, B8, DR17 are the most common HLA haplotype among Caucasians, with a frequency of 5%. Thus, the disclosed method can be performed using the known MHC/HLA sequence information in combination with the disclosures provided herein. The HLA sequences are obtainable through online archives or databases such as Ensembl (vega.archive.ensembl.org/index-.html). The exact location of the HLA-DQA1 gene, the length of the respective gene (exon and intron), and the exact nucleotide sequences of HLA-DQA1 could be obtained. In some aspects, the present disclosure includes analyzing one or more of such databases (or databases generated by a user, an institution, or a vendor) using machine learning algorithms to create models of genetic sequences based on common HLA haplotypes among humans.

In one aspect, a donor animal, e.g., a donor swine's SLA/MHC gene is used as a reference template in creating the replacement template. In implementing the present disclosure, the swine's genome may be sequenced through whole genome sequencing. The sequence of the donor animal's genome is then analyzed using machine learning algorithms taking into account information regarding human subpopulation sequence information and the target human recipient to produce a model sequence that is a minimally altered reprogrammed swine genome that provides cells, tissues, and organs that are tolerogenic when transplanted into the human recipient. Accordingly, machine learning and the algorithms disclosed herein may be used to determine minimal editing approaches for reprogramming a non-human animal donor.

According to some embodiments, it may be infeasible or impracticable to create a bespoke genetically modified non-human animal donor for each human recipient. Accordingly, it may be desirable to generate an inventory or population of genetically modified non-human animal donors with tissue and organs that are tolerogenic for a majority of potential classes of human recipients. The AI/ML processes disclosed herein may be used to identify and generate a set of models, or a minimum set of models, of recipient genetic sequences, wherein each model reflects a class or group of humans with common HLA haplotypes. The processes disclosed herein may be further used to identify, based on the set of models of genetic sequences, groups of candidate non-human animal donors suitable for each model. In some embodiments, it may be preferable to identify a minimum number of groups of candidate non-human animal donors with cells, tissues, and organs that are tolerogenic when transplanted into a majority of human recipients. For illustrative purposes only, the techniques disclosed herein may identify that, for example, that a predetermined number of populations of genetically modified swine (e.g., 50) can provide donor cells, tissues, and organs that are tolerogenic for a predetermined percentage (e.g., 90%) of the human recipient population.

In some embodiments, experimental data from genome sequencing may be used for training a machine learning algorithm. The experimental data may include data from studies evaluating compatibility of a non-human donor to a human recipient based on respective MHC sequence (e.g., a SLA sequence for a porcine donor and an HLA sequence for a human recipient). Such studies may include, for example, a mixed lymphocyte reaction (MLR) assay experiment, or similar studies, that indicate xenotransplantation compatibility of the donor and recipient based on respective MHC sequences. Such experimental data may be used as training data to build a model that correlates an input human HLA sequence to a suitable non-human candidate donor. The machine learning model may use the experimental data to update the identification of classes of human recipients and matches of such classes to groups of candidate non-human animal donors.

In some embodiments, the immune response of the modified swine cells is evaluated through Mixed Lymphocyte Reaction (MLR) study. Responder cells can be either PBMC, CD4+ T cells, CD8+ T cells or other subpopulations of T cells. PBMC represents all the immune cells that are present in the recipient and the measured response reflects the ability of the responders to mount an immune response to the stimulator cells, for example, a comparison of unmodified PAM cells and modified PAM cells. Alternatively, PAECs or fibroblasts may be used. The measured proliferation consists of both CD4+ and CD8+ T cells which interact with MHC Class II and I, respectively. Using only CD4+ T cells against the unmodified or modified PAM cells measures the response to MHC Class II glycoproteins, DR and DQ. For example, in an MLR where the SLA DR is knocked out in the PAM cells, the CD4+ T cell proliferative response will be decreased; or when SLA-DQ gene is modified by using a sequence from a "recipient" [the responder] the proliferative response will be decreased since in this case the responder recognizes the DQ glycoprotein as self, whereas, in the DR knock-out, DR was absent and thus a signal could not be generated.

In one aspect, the present disclosure includes a biological system for generating and preserving a repository of personalized, humanized transplantable cells, tissues, and organs for transplantation, wherein the biological system is biologically active and metabolically active, the biological system comprising genetically reprogrammed cells, tissues, and organs in a non-human animal for transplantation into a human recipient. For example, the non-human animal is a genetically reprogrammed swine for xenotransplantation of cells, tissue, and/or an organ isolated from the genetically reprogrammed swine, the genetically reprogrammed swine comprising a nuclear genome that has been reprogrammed to replace a plurality of nucleotides in a plurality of exon regions of a major histocompatibility complex of a wild-type swine with a plurality of synthesized nucleotides from a human captured reference sequence. In one aspect, cells of said genetically reprogrammed swine do not present one or more surface glycan epitopes selected from alpha-Gal, Neu5Gc, and SDa. Further, genes encoding alpha-1,3 galactosyltransferase, cytidine monophosphate-N-acetylneuraminic acid hydroxylase (CMAH), and β1,4-N-acetylgalactosaminyltransferase are altered such that the genetically reprogrammed swine lacks functional expression of surface glycan epitopes encoded by those genes. In some aspects, the reprogrammed genome comprises site-directed mutagenic substitutions of nucleotides at exon regions of: i) at least one of the wild-type swine's SLA-1, SLA-2, and SLA-3 with nucleotides from an orthologous exon region of HLA-A, HLA-B, and HLA-C, respectively, of the human captured reference sequence; and ii) at least one the wild-type swine's SLA-6, SLA-7, and SLA-8 with nucleotides from an orthologous exon region of HLA-E, HLA-F, and HLA-G, respectively, of the human captured reference sequence; and iii) at least one of the wild-type swine's SLA-DR and SLA-DQ with nucleotides from an orthologous exon region of HLA-DR and HLA-DQ, respectively, of the human captured reference sequence.

FIG. 1 illustrates an exemplary flow chart according to some embodiments. The method may be performed by computer system 500, described in further detail in connection with FIG. 6. According to some embodiments, method 100 is for predicting a non-human candidate donor organ or tissue sample suitable for xenotransplantation into a human. Method 110 includes step 110 of obtaining a first human leucocyte antigen (HLA) sequence for a first human recipient in electronic format. Method 100 includes step 120 of submitting the first HLA sequence to a computer, wherein the computer correlates the first HLA sequence to one or more major histocompatibility complex (MHC) sequences of non-humans based on experimental data. Method 100 includes step 130 of obtaining from the computer an indication of a match of a first non-human candidate donor to the first human recipient based on the correlating.

Ascertaining the human recipient's HLA/MHC sequence can be done in any number of ways. For example, HLA/MHC genes are usually typed with targeted sequencing methods: either long-read sequencing or long-insert short-read sequencing. Conventionally, HLA types have been determined at 2-digit resolution (e.g., A*01), which approximates the serological antigen groupings. More recently, sequence specific oligonucleotide probes (SSOP) method has been used for HLA typing at 4-digit resolution (e.g., A*01:01), which can distinguish amino acid differences. Currently, targeted DNA sequencing for HLA typing is the most popular approach for HLA typing over other conventional methods. Since the sequence-based approach directly determines both coding and non-coding regions, it can achieve HLA typing at 6-digit (e.g., A*01:01:01) and 8-digit (e.g., A*01:01:01:01) resolution, respectively. HLA typing at the highest resolution is desirable to distinguish existing HLA alleles from new alleles or null alleles from clinical perspective.

Figure 2:
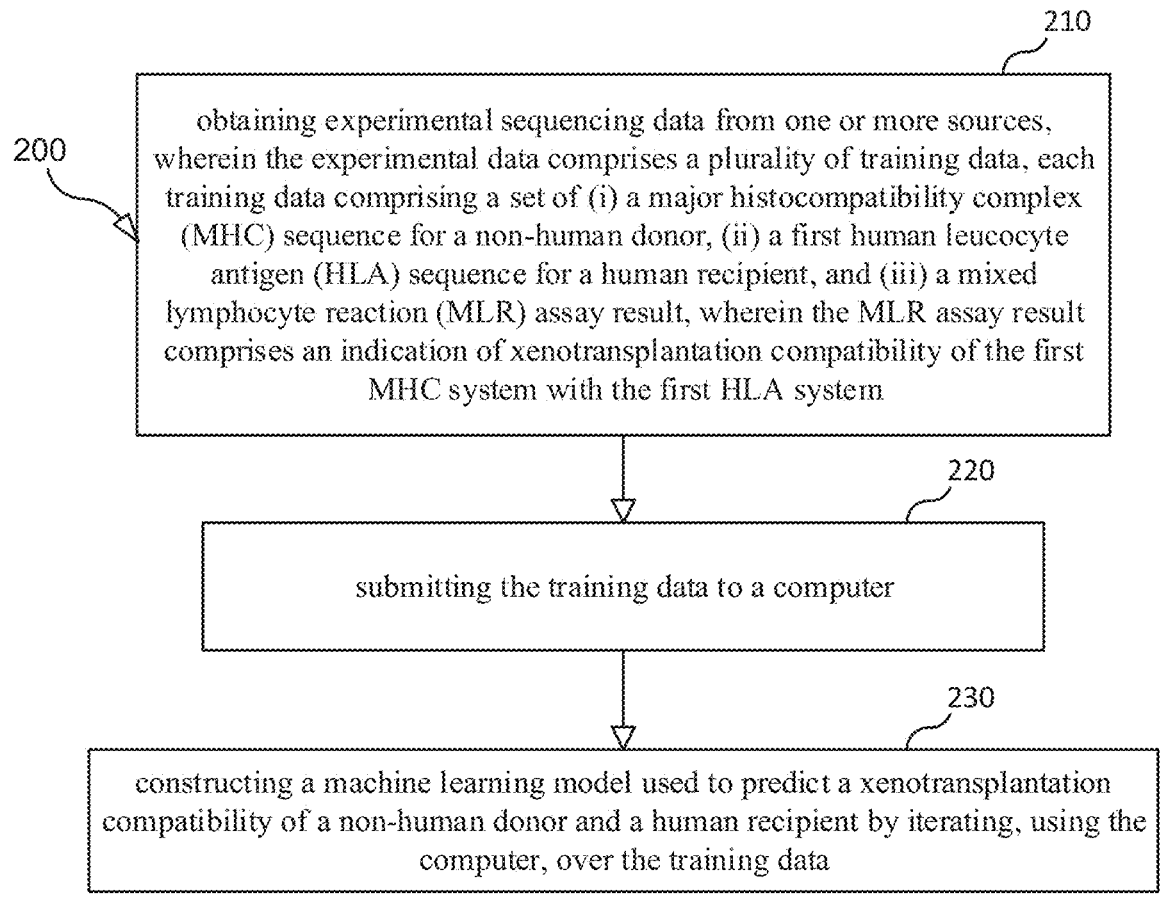
FIG. 2 illustrates an exemplary flow chart according to some embodiments.

FIG. 2 illustrates an exemplary flow chart according to some embodiments. According to some embodiments, method 200 is for predicting a non-human candidate tissue or organ sample suitable for xenotransplantation into a human. Method 200 includes step 210 of obtaining experimental sequencing data from one or more sources, wherein the experimental data comprises a plurality of training data, each training data comprising a set of (i) a major histocompatibility complex (MHC) sequence for a non-human donor, (ii) a first human leucocyte antigen (HLA) sequence for a human recipient, and (iii) a mixed lymphocyte reaction (MLR) assay result, wherein the MLR assay result comprises an indication of xenotransplantation compatibility of the first MHC system with the first HLA system. Method 200 includes step 220 of submitting the training data to a computer. Method 200 includes step 230 of constructing a machine learning model used to predict a xenotransplantation compatibility of a non-human donor and a human recipient by iterating, using the computer, over the training data.

In some embodiments, artificial intelligence techniques may be used for prognostic monitoring of a grafted engineered cell, tissue, or organ from a non-human donor in a human recipient. Experimental data may be obtained and used to train a machine learning algorithm and build a model to output a predictive health status of a human recipient based on observation data of the human recipient with the grafted engineered cell, tissue, or organ. The experimental data may include training data including a set of observation data of a human recipient with a grafted engineered cell, tissue, or organ and a health status of one or more of the human recipients or the grafted engineered cell, tissue, or organ. The training data may be submitted to a computer for processing, which iterates over the training data to construct a machine learning model used to predict a health status of a recipient of a grafted engineered cell, tissue, or organ from a non-human donor.

Figure 3:
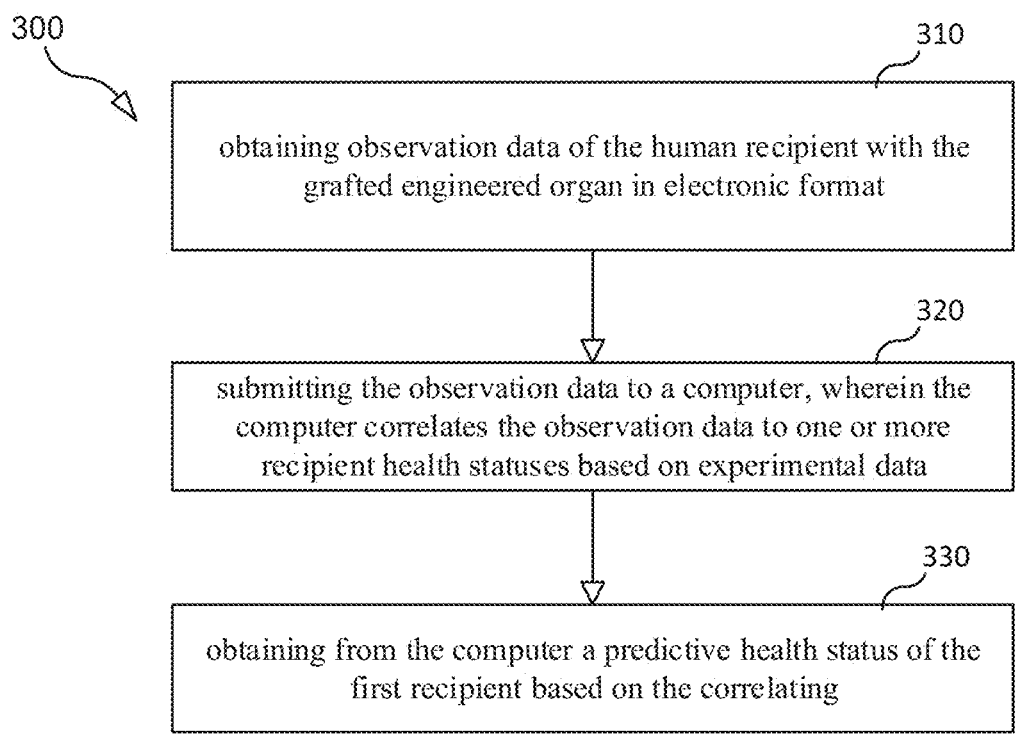
FIG. 3 illustrates an exemplary flow chart according to some embodiments.

FIG. 3 illustrates an exemplary flow chart according to some embodiments. According to some embodiments, method 300 is for prognostic monitoring of a grafted engineered cell, tissue, or organ from a non-human donor in a human recipient. Method 300 includes step 310 of obtaining observation data of the human recipient with the grafted engineered cell, tissue, or organ in electronic format. Method 300 includes step 320 of submitting the observation data to a computer, wherein the computer correlates the observation data to one or more recipient health statuses based on experimental data. Method 300 includes step 330 of obtaining from the computer a predictive health status of the first recipient based on the correlating.

Figure 4:
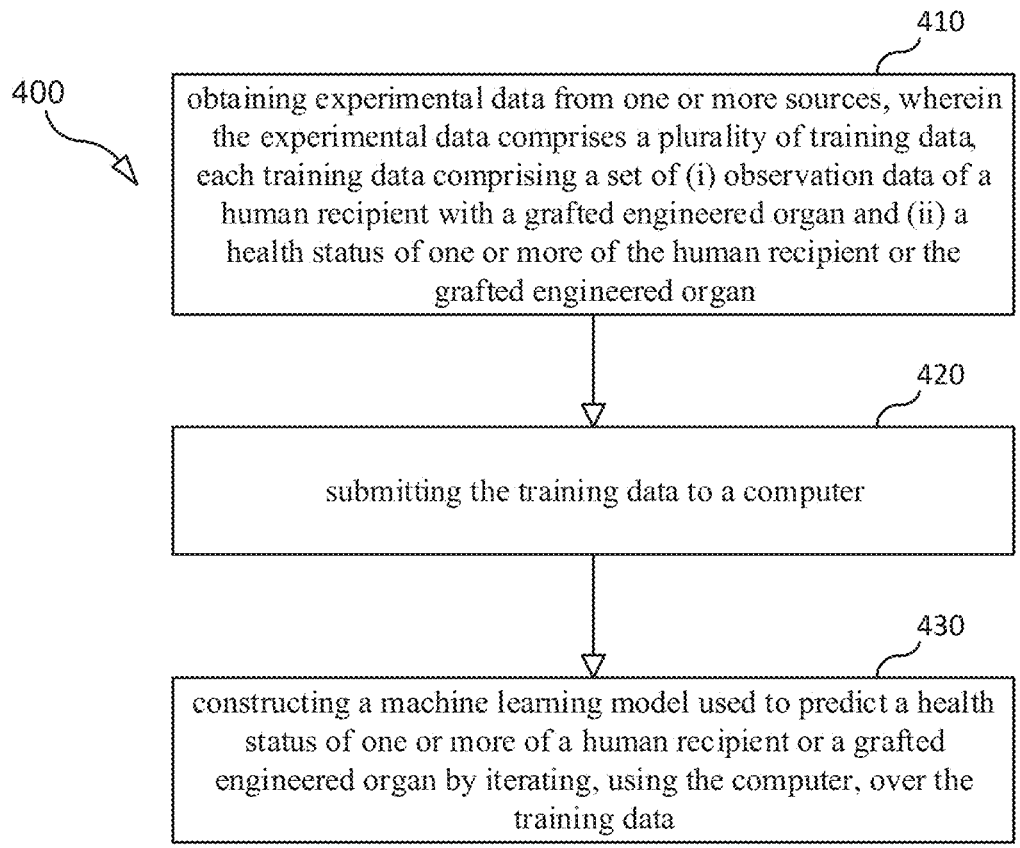
FIG. 4 illustrates an exemplary flow chart according to some embodiments.

FIG. 4 illustrates an exemplary flow chart according to some embodiments. In some embodiments, method 400 is for prognostic monitoring of a grafted engineered cell, tissue, or organ from a non-human donor in a human recipient. The method includes step 410 of obtaining experimental data from one or more sources, wherein the experimental data comprises a plurality of training data, each training data comprising a set of (i) observation data of a human recipient with a grafted engineered cell, tissue, or organ and (ii) a health status of one or more of the human recipients or the grafted engineered cell, tissue, or organ. The method includes step 420 of submitting the training data to a computer. The method includes step 430 of constructing a machine learning model used to predict a health status of one or more of a human recipient or a grafted engineered cell, tissue, or organ by iterating, using the computer, over the training data.

The embodiments disclosed herein may be used to predict and build an inventory of genetically engineered swine candidates suitable for xenotransplantation procedures for humans. For example, a human HLA/MHC identified through the processes described herein and applicable to a group of human recipients may be utilized as a template to modify the swine leukocyte antigen (SLA)/MHC sequence to match, e.g., to have 90%, 95%, 98%, 99%, or 100% sequence homology to a known human HLA/MHC sequence. Upon identifying a known human recipient HLA/MHC sequence to be used or performing genetic sequencing of a human recipient to obtain HLA/MHC sequences, a suitable biologically reprogrammed swine may be selected for use in a known human recipient. The reprogramming of the SLA/MHC to express specifically selected human MHC alleles, when applied to swine cells, tissues, and organs for purposes of xenotransplantation, and the selection of a suitable porcine donor using the techniques disclosed herein will decrease rejection.

Figure 5:
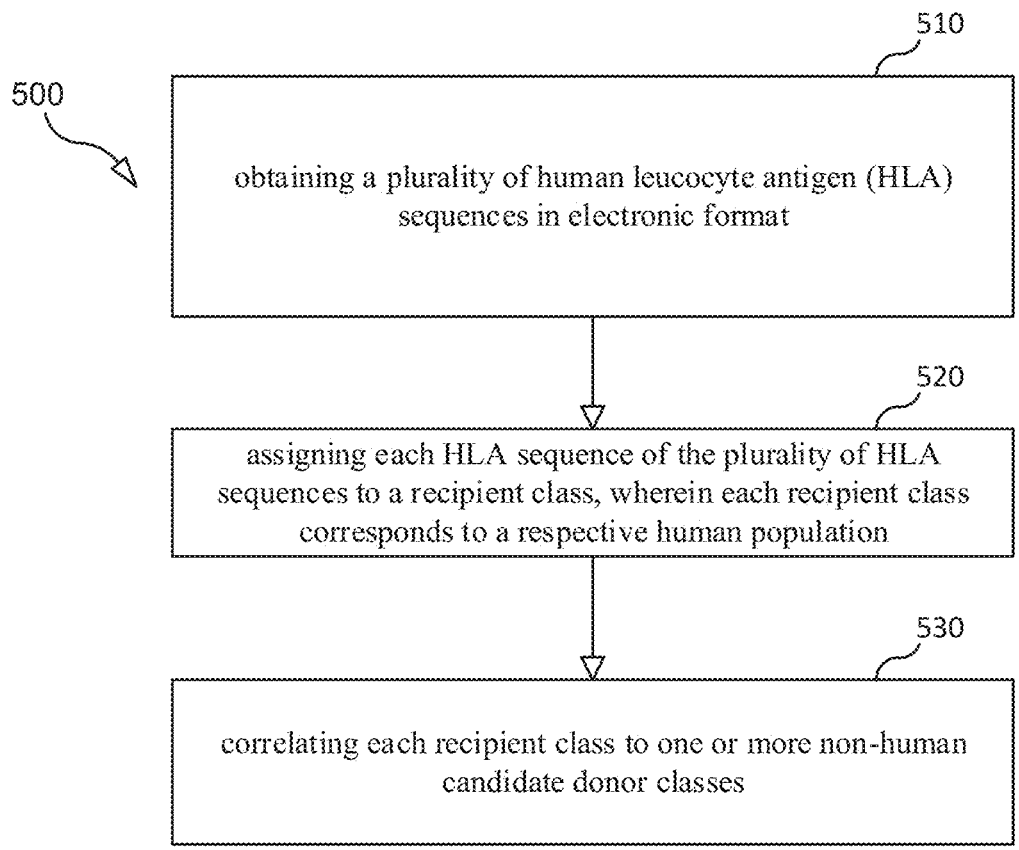
FIG. 5 illustrates an exemplary flow chart according to some embodiments.

FIG. 5 illustrates an exemplary flow chart according to some embodiments. According to some embodiments, method 500 is for identifying classes of non-human candidate donor organ or tissue samples suitable for xenotransplantation into a human. Method 500 includes step 510 of obtaining a plurality of human leucocyte antigen (HLA) sequences in electronic format. Method 500 includes step 520 of assigning each HLA sequence of the plurality of HLA sequences to a recipient class, wherein each recipient class corresponds to a respective human population. Method 500 includes step 530 of correlating each recipient class to one or more non-human candidate donor classes.

Figure 6:
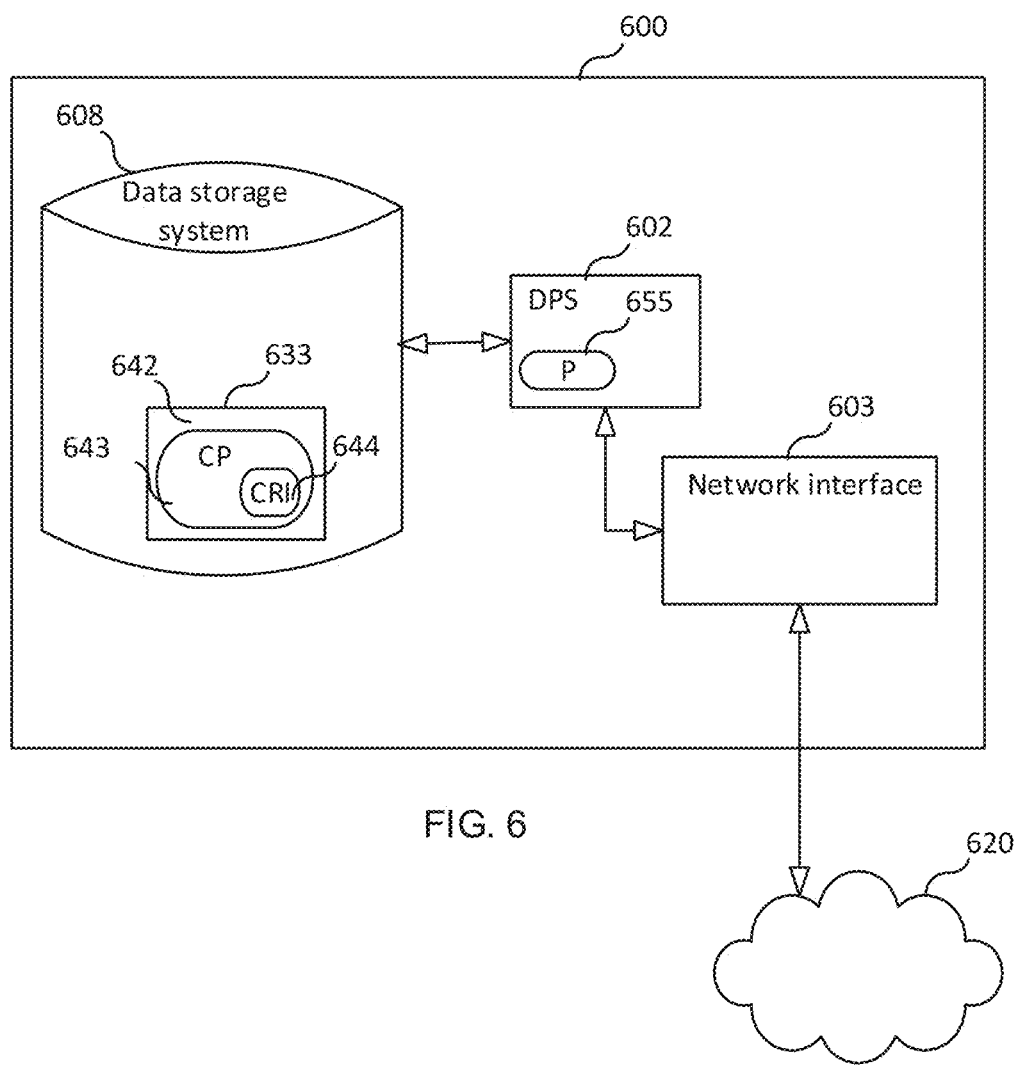
FIG. 6 is a block diagram of a computer system according to some embodiments.

FIG. 6 is a block diagram illustrating a computer system according to some embodiments. As shown in FIG. 6, computer system 600 may comprise: a data processing system (DPS) 602, which may include one or more processors 655 (e.g., a general purpose microprocessor and/or one or more other data processing circuits, such as an application specific integrated circuit (ASIC), field-programmable gate arrays (FPGAs), and the like); a network interface 603 for use in connecting device 600 to network 620 (e.g., any local or wide area network, cellular or packet switched network and the like); and local storage unit (a.k.a., "data storage system") 608, which may include one or more non-volatile storage devices and/or one or more volatile storage devices (e.g., random access memory (RAM)). In embodiments where device 600 includes a general-purpose microprocessor, a computer program product (CPP) 633 may be provided. CPP 633 includes a computer readable medium (CRM) 642 storing a computer program (CP) 643 comprising computer readable instructions (CRI) 644. CRM 642 may be a non-transitory computer readable medium, such as, but not limited to, magnetic media (e.g., a hard disk), optical media (e.g., a DVD), memory devices (e.g., random access memory), and the like. In some embodiments, the CRI 644 of computer program 643 is configured such that when executed by data processing system 602, the CRI causes the device 600 to perform steps described herein (e.g., steps described above and with reference to the flow charts). In other embodiments, device 600 may be configured to perform steps described herein without the need for code. That is, for example, data processing system 602 may consist merely of one or more ASICs. Hence, the features of the embodiments described herein may be implemented in hardware and/or software. The processor(s) may communicate with external networks 620 via one or more communications interfaces 603, such as a network interface card, WiFi transceiver, etc.

Embodiments of the disclosure are not limited to this representative architecture. Alternative embodiments may employ different arrangements and types of components, e.g., separate buses for input-output components and memory subsystems. Those skilled in the art will understand that some or all of the elements of embodiments of the disclosure, and their accompanying operations, may be implemented wholly or partially by one or more computer systems including one or more processors and one or more memory systems like those of computer system. In particular, the elements of the system and any robotics and other automated systems or devices described herein may be computer-implemented. Some elements and functionality may be implemented locally and others may be implemented in a distributed fashion over a network through different servers, e.g., in client-server fashion, for example. In particular, server-side operations may be made available to multiple clients in a software as a service (SaaS) fashion.

The term component in this context refers broadly to software, hardware, or firmware (or any combination thereof) component. Components are typically functional components that can generate useful data or other output using specified input(s). A component may or may not be self-contained. An application program (also called an "application") may include one or more components, or a component can include one or more application programs. Some embodiments include some, all, or none of the components along with other modules or application components. Still yet, various embodiments may incorporate two or more of these components into a single module and/or associate a portion of the functionality of one or more of these components with a different component.

The term "memory" can be any device or mechanism used for storing information. In accordance with some embodiments of the present disclosure, memory is intended to encompass any type of, but is not limited to: volatile memory, nonvolatile memory, and dynamic memory. For example, memory can be random access memory, memory storage devices, optical memory devices, magnetic media, floppy disks, magnetic tapes, hard drives, SIMMs, SDRAM, DIMMs, RDRAM, DDR RAM, SODIMMS, erasable programmable read-only memories (EPROMs), electrically erasable programmable read-only memories (EEPROMs), compact disks, DVDs, and/or the like. In accordance with some embodiments, memory may include one or more disk drives, flash drives, databases, local cache memories, processor cache memories, relational databases, flat databases, servers, cloud-based platforms, and/or the like. In addition, those of ordinary skill in the art will appreciate many additional devices and techniques for storing information that can be used as memory.

Memory may be used to store instructions for running one or more applications or modules on a processor. For example, memory could be used in some embodiments to house all or some of the instructions needed to execute the functionality of one or more of the modules and or applications disclosed in this application.

Figure 7:
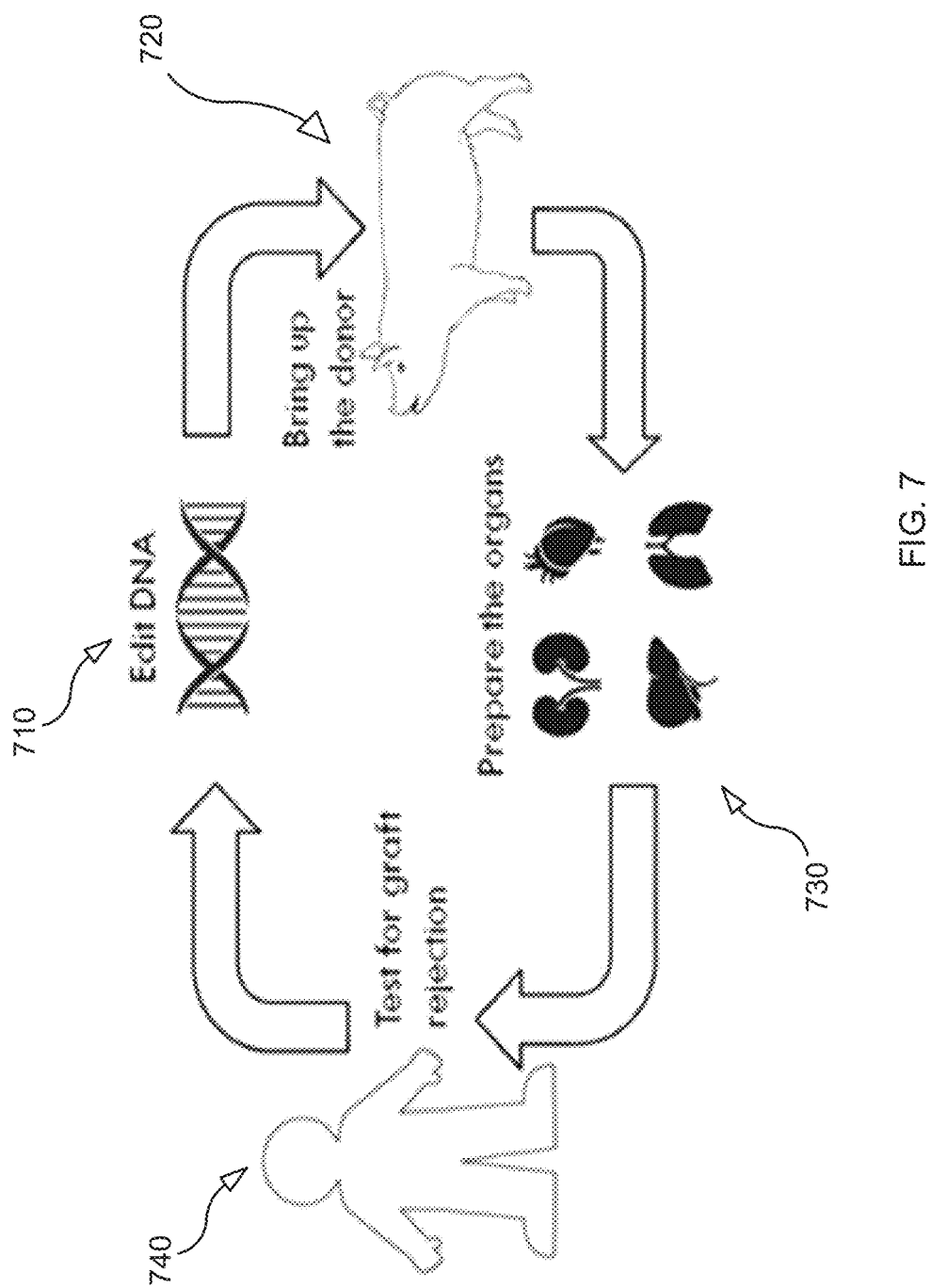
FIG. 7 is a flow diagram illustrating the typical research and development process in xenotransplantation, according to some embodiments.

FIG. 7 is a flow diagram illustrating typical research and development process in xenotransplantation, according to some embodiments. Transplantation research and Xenotransplantation in particular produce enormous amounts of experimental data. Interaction between graft cells and the host immune system is complex, depends on a multitude of parameters, and often not clearly understood by researchers. Optimization of this multitude of parameters is required in order to achieve a sustained function of grafted cells, tissues, and organs. However, finding the optimal or even sufficient sub-optimal solution by testing one hypothesis at a time is unfeasible. For instance, human Leukocyte Antigen (HLA) and related genes have 27980 know allelic variations. There is no doubt that more variations will be discovered with the proliferation of genome sequencing and genotyping programs involving more human samples from different populations. Swine homologs of HLA (SLA) have a similar number of variations. Some of these variants are synonymous (in this context have no effect on the outcome of transplantation) while others have a measurable effect on the outcome. The effect of different combinations of variants in HLA and SLA is largely unknown. The number of possible combinations of allelic variants in two genomes has an astronomical scale.

As shown in FIG. 7, a typical research project in xenotransplantation investigates one or a few variations of parameters (genes and alleles involved, immunosuppressant regiment, age and breed of donors, knock-out of certain genes and transgenic introduction of a few other genes, etc.) centered around a hypothesis based on a partial understanding of the biology of tissue rejection. The typical research project includes editing DNA (710), raising a donor (720), preparing the organs (730), and testing for graft or sample rejection (740) in a human subject. However, this approach has a very limited capacity for testing the multitude of combinations of parameters. There may be small sample sizes, high dimensionally data, lack of labeled data, and a long and expensive validation cycle. In the case of positive results, this approach makes no distinction between limited incremental improvement and sub-optimal instances of true success. Likewise, in the case of negative results, it is difficult to tell a dead end in research from a suboptimal instance of a promising result. High cost leads to low replicates in xenotransplantation experiments, which further limits the ability to find correct combinations of parameters leading to the next radical improvement.

These problems may be addressed by the introduction of Artificial Intelligence as an imminent part of the research, development, and application of xenotransplantation technology. In response to the challenges of complex voluminous data and the tedious process of research, the AI system leverages AI in a manner that mitigates complexity and guides the process of research, development, and application of xenotransplantation technology.

Figure 8:
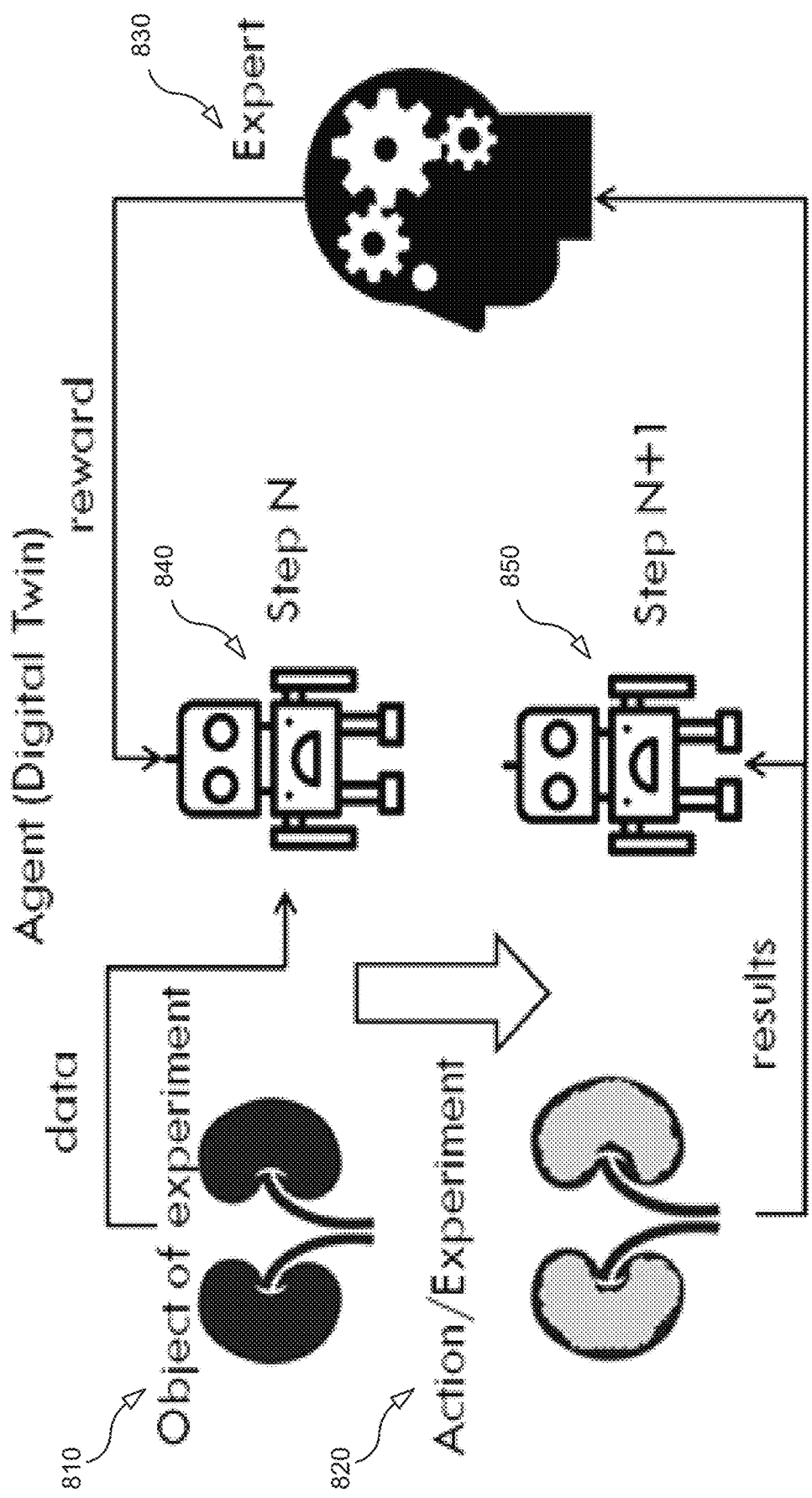
FIG. 8 is a block diagram illustrating aspects of an AI system, according to some embodiments.

FIG. 8 is a block diagram illustrating aspects of an AI system, according to some embodiments. The AI system may use a learning agent (Digital Twin, DT), multiple data collected in research and in process of technology application, and a reward system supervised by experts in Xenotransplantation. The learning agent or Digital Twin (DT) (840, 850) is trained iteratively on the available data from various experiments (810, 820) relevant to xenotransplantation. After initial training, the DT predicts its own next state given the starting state (measurable experimental conditions) and experience from training. The expert (830) estimates the difference between the observed experiment outcome and the predicted next state of DT and provides the reward for DT. The reward can be a number or a tensor characterizing the performance of DT. Iterative learning aims to maximize the reward, improving performance from iteration to iteration. The practical application of DT for the prediction can start when the prediction of the next state becomes sufficiently good. Training of DT can continue after the start of practical application.

RL and DT technology can be applied to multiple levels, including but not limited to DT models of a) the standard donor population with individual germline and somatic variation predicting the degree of success in editing; b) the model of genetically engineered donor genome predicting vitality, growth, reproduction, resistance to infections, immunoreactivity to human blood serum and other parameters important for xenotransplantation; c) the organ prepared, conditioned, and transplanted into the recipient; d) the recipient of xenograft.

In a single instance of DT, the data passed to the DT model characterizes the initial state of the system. For instance, donor genomes can be characterized by complete or partial genome sequence, exome sequence, list of allelic variants in a multitude of loci, phenotype traits, etc. Same or similar (completely or partially overlapping) data can be measured in a contrast state. A contrast state can signify a class label (such as "suitable for gene engineering" and "unsuitable") or the status before and after an action ("before gene editing" and "after gene editing", "before transplantation" and "after transplantation", etc.). The results passed to the expert to characterize the outcome of action or experiment and may include biomarkers, measured quantitative traits, test outcomes, etc. The reward passed from the expert to the DT can be a single or value or multiple values, arranged in a certain order, or an unsorted set of values that characterize the model behavior. In a simple case, it can estimate the difference between the prediction and observed results of the experiment, such as the difference between the number of days of graft survival in prediction vs. real-life experiment. However, the reward can also be multi-dimensional and include many characteristics in early, mid-term, and long-term success in actions and experiments.

Figure 9:
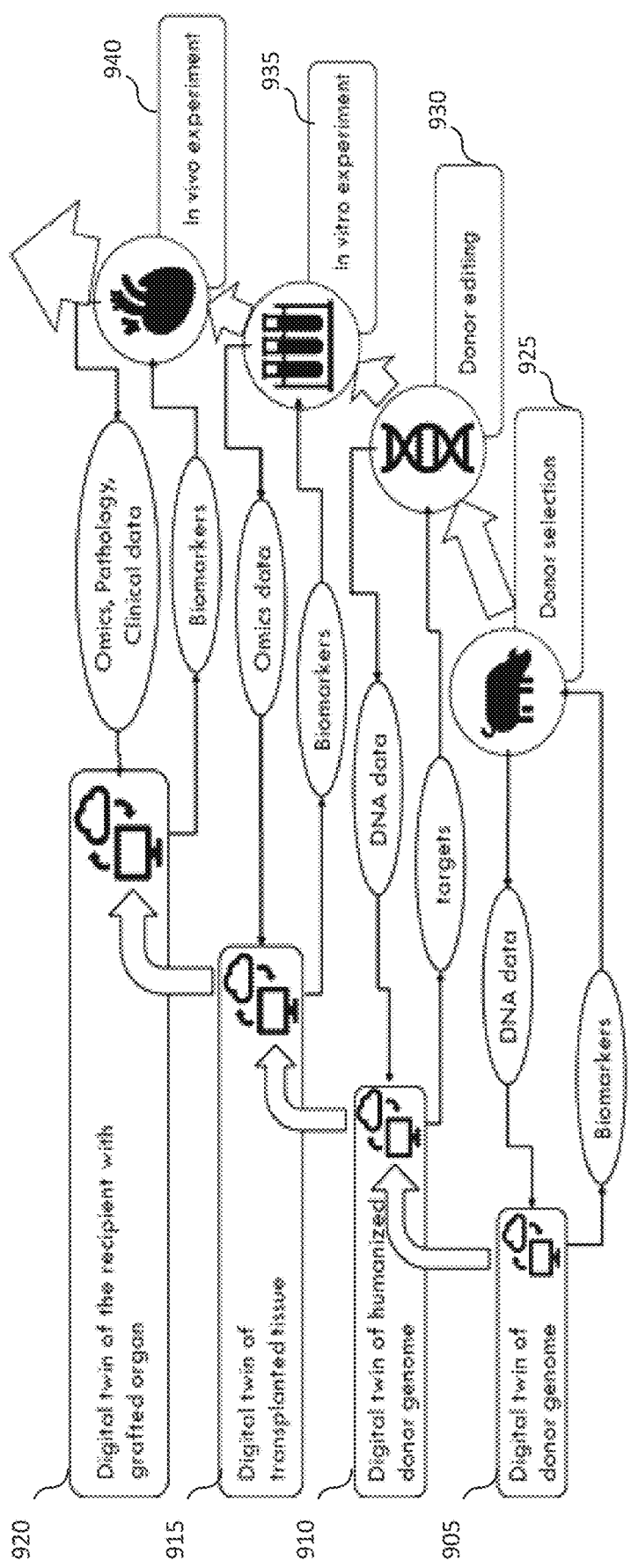
FIG. 9 is a block diagram illustrating aspects of an AI system, according to some embodiments.

FIG. 9 is a block diagram illustrating aspects of an AI system, according to some embodiments. As illustrated in FIG. 9, multiple DT can be joined in a larger system organized hierarchically so that the results of DT training on the earlier stage of development can be used on the next stage and the entire set of DT models can be trained and adjusted for the best overall result. The system may include a digital twin of the recipient with the grafted organ (920), a digital twin of transplanted tissue (915), a digital twin of humanized donor genome (910), and a digital twin of donor genome (905). The results from the AI system may be used to inform donor selection (925), donor editing (930), in vitro experiments (935), and in vivo experiments (940).

Several example applications of the AI system are described below. Specific details, parameters, and types of data may vary as well as the number of instances of implementation of this technology required to complete the development of xenotransplantation technology and/or performing an act of xenotransplantation.

Example 1: DT of Donor Substrate Population

Multiple experiments indicate that different alleles of MHC genes (HLA) are associated with different speeds and intensities of immune response to xenograft. Likewise, variations in MHC genes of porcine donor (SLA) also evoke different immune response upon xenotransplantation. Currently, there are 28,786 HLA and related alleles described by the HLA nomenclature and included in the IPD-IMGT/HLA Database. Considering the similarity and size, structure, and function of human and porcine genomes, the number of allelic variations in the swine genome is similar to the number of allelic variations in the human genome. The number of possible pair combinations of porcine graft and human recipient variations is huge, even considering only variations found within one breed selected for graft engineering. Although different combinations of alleles in graft and recipient genomes may result in different immune responses, it may be impossible to predict the outcome even if a complete sequence of the donor and recipient genomes are available.

At the start of the experiments, the population of potential donors may be genotyped by either complete or targeted sequencing of the SLA region or targeted hybridization of certain loci on microarray targets or multiple PCR analysis. The resulting data will characterize specific allelic variants present in the donor genome. Likewise, a recipient may be genotyped. The immunogenic potential of the range of potential donors will be estimated by in-vitro panels including at least one of the arrays interrogating antibody titer variations, the abundance of IL-2, IFN-g, or other cytokines, PBMC activation assay, T cell activation/proliferation assay, DCT assay, MAPPS assay, etc. The specific list of assays may vary so long the assays collectively produce a vector of quantitative measures characterizing the immune response of donor vs. graft tissues and/or graft vs. donor tissues. Genome sequencing data, proteome data, metabolome data, and in situ hybridization imaging data can be used in addition or instead of immunoreactivity data.

The deep learning model (or DT) of the donor genome that predicts the outcome (multi-dimensional quantitative characterization of success) of genome engineering and/or the outcome of xenotransplantation (estimated by the immunogenicity tests) using quantitative characteristics of the donor genome (genotype and phenotype) may be provided as input data. The model may be initially trained using the data existing at the time. All additional experiments producing genotype information and corresponding editing and immunogenicity test outcomes will add to DT training. The model (DT) is constantly re-trained until we achieve a consistently correct prediction of the outcome based on the measurable traits of the organ donor.

Example 2. DT of the Donor Genome

There are multiple ways to approach genome editing for xenotransplantation. The starting point is one of the variations in the swine genome associated is a common breed and additional gene knockouts. The next steps require editing certain stretches of the porcine genome to insert a fragment of human DNA sequence replacing the original porcine DNA. This process may target a variety of genes. Within those genes, different loci can be targeted. All targets may differ by direct effect (the phenotype with the certain level of expression for the edited gene and the certain level of affinity of the edited expressed gene to the receptors on the cell surface that bind this gene product and affect the immune function). Targets may also be different in indirect effects, such as the risk of off-target gene modification, the severity of the off-target editing for the phenotype, a potential gain of function effects (such as humanized gene inadvertently acquiring the ability to bind some porcine peptides), or loss of function (unintended loss of a secondary function with a reduced capacity of the humanized gene product to bind certain molecules in a swine cell), etc. In order to develop the optimal donor genome for further personalization and graft engineering, we design a series of experiments. Each of these experiments tests a specific hypothesis relevant to editing a certain part of the porcine genome and producing the array of data describing the outcome.

Such data may be used for the initial training of the DT model for the porcine genome with input describing the experiment parameters (such as the locus, the target site, gene editing protocol, chemical suppliers, etc.) and the outcomes (data set characterizing the resulting pig vitality, the penetrance of genetic traits, genome integrity, immunoreactivity, etc.). The DT model will be able to predict the outcome of the selection of certain loci in combination with targeted sequences and other technical details in the context of certain genetic variations among the donor pigs population. The knowledge accumulated in DT will be updated with each consequent experiment, gradually improving the model.

Example 3. DT of the Donor Organ

The DT in this case models the function of the cell, tissue, or organ engineered and grown for xenotransplantation. The goal of this DT is to predict the immediate outcome of xenotransplantation based on the data available at the time when transplantation is required. The data for such prediction may be collected in experiments involving biopsies of the donor organ, pathology analysis of the samples of the organ and bodily fluids, transcriptome, somatic genome, metabolome, the proteome of samples relevant to the state of donor organs in a multitude of prospective donors. The data may also include characteristics of the health state of the recipient, status of the immune system, metabolic homeostasis, and other physiology and biochemistry parameters. After initial training, the DT will predict the immediate outcome of xenotransplantation such as the intensity and type of rejection, vascularization, functionality, etc. Each additional experiment will add to the knowledge of the DT and help to improve the outcome by selecting the best donor available. The DT will also recommend additional steps and alternations in parameters (such as medications for the patient and for the donor, donor organ treatment, other conditions for transplantation) in order to improve the operation outcome if the best match is not perfect.

Example 4. DT of the Graft

The goal of this DT may be to predict the state and function of the graft in a long term based on continuous monitoring. The DT may also recommend the course of action (medication, operation, additional tests, etc.) to improve the state of the graft or the knowledge about such a state. The data collected in monitoring may include biopsies, liquid biopsies, genome and transcriptome sequences of samples containing graft material, proteomics and metabolomics analysis of samples, assays of circulating cell-free DNA, chemical signals in blood, visual markers, etc. The outcomes may include the state of graft and recipient at certain timepoints estimated by pathology analysis, medical observation, laboratory analysis of bodily fluids, etc. After initial training, the DT will predict the graft condition at the next time point based on available data characterizing the history and current state of the graft. The DT will also predict the overall trajectory of vital parameters over time. All the following experiments will add to DT training through reinforcement learning.

Figure 10:
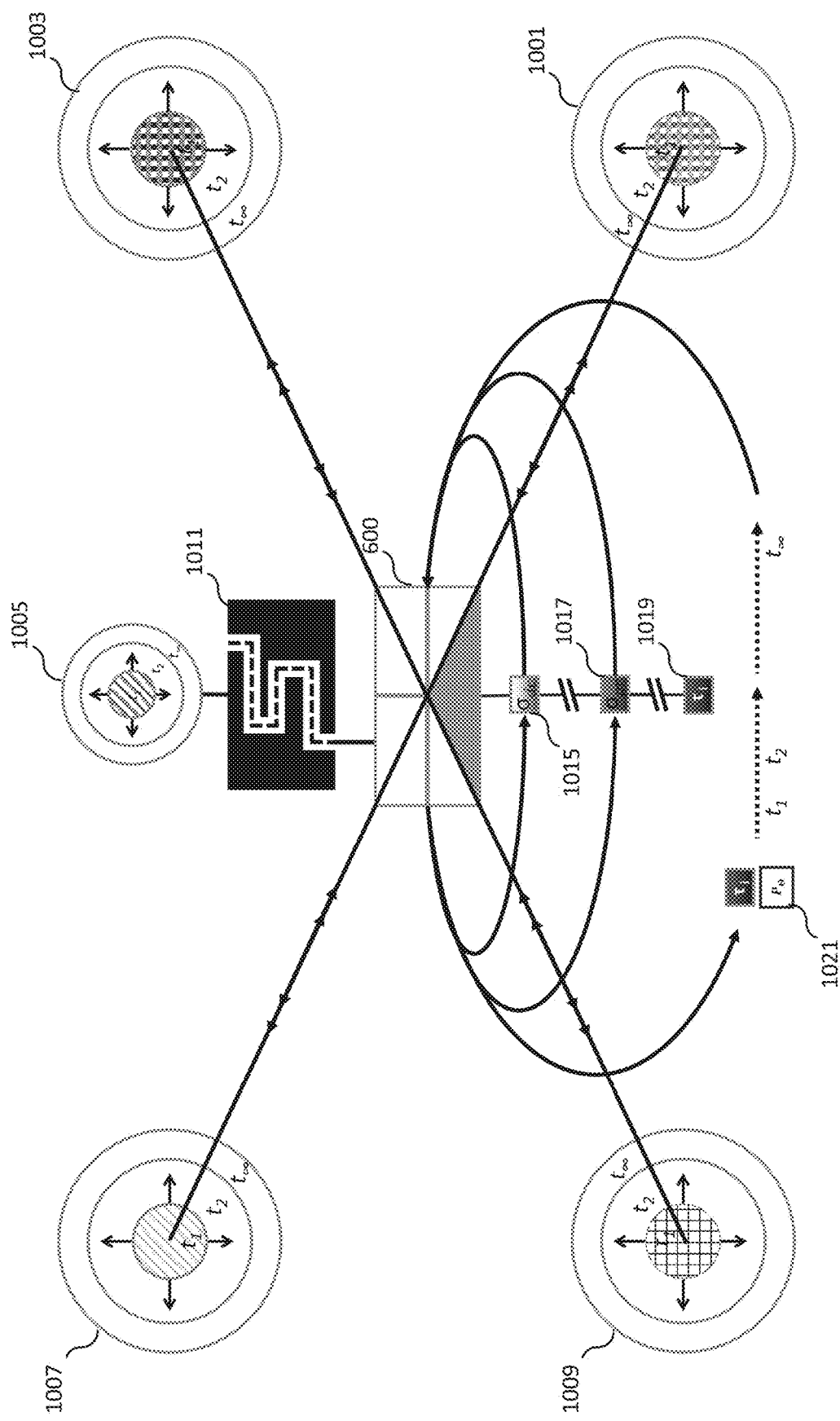
FIG. 10 illustrates a block diagram according to some embodiments.

FIG. 10 illustrates a block diagram according to some embodiments. FIG. 10 illustrates an AI platform 600, according to some embodiments. AI platform 600 may be in electronic communication with a plurality of libraries 1001, 1003, 1005, 1007, 1009, and 1011.

According to some embodiments, library 1001 is one or more protein variant libraries comprising naturally occurring proteins or proteins derived using recombination-based diversity generation mechanisms.

According to some embodiments, library 1003 is one or more genomic, proteomic, and research data libraries specific to non-humans, including non-human vertebrates.

According to some embodiments, library 1005 is one or more custom libraries comprising user data specific to a single human patient or patient population.

According to some embodiments, library 1007 is a genomic, proteomic, and research data library specific to humans.

According to some embodiments, library 1009 is a genomic, proteomic, and research data library specific to known pathogens and diseases.

According to some embodiments, library 1011 is one or more libraries of known therapeutic modalities from which a design basis of a candidate cell, tissue, or organ therapy (e.g., a sample) is selected.)

Illustrative types and sources of data input and libraries are described below, although additional, or different libraries may be used as would be understood by a person of ordinary skill.

Electronic structural libraries contain files and interactive models that can be used to model protein structures in varying dimensions up to the three-dimensional folding of a protein. The majority of them contain FASTA files which contain cDNA, ncRNA, and proteins. Most also give overviews on each gene and their subsequent protein such as their use in the organism and the mechanism of function.

In addition to the raw information, many tools allow for comparison of multiple sequences and prediction of binding affinity, proteasome cleavage sites, and other functionally relevant data.

Illustrative Genomic, Proteomic, and Research Data Specific Human Vertebrates (Library 1007)

1) HLA Alleles (hla.alleles.org/nomenclature/index.html)
  a) This website provides an allele and gene sequence database for *Homo sapiens*, specifically those of the Major Histocompatibility Complex. It provides a comprehensive list of its alleles and the specific sequences associated with each.
2) HLAMatchmaker (epitopes.net/)
  a) Can be used to predict immunogenicity of certain alleles with others given a single allele bead (SAB) assay has been run on the allele in question.
3) MotifScan (hiv.lanl.gov/content/immunology/motif_scan/motif_scan)
  a) Sequence motif database of Class I and II HLA proteins and their supertypes.
4) SYFPEITHI (syfpeithi.de/)
  a) Database of MHC ligands and peptide motifs for HLA Class I and II. This tool also contains a prediction tool for MHC specificity. Run by Eberhard Karls University of Tubingen.
5) nHLApred (imtech.res.in/raghava/nhlapred/)
  a) nHLApred is MHC Class I proteasomal cleavage predictor. It combines the use of artificial neural networks and quantitative matrices and also filters MHC predictions to potential cytotoxic T lymphocyte epitopes.
6) NIH Roadmap Epigenomics Mapping Consortium (egg2.wustl.edu/roadmap/web_portal/)
  a) Public resource and database for the human epigenomic data. This maps epigenetic features such as DNA methylation, chromatin accessibility, and histone modifications. It includes 111 consolidated epigenomes from the Roadmap Epigenomics Project and 16 epigenomes from The Encyclopedia of DNA Elements (ENCODE) project.

Genomic, Proteomic, and Research Data Specific to Vertebrates

1) Uniprot (uniprot.org/)
  b) Uniprot is an open source database which provides interactive three dimensional structure of proteins as well as the location of amino acids in that structure. Its combination of functional and sequencing data make it a powerful tool for protein prediction and understanding necessary for genome editing. It also provides information on specific genes and their function in the organism.
2) Ensembl (useast.ensembl.org/index.html)
  a) Ensembl is a database for full genome sequencing of individual and reference organisms. Gene annotations and structure such as exon and intron length and spliceosome location information are also available. Started by the European Bioinformatics Institute, an organization originally created to compete with the Human Genome Project, this is meant to provide a central hub for genome information
3) Rosetta (rosettacommons.org/software)
  a) Rosetta is the most prominent and well known protein modeling software. It not only models proteins but can be used for predictive structural and functional analysis of molecules including immunogenicity and ligand interaction and even enzyme design.
4) GenBank (ncbi.nlm.nih.gov/genome/)
  a) The National Center for Biotechnology Information (NCBI) provides this open source database which contains nucleotide and amino acid sequences for various genes from over 100,000 distinct organisms. This database is an amalgamation of all publicly available sequences from labs all over the world.
5) DNA Data Bank of Japan (DDBJ) (gggenome.dbcls.jp/)
  a) Data bank for human genomes sourced from the National Institute of Genetics in Japan, a member of the International Nucleotide Sequence Database Collaboration. Along with GenBank and the EMBL these three databases share information on a daily basis creating redundancies.
6) UCSC Genome Browser
  a) The UCSC Genome Browser provides access to genome sequencing data for various organisms and reference sequences. However, it is most useful for alignment and comparison of different organisms.
7) European Molecular Biology Laboratory (EMBL) (ebi.ac.uk/)
  a) Provides general information on genes such as length, location, and regulatory factors. Specific sequences and alignments can be found in Ensembl links. Diseases associated with variations as well as their main function information can also be found here. Ribbon structures screenshots of proteins can also be found linked here to the Protein Data Bank in Europe (PDBe).
  b) EMData Research from the same people provides three dimensional electron microscopy (3DEM) structure data. It provides PDB files for download.

8) Protein Data Bank in Europe (PDBe) (ebi.ac.uk/pdbe/)
   a) From the EMBL institution, this is an offshoot that provides three dimensional information for proteins such as assembly, chain, and molecular data.
9) Protein Data Bank (PDB) (rcsb.org/)
   a) The protein Data Bank is a database containing known three dimensional structures of proteins. Like UniProt they are completely interactive. Data comes from publications of specific molecules. Both nucleotide and amino acid sequences are also available. This database also provides a direct alignment to corresponding UniProt data.
10) Nucleic Acid Database (ndb) (ndbserver.rutgers.edu/)
    a) This database provides three dimensional structure information for nucleic acids. This is unique in that it focuses on single bases rather than whole genes. This allows for the visualization, sequencing, structure, and functional data for DNA types such as interstrand DNA crosslinks and complexes.
11) Annmap (bioconductor.org/packages/release/bioc/html/annmap.html)
    a) Annotation mapping for Affymetrix exon arrays specifically. It enables deep sequencing analysis of the database.
12) Vega (vega.archive.ensembl.org/index.html)
    a) Vega is similar to Ensembl. The difference, according to Vega's website, is that "Whereas Ensembl shows deep datasets (for example Variations and Regulatory Feature Predictions) and computationally derived gene predictions on a large number of whole genomesVega shows gene annotations arising from the labour intensive process of manual curation. This approach was applied to the whole of the human, mouse and zebrafish genomes. In addition, small regions of particular biological interest, for example the MHC regions of the gorilla, wallaby, pig and dog genomes were also annotated." As well as this Vega also allows for comparison of individuals within the same species.
13) EpiDOCK (ddg-pharmfac.net/epidock/EpiDock-Page.html)
    a) Structure based prediction of peptide MHC binding for Class II proteins.
14) Rankpep (imed.med.ucm.es/Tools/rankpep.html)
    a) Motif matrix to predict MHC Class I and II peptide binders using Position Specific Scoring Matrices. It can also be used to predict proteasomal cleavage.
15) BepiPred (cbs.dtu.dk/services/BepiPred/)
    a) Prediction of linear B cell epitopes utilizing machine learning.
16) ABCpred (crdd.osdd.net/raghava/abcpred/)
    a) ABCpred uses an artificial neural network to predict linear B cell epitopes in an antigen sequence. It cites an accuracy level of 65.93%.
17) LBtope (imtech.res.in/raghava/lbtope/)
    a) Prediction of linear B cell epitopes using servers available for antigen sequences, peptide sequences, and peptide mutants.
18) BCPREDS (ailab.ist.psu.edu/bcpred/)
    a) Uses physico-chemical properties of known B-cell epitopes to predict epitopes. Cites a 52.92% to 57.53% accuracy level.
19) SVMtrip (sysbio.unl.edu/SVMTriP/prediction.php)
    a) Tool that predicts protein surface regions that are preferentially recognized by antibodies from the University of Nebraska.
20) DiscoTope (tools.iedb.org/discotope/)
    a) Conformational B cell antibody epitope prediction utilizing surface accessibility and propensity amino acid score.
21) ElliPro (tools.iedb.org/ellipro/)
    a) Conformational B cell antibody epitope prediction based on geometrical properties.
22) BePro (pepito.proteomics.ics.uci.edu/)
    a) Discontinuous B cell epitope prediction using physicochemical properties and geometrical structure.
23) SEPPA (bio.tools/seppa)
    a) Spatial epitope prediction of protein antigens based on physicochemical properties and geometrical structure.
24) EPITOPIA (epitopia.tau.ac.il/)
    a) Structure-based method to detect immunogenic regions in protein structures or sequences using machine learning (naïve Bayes machine learning).
25) EPSVR (sysbio.unl.edu/EPSVR/)
    a) Structure-based antigen epitope prediction method method using a support vector regression model (machine learning).
26) EPIPRED (opig.stats.ox.ac.uk/webapps/newsabdab/sabpred/epipred/)
    a) Predicts epitopes based on a structure-based method (ASEP, Docking) using a specific antibody using machine learning.
27) Predicting Epitopes Using Antibody Sequence (PEASE) (ofranlab.org/PEASE)
    a) PEASE predicts an epitope for a given antigen structure and antibody sequence based on a structure-based method of machine learning.
28) MIMOX (i.uestc.edu.cn/mimox/)
    a) Phage display analysis using mimotope.
29) PEPITOPE (pepitope.tau.ac.il/)
    c) Epitope mapping using affinity-selected peptides using mimotope.
30) EpiSearch (curie.utmb.edu/episearch.html)
    a) Mapping of conformational epitopes using mimotope
31) Conformational B Cell Epitope Predict Ion (CBTOPE) (imtech.res.in/raghava/cbtope/submit.php)
    a) Sequence based prediction using a support vector machine (SVM) with an accuracy of more than 85% and Area under curve (AUC) 0.9.
32) MHCPred (ddg-pharmfac.net/mhcpred/MHCPred/)
    a) A quantitative structure-activity relationship model for MHC Class I and II proteins to predict binding affinity.
33) EpiTOP (pharmfac.net/EpiTOP)
    a) EpiTOP is a quantitative structure-activity relationship model tool used to predict MHC Class II binding affinity.
34) Propred (crdd.osdd.net/raghava/propred/)
    a) Quantitative affinity matrix for Class II MHC binding affinity, binding region, and supertype prediction.
35) Propred-1 (crdd.osdd.net/raghava/propred1/)
    a) Quantitative affinity matrix to predict MHC Class I binding affinity, binding regions, supertype, and proteasomal cleavage.
36) EpiJen (ddg-pharmfac.net/epijen/EpiJen/EpiJen.htm)
    a) Quantitative affinity matrix model to predict Class I MHC binding affinity, TAP binding, and proteasomal cleavage.
37) IEDB-MHCI (tools.immuneepitope.org/mhci/)
    a) MHC Class I MHC binding affinity prediction using either an artificial neural network or a quantitative affinity matrix. Whichever is more appropriate for the specific MHC molecule being analyzed.

38) IEDB-MHCII (tools.immuneepitope.org/mhcii/)
  a) Utilizes one of two methods of prediction depending on which is better suited (either an artificial neural network or a quantitative affinity matrix) to predict MHC Class II binding affinity
39) IL4pred (webs.iiitd.edu.in/raghava/il4pred/index.php)
  a) Predicts MHC Class II antigenic regions using a support vector machine method.
40) MHC2PRED (imtech.res.in/raghava/mhc2pred/index.html)
  a) This is a support vector machine based method of prediction for MHC Class II molecules. It identifies promiscuous MHC class II binders.
41) NetMHC (cbs.dtu.dk/services/NetMHC/)
  a) NetMHC is an artificial neural network from the Department of Health Technology which provides Class I MHC binding affinity predictions. It encompasses 81 different alleles and 41 additional species.
42) NetMHCII (cbs.dtu.dk/services/NetMHCII/)
  a) An artificial neural network for predicting Class II MHC binding affinity for HLA-Dr, -DQ, and -DP.
43) NetMHCpan (cbs.dtu.dk/services/NetMHCpan/)
  a) NetMHCpan is an artificial neural network which predicts peptide binding affinity to MHC Class I molecules.
44) NetMHCIIpan (cbs.dtu.dk/services/NetMHCIIpan/)
  a) This serves as the Class II counterpart to NetMHCpan and is also an artificial neural network for predicting binding affinity.
45) NetCTL (cbs.dtu.dk/services/NetCTL/)
  a) Predicts Cytotoxic T Lymphocyte epitopes in protein sequences using artificial neural networks. More specifically, it predicts MHC Class I binding affinity, supertype, TAP binding, and proteasomal cleavage.

Illustrative Protein Variant Library Comprising Naturally Occurring Proteins or Proteins Derived Using Recombination-Based Diversity Generation Mechanisms, (1001).

Peptide binding libraries have been used in order to pick the correct cell-binding peptides. Of these libraries there are two types. The first, biological libraries contain, DNA which encodes for the peptide which is linked to the phenotype of said peptide. This is incorporated into the library's normal structure. There are various types of biological libraries but only phage and bacterial display have been used in the isolation of mammalian-cell-binding peptides.
  1) Phage Display
    a) A phage display library can contain up to $10^{11}$ different peptides which are all easily amplified and replicated. These libraries are commercially available and easily stored. They are inexpensive and maintained through standard laboratory procedures and peptide selection is rather essay. They typically only include natural, L-amino acids and simple structures and require two hosts.
  2) Bacterial Display
    a) Bacterial display libraries can be just as large as the phage display and are easily manipulated. Unlike the phage display, bacteria only requires one host and can be amplified without the need for reinfection. They also provide high throughput screening using fluorescence-activated cell sorting (FACS) and are more commercially available. Bacterial libraries are limited in that they can only be used for in vitro panning and screening studies.

Chemical Libraries are the second peptide binding library type. Unlike biologic libraries where the diversity is created at the DNA level, chemical libraries create diversity chemically by using a collection of monomers. These either are expressed on a bead, similar to how biologic libraries express peptides on bacteria or phages, or in pools of peptide libraries.
  1) Positional Scanning Synthetic Peptide Combinatorial Library (PS-SPCL)
    a) This method keeps peptides as their own entities that can be used in any assay as a solution. A single library of this type can have a large number of different peptides synthesized and is not limited to naturally occurring amino acids. However, these are not commercially available, and this library is built under the impression that each individual amino acid contributes to binding independently. In addition, more peptide synthesis and testing is required after the initial screening.
  2) One-Bead One-Compound (OBOC)
    a) This library type is limited to $10^8$ compounds, slightly smaller than Phage and Bacterial Displays. However, it can do L- and D-amino acids and even unnatural amino acids. In vitro or ex vivo peptide selection on whole cells is possible with this library and synthesis can be done using standard lab practices. Its versatility also leads to the potential for steric hindrance between cellular receptors and Biopeptide Libraries
  1) Structurally Annotated Therapeutic Peptides Database (SATPdb) (crdd.osdd.net/raghava/satpdb/links.php)
    a) SATPdb is a peptide database that compiles information from 20 different peptide databases and two data sets. It includes peptides such as ACPs, AVPs, ABPs, CPPs, toxic peptides, etc. It links to 87 Places for various peptide prediction and databases.
  2) StraPep (isyslab.info/StraPep/)
    a) StraPep is a database specifically for structural information of known bioactive peptides.
  3) APD/APD3 (aps.unmc.edu/AP/main.php)
    a) Database of AMPs and ACPs specifically meant for anti-cancer peptides.
  4) DADP (split4.pmfst.hr/dadp/)
    a) Database of defense peptides for anticancer research. This data base includes AMP and ACP peptides.
  5) DBAASP/DBAASP v.2 (dbaasp.org/home)
    a) Database of AMP, ACP and other anti-cancer peptides.
  6) DRAMP (dramp.cpu-bioinfor.org/)
    a) AMP, ACP, and ABP peptides and others of the like.
  7) CancerPPD (crdd.osdd.net/raghava/cancerppd/)
    a) Anticancer peptides and proteins database.
  8) LAMP (biotechlab.fudan.edu.cn/database/lamp/)
    a) AMP and ACP database.
  9) Quorumpeps (quorumpeps.ugent.be/)
    a) Database for signal peptides that are quorum-sensing managed by Ghent University.
  10) BIOPEP (uwm.edu.pl/biochemia/index.php/pl/biopep)
    a) Database for bioactive peptides and anti-hypertensive peptides.
  11) Immune Epitope Database and Analysis Resource (IEDB) (iedb.org/)
    a) IEDB is a National Institute of Allergy and Infectious Diseases (NIAID) funded database for antibody and T cell peptide data found experimentally. it compromises both humans and nonhuman primates as well as a number of other animal species. Specifically, T cell epitopes in autoimmunity, and transplantation are found here.

b) Utilizes the propensity scale method and includes tools for prediction and analysis of epitopes.
c) fluorescently labeled for quantitative and high throughput screening. It also does not have the same in vivo capabilities as Phage is limited to in vivo work.
b) peptides, and these are also not commercially available.

Illustrative Genomic, Proteomic, and Research Data Specific to Known Pathogens and Diseases (Library 1009).

1) Virus Pathogen Resource (viprbrc.org/brc/home.spg?decorator=vipr)
   a) Database of sequences, strains, immune epitopes, host factor data, 3D protein structures, antiviral drugs, and plasmid data for a number of different viruses. This database also comes with tools for sequence alignment, phylogenetic tree creators, sequence variation analysis, BLAST searches, and annotation abilities.
2) PEPVAC (imed.med.ucm.es/PEPVAC/)
   a) Motif matrix database for MHC Class I Supertype and Proteasomal cleavage analysis. It can perform alignment analysis, 3D modeling, sequence manipulation analysis, and similarity searches.
3) Epitope Vaccine Optimization Server (EPISOPT) (bio.med.ucm.es/episopt.html)
   a) Motif matrix for predicting MHC Class I binding profiles and supertype.
4) Vaxign (violinet.org/vaxign/)
   a) Vaxign is a vaccine design system that uses a motif matrix for MHC Class I and II prediction and analysis.
5) OmicsDB:Pathogens (biorxiv.org/content/10.1101/2020.03.18.979971v2.full)
   a) Database for functional networks of plant pathogens.
6) Kyoto Encyclopedia of Genes and Genomes (KEGG) Pathogen (genome.jp/kegg/genome/pathogen.html)
   a) This consists of genomes for pathogen and infectious disease as long as additional information on genes, pathways, and drug interactions.
7) Pathogen Research Database (lanl.gov/collaboration/pathogen-database/index.php)
   a) HIV database containing viral genetic sequences, drug resistance-associated mutations, and immunological epitopes.
   b) The HCV database for hepatitis C virus consists of a sequence database and an immunological epitope database. Both stem from the same platform that also allows for some analysis similar to the HIV database but more limited.
   c) HFV/Ebola Database provides Ebola-associated genetic and immunological data. Sequence alignment, genomic maps, T cell epitopes, and antibody binding sites can all be seen/done and additional functional data is also present.
8) Pathogen Variation Database (PVD) (db.cngb.org/pvd/)
   a) Includes only human pathogens sequence and biologic characteristic information split into three distinct databases.
      i) Chronic infectious disease pathogens database
      ii) Emerging infectious diseases pathogens database
      iii) Major infectious disease pathogens database
9) Mypathogen database (MPD) (data.mypathogen.org/pgdb/)
   a) Database consisting of bacterial genomics data. It shares microbial and meta genomes including over 6,000 genera and over 11,000 species.
10) National Microbial Pathogen Data Resource (NMPDR) (patricbrc.org/)
    a) NMPDR contains genomes of pathogenic bacteria and other genomes that provide comparative analysis context. It integrates public genomes with biological subsystems to create consistent genome annotations.
11) Pathogen Detection (ncbi-nlm-nih-gov.proxy1.library.jhu.edu/pathogens/)

Bacterial pathogen genomic sequences originating in food, the environment, and patient sources which allows identification of related sequences for food contamination tracing.

The libraries 1001, 1003, 1005, 1009, and 1011 may be updated over time, e.g., $t_0 \rightarrow t_\infty$, as knowledge grows over time. Information from the plurality of libraries may be ingested by the computer system 600, which may include one or more predictive machine learning models. Accordingly, high throughput genetic alteration libraries are coupled into an iterative process that is integrated with a sophisticated data analytics and machine learning process in order to create a dramatically different methodology for improving cell, tissue, or organ therapies. The platform 600 is therefore fundamentally different from the previously discussed traditional methods of developing cell, tissue, or organ therapies. The high throughput platform does not suffer from any of the drawbacks associated with the previous methods.

Platform 600 may include a predictive machine learning model, populated with a training data set(s) collected from the libraries. The predictive machine learning model may be a neural network having artificial intelligence capabilities that develops a sequence-activity for predicting a clinical relevance, therapeutic optimization, and xenotransplantation compatibility of the candidate cell, tissue, or organ therapy. The predictive machine learning model may predict genomic, nucleotide or proteomic, amino acid sequences to design a candidate cell, tissue, or organ therapy derived from the non-human donor with expected therapeutic performance parameters specific to a single human patient or patient population.

The sequence-activity model may predict clinical relevance. This may relate to, but is not limited by one or the following: 1. whether the candidate sample works for its intended purpose; 2. treats the disease (only) or has negative side-effects; 3. long-term benefit, such as treatment with levodopa vs neural transplant; and/or 4. extended life span or improved clinical outcome.

The sequence-activity model may predict a therapeutic optimization as a function of multiple independent variables. This may relate to, but is not limited by one or more the following: 1. number of cells required; 2. type of cell required; 3. cells, tissues, and/or organs required; 4. dosage regimen; 5. elimination or reduction in undesirable concomitant medications or therapies); or 6. xenotransplantation compatibility, as discussed above, of a candidate sample to be derived from the non-human donor.

According to some embodiments, the predictive machine learning model may use linear regression models to describe/characterize and rank-built (or rank-scored) sequences, which have various genetic perturbations introduced into their genomes from the various taught libraries. The linear regression model may be used to make performance predictions for sequences that haven't yet been built. Accordingly, the model may generate in silico all possible configurations of genetic changes and use a regression model to predict relative sequence performance and order the candidate sequence designs by performance. Thus, by utilizing the regression model to predict the performance of as-yet-unbuilt sequences, the method allows for the production of higher performing strains, while simultaneously conducting fewer experiments.

To construct a model to predict performance of as-yet-unbuilt sequences, the system 600 may initially produce a set of design candidates using design of experiments (DOE) techniques. This may be done by fixing the total number of genetic changes in the strain, and then defining all possible combinations of genetic changes. For example, one can set the total number of potential genetic changes/perturbations to a predetermined number X, and then decide to design all possible Y-member combinations of the X potential genetic changes, which will result in candidate sequence designs.

Using the linear regression with the combinatorial configurations as input, one can then predict the expected relative performance of each candidate design. Predictive accuracy should increase over time as new observations are used to iteratively retrain and refit the model. The quality of model predictions can be assessed through several methods, including a correlation coefficient indicating the strength of association between the predicted and observed values, or the root-mean-square error, which is a measure of the average model error. Using a chosen metric for model evaluation, the system may define rules for when the model should be retrained.

Accordingly, in some embodiments, the predictive machine learning model develops a sequence-activity model for predicting a clinical relevance, therapeutic optimization, or xenotransplantation compatibility of a candidate sample to be derived from the non-human donor, as a function of multiple independent variables. While the platform 600 may create linear regression predictions based on linear terms reflecting predicted candidate sample performance, such linear regression predictions can also be applied to other features such as saturation biomass, resistance, or other measurable features. Accordingly, non-linear features outside of predicted performance may be considered when evaluating a performance of candidates. In some embodiments, the multiple independent variables comprise a plurality of linear terms and one or more non-linear terms. In some embodiments, the non-linear term comprises a coefficient and two or more dummy independent variables. The coefficient may indicate a relative impact on an activity by an interaction of the two or more dummy independent variables. In some embodiments, each of the two or more dummy independent variables specifies a presence or absence of one residue or codon at a different sequence position of two or more sequence positions.

As aforementioned the present disclosure provides a novel high throughput platform and genetic alteration strategy for engineering cell, tissue, or organ therapies through an iterative systematic introduction and removal of genetic changes across design candidate sequences. The platform is supported by a suite of molecular tools which enables the creation of a high throughput genetic alteration library and allows for the efficient implementation of genetic alterations into a given therapy design candidate.

The high throughput genetic alteration libraries serve as sources of possible genetic alterations that may be introduced in a particular therapy design candidate background. In this way the high throughput genetic alteration libraries are repositories of genetic diversity, or collections of genetic alterations, which can be applied to the initial or further engineering of a given therapy design candidate. Techniques for programming genetic alterations for implementation to design candidates are described in U.S. non-provisional patent application Ser. No. 16/593,785, filed Oct. 4, 2019; Ser. No. 17/016,937, filed Sep. 10, 2020; Ser. No. 17/017,002, filed Sep. 10, 2020, Ser. No. 16/830,213, filed Mar. 25, 2020; Ser. No. 17/079,821, filed Oct. 26, 2020; Ser. No. 17/237,336, filed Apr. 22, 2021, which are incorporated herein by reference in their entireties.

The high throughput methods of the present disclosure also teach methods for directing the consolidation and combinatorial use of tool sets, including Epistasis mapping protocols. As aforementioned this suite of molecular tools either in isolation or in combination enables the creation of high throughput genetic alteration therapy candidate design sequence libraries.

Utilization of the aforementioned genetic alteration libraries in the context of taught high throughput engineering platform enables the identification and consolidation of beneficial causative mutations or gene sections and also the identification and removal of passive or detrimental mutations or gene sections. This new approach allows rapid improvements in design candidate performance that could not be achieved by traditional random mutagenesis or directed genetic engineering. The removal of genetic burden or the consolidation of beneficial changes into a design candidate with no genetic burden also provides a new, robust starting point for additional genetic alterations that may enable further improvements.

In some embodiments, the present disclosure teaches that as orthogonal beneficial changes are identified across various discrete branches of a therapy design candidate lineage, they also can be rapidly consolidated into better performing design candidates. These mutations can also be consolidated into cell, tissue, or organ therapies that are not part of the original mutagenic lineages, such as cell, tissue, or organ therapies with improvements gained by directed genetic engineering.

In some embodiments, the present disclosure differs from the known cell, tissue, or organ therapy approaches in that it analyzes the genome wide, combinatorial effect of mutations across multiple disparate genomic regions, including expressed and non-expressed genetic elements, and uses gathered information (i.e. experimental results) to further predict combinations expected to produce improved, enhanced phenotypic performance measures.

In some embodiments, the present disclosure teaches: i) methods and hardware for machine learning computational analysis and prediction of synergistic effects of genome-wide mutations, and ii) methods for high throughput engineering.

The following molecular tools and libraries are discussed in terms of illustrative examples. Persons having skill in the art will recognize that the molecular tools of the present disclosure are compatible with any cell, tissue, or organ therapy, including blank and blank.

Each of the identified molecular toolsets which enable the creation of various high throughput genetic alteration libraries utilized will now be discussed. The genetic alteration library can refer to the actual physical collection that is formed by this process, with each member sequence being representative of a given promoter operably linked to a particular gene, in an otherwise identical genetic background, said library being termed a "genomic alteration library." Furthermore, the library can refer to the collection of genetic alterations in this case a given gene X and a desired phenotype Y. The characterization of the design candidates in the genetic alteration library produces information and data that can be stored in any data storage construct including a relational database, an object-oriented database, or a highly distributed NoSQL database.

In summary, utilizing various genetic alterations to drive expression of various genes in an organism (cell, tissue, or organ therapy) is a very powerful tool to optimize a trait of interest. The molecular tool of genetic alteration uses minimally manipulated genetic alterations and has been demonstrated to vary expression of at least one locus under a certain condition.

This foundational process can be extended to provide further improvements in cell, tissue, or organ therapy performance by, inter alia: (1) consolidating multiple beneficial alterations into a single design candidate, either one at a time in an interactive process, or as multiple changes in a single step. Multiple alterations can be either a specific set of defined changes or a partly randomized, combinatorial library of changes; (2) feeding the performance data resulting from the individual and combinatorial generation of the library into an algorithm that uses the data to predict an optimum set of alterations based on the interaction of each alteration; and (3) implementing a combination of the above 2 approaches.

In some aspects, a diversity pool may be an original cell, tissue, or organ with a "baseline" or "reference" genetic sequence at a particular time point and then a number of subsequent offspring sequences that were derived from said baseline and that have a different genome in relation to the baseline genome of the first.

In some embodiment, genetic alterations are determined from a reference sequence or reference genome. In some embodiments this reference genome is a wild type genome. In other embodiments, the reference genome/sequence is a whole or part genome sequence (via NGS, Sanger, or other methods) prior to being subjected to any alteration. The reference genome can be defined by the practitioner and does not have to be an original wildtype genome or original industrial genome. The base genome is merely representative of what will be considered the "base," "reference," or original background by which subsequent alterations that were derived or were developed from said reference are to be compared.

At 1015, data from each of the analyzed design candidates is associated, or correlated, with a particular performance outcome and is recorded for future use. Thus, the present disclosure enables the creation of large and highly annotated high throughput genetic alteration libraries that are able to identify the effect of a given alteration on any number of genetic or phenotypic traits of interest. The information stored in these libraries informs the machine learning algorithms of the high throughput genomic engineering platform and directs future iterations of the process which ultimately needs to evolve designs that possess highly desirable properties and traits. According to some embodiments, $\sigma_{dc}$ is the deviation of the design candidates' performance parameters between those results from in silico model simulations versus computational, predicted outcomes, and where i=1 to ∞.

Thus, the epistasis mapping procedure provides a method for grouping and/or ranking a diversity of genetic alterations applied in one or more genetic backgrounds for efficient and effective consolidations of said mutations into one or more genetic backgrounds.

In aspects, consolidation is performed with the object of creating novel design candidate sequences which are optimized for the production of target cell, tissue, or organ therapies. Through the epistasis mapping procedure, it is possible to identify functional groupings of mutations, and such functional groupings enable a consolidation strategy that minimizes understandable effects.

At 1017, a subset of design candidates, e.g., top performing design candidates in silico, may be selected to create a subset of prototypes or design candidates for manufacture. Each design candidate for manufacture is a manufactured, prototype candidate cell, tissue, or organ therapy where $\sigma_{pr}$ is the deviation of the manufactured prototypes' performance parameters between those results from diagnostic testing results versus computational, predicted and in silico outcomes, and where i=1 to ∞.

At 1019, a subset of prototypes is then clinically developed $T_i$ for experimental trials and development, i.e. manufactured clinical-grade cell, tissue, or organ therapy.

At 1021, experimental data from the clinical trials may be obtained and iterated. A human patient or patient population is treated with the clinically developed $T_i$ sample, $P_\Theta$, where P refers to a unique human patient or patient population, and $\Theta$ is a unique, numerical identifier, where $\Theta$=1 to ∞.

The data from the in silico design candidate performance evaluation (1015), prototype performance evaluation (1017), and clinical evaluation (1019 and 1021) may iteratively feed back into the platform 600 and the predictive machine learning model in order to better train and improve the platform over time. In addition, data from platform 600 may be transmitted to libraries 1001, 1003, 1007, 1009, 1011, and 1005 to add to a shared knowledgebase over time.

Figure 11:
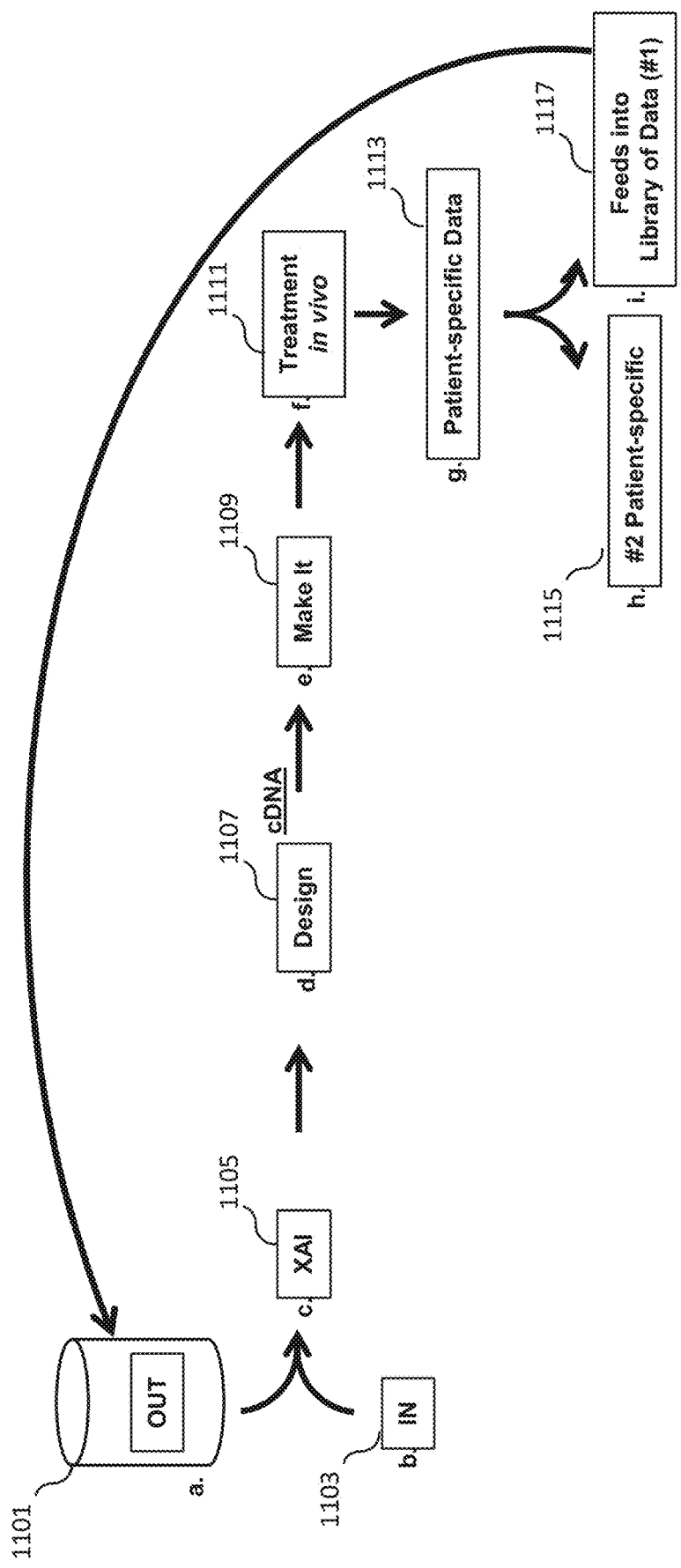
FIG. 11 illustrates an exemplary flow diagram according to some embodiments.

FIG. 11 illustrates an exemplary flow diagram according to some embodiments. At step 1103, data from one or more patients or patient populations is provided as input to computer system 600. The data may include, WGS, patient cytokines, allergies, medical history, diagnostics, and other clinically relevant information. In addition, at 1101, prior experimental data and output from the computer system 600 may be inputted to the computer system 600 as additional data for the predictive machine learning model.

At step 1105, the computer system, including the predictive machine learning model performs simulations using the input clinical and experimental or theoretical data from the libraries discussed above to arrive at one or more potential sequences for potential design candidates.

At step 1107, potential design candidates are modeled in silico based on the sequences to predict patient outcome if implemented and resulting in specific biomarkers. If the in silico performance indicates that the design candidate is not acceptable, the process iterates until a suitable design candidate is identified. If a suitable design candidate is identified, the process continues to step 1109.

At step 1109, a prototype is made using the techniques described herein regarding transcription, protein synthesis, and the like.

At step 1111, if the prototype satisfies one or more design parameters, a patient is treated in vivo using the prototype or a clinical grade sample made from the prototype.

At step 1113, patient specific data is collected, including empirical patient specific data, diagnostics, measured outcomes, etc. The system 600 may evaluate whether the predictive outcome from the in silico process matches the empirical outcome from the in vivo experiment, and the system may quantify and harness a delta or change in the predicted outcomes and use the library of knowledge to educate as to possible imperfections in the design. The outcomes at step 1115 may be provided as patient-specific data, and at 1117, may be provided or feed into a library of data that may be used for further design.

Figure 12:
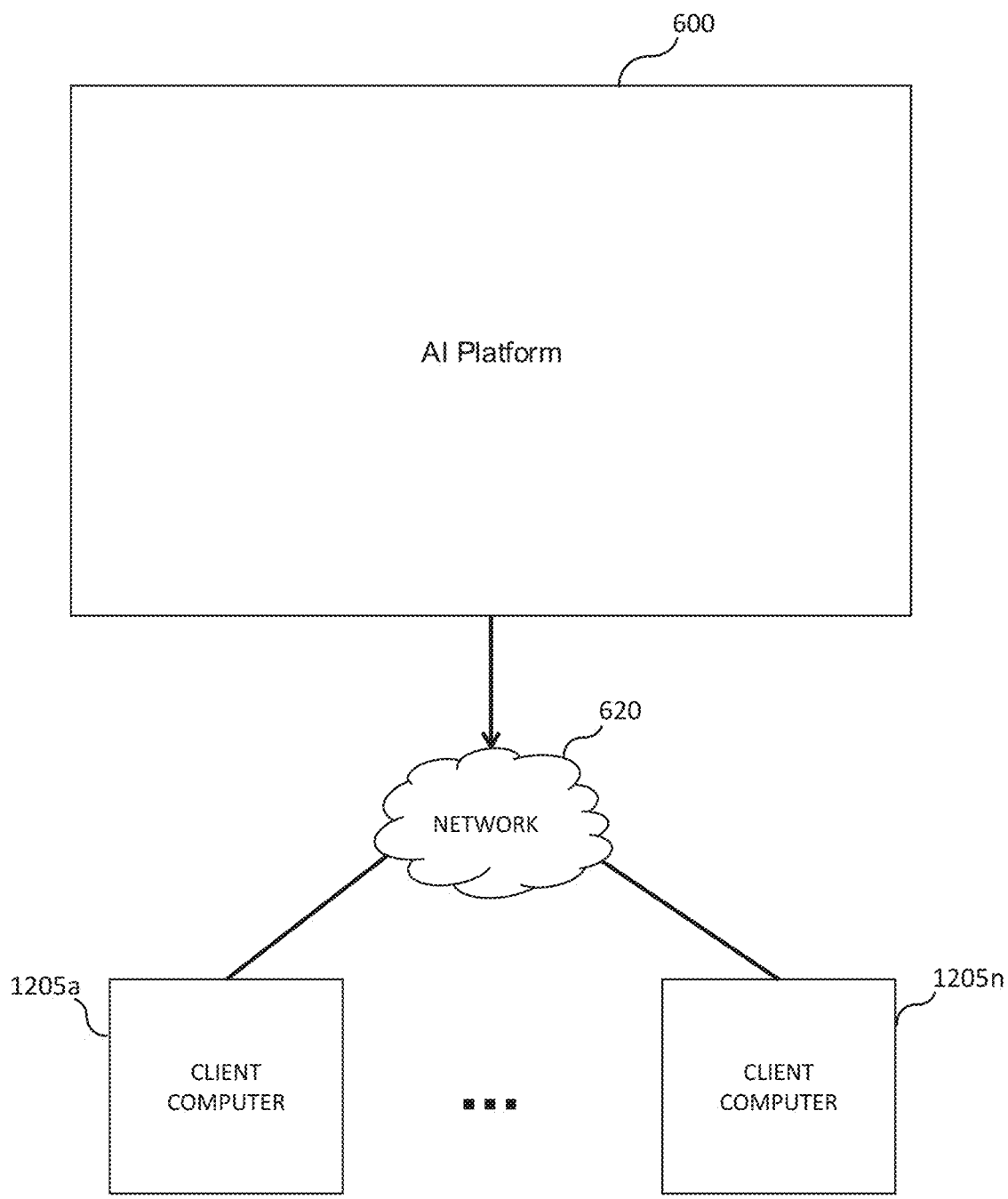
FIG. 12 illustrates a block diagram according to some embodiments.

FIG. 12 illustrates a block diagram according to some embodiments. According to some embodiments, platform/computer system 600 may be accessible over network 620 to one or more client computers or devices 1205a to 1205n.

Accordingly, in some embodiments, computer system 600 may provide a graphical user interface (GUI) or other interface to allow one or more clients to communicate and interact with the platform 600 over the network.

Set forth below are four illustrative examples of how the output from the platform 600 may be used to develop prototypes and perform clinical trials in xenotransplantation applications.

Example 1. Identification of Genetic Modification(s) Necessary to Create XenoTransplantation Donor and Derivatives Thereof to Create a Cell, Tissue, or Organ More Compatible with Human Recipient The World Health Organization (WHO) reported that globally, burns are responsible for approximately 180,000 deaths annually, while the average US incidence is nearly 18,000 partial- and full-thickness burns each year (World Health Organization, 2018). These patients are in need of an immediate treatment option to support them through the acute phase of their injuries. During this critical period, patients with severe burns are at risk of deteriorating clinical condition due to infection from opportunistic pathogens, disrupted skin barrier, and impairment of immune response, as well as hypovolemia through fluid loss at the burn site. This is frequently followed by electrolyte, temperature and pH imbalances that contribute to organ failure, and often death.

Severe and extensive, deep partial and full-thickness burn wounds requiring hospitalization, surgical excision, and skin grafting. This is clinically defined when the epidermis and dermis are destroyed and the burn extends into the subcutaneous tissue, affecting the underlying adipose tissue, fascia, muscle, and even bone. Deep partial and full-thickness burns are also referred to as third- and fourth-degree burns. Patients who experience severe and extensive, deep partial and full-thickness burn wounds require hospitalization, surgical excision, and skin grafting. During this critical period, patients with severe burns are at high risk of mortality due to a devastating sequela of complications such as increased capillary leak and release of inflammatory cytokines, infection from opportunistic pathogens, immune-compromise, hypovolemia, hypothermia, electrolyte and pH imbalances, and other detrimental deviations to pre-injury homeostasis as a result of a disruption in the skin barrier that contributes to organ failure and often death.

Patients with severe burns are at high risk of mortality due to the disruption in the skin barrier that contributes to organ failure and often death. Providing a temporary barrier against infection, helps prevent fluid loss, and restores the epidermal barrier prior to definitive wound closure with the placement of an autograft.

No ideal skin substitute exists that replaces all the characteristics of skin. Human cadaver allograft is regarded as the clinical gold standard for all biologic dressings employed for temporary wound closure, as it vascularizes and adheres to the wound bed due to the presence of viable dermal and epidermal cells. This characteristic is fundamental to the physiologic mechanism that prolongs the survival of the graft and provides a temporary restoration of barrier function with significant clinical impact in the immediate post-burn period. Another unique benefit of allograft skin is its ability to serve as an indicator of wound bed health and readiness to receive autograft, thereby reducing the morbidity associated with additional autograft harvest procedures and decreases the length of hospital stay.

Adherence, more than any other factor, defines the success of the graft. The selection criteria for a wound dressing should primarily be based on the wound bed characteristics, and due to their heterogeneous nature, no single dressing is suitable for all types.

The number of acellular products or marketed therapeutics used in the treatment of burn wound care generally augment the use of cadaveric allografts for coverage of large, full-thickness burns, because the ubiquitous use of the gold standard of treatment (allograft) is severely impeded by inadequate availability. Frequently in clinical practice, a patient with areas of severe burns could potentially have a cadaveric allograft placed in the more severe areas and have different coverings or closures for the remaining area of the burn.

Surgical procedures available for skin healing often have limited availability of healthy donor tissue and while allograft skin does provide a substitute, it also poses a risk for potential disease transmission and immune rejection. Viral infections have been transmitted via tissue allografts such as bone, skin, cornea, and heart valves. Bone allografts have transmitted hepatitis C, human immunodeficiency virus (HIV-1), and human T-cell leukemia virus. Corneas have transmitted rabies, hepatitis B virus, cytomegalovirus (CMV), and herpes simplex virus. Heart valves have been implicated in transmitting hepatitis B. HIV-1 and CMV have been transmitted by skin allografts.

Skin Substitute for Severe Burns

Aside from human skin allograft, the American Burn Association guidelines report that there is insufficient clinical trial evidence to recommend one specific dressing type over another, and clinicians should base dressing selection on wound location, size, and depth, amount of exudate, presence of infection or necrosis, and the condition of the surrounding tissue. Below is a summary of the alternative treatment options with benefits and limitations associated with each as described in Total Burn Care.

Engineered Skin Substitutes: Tissue engineered skin substitutes are an alternative to traditional wound healing strategies and tissue regeneration. Skin was the first engineered cell, tissue, or organ that went from laboratory research to patient care. Over recent decades, various bioengineered and synthetic substitutes have been developed, which are generally positioned within the injury and provide the barrier function along with protection against microorganisms, reduction of pain in wounds, and promotion of wound healing. Despite these benefits to patients, there remain several limitations to commercially available skin substitutes such as reduced vascularization, poor mechanical integrity, failure to integrate, scarring, and immune rejection. Although artificial skin products are in development and available commercially, they are still prone to rejection.

Synthetic membranes: A number of semipermeable membrane dressings can provide a vapor and bacterial barrier and control pain while the underlying superficial wound or donor sites heal. These typically consist of a single semipermeable layer that provides a mechanical barrier to bacteria and has physiologic vapor transmission characteristics. Biobrane® (Dow-Hickham, Sugarland, Tex.) is a two-layer membrane constructed of an inner layer of nylon mesh that allows fibrovascular ingrowth and an outer layer of silastic that serves as a vapor and bacterial barrier. It is widely used to provide temporary closure of superficial burns and donor sites. Wounds on which Biobrane® is to be applied must be carefully selected. They must be fresh, not infected, free of eschar and debris, moist, have a sensate surface, and demonstrate capillary blanching and refill. It is applied snugly to the cleansed wound overlapping itself or fixed to unburned skin with sterile strips of adhesive tape. The key to the successful use of Biobrane® is adherence to the wound. Therefore, the burned area must be dressed and splinted, especially across a joint, to prevent shearing of the Biobrane® from the wound surface. Satisfactory adherence usually occurs in about 4 days. Biobrane® is left intact until the wound has reepithelialized. Then it can be gently teased away. If the wound surface has even a thin veneer of residual necrotic tissue, Biobrane® will not adhere. Therefore, the use of Biobrane® is limited and shearing and disruption of Biobrane® can be problematic.

Hydrocolloid dressings: Hydrocolloid dressings are described as wafers, powders, or pastes composed of materials such as gelatin, pectin, and carboxymethyl-cellulose. They provide a moist environment favorable for wound healing and a barrier against exogenous bacteria. Hydrocolloid dressings have been effective in the treatment of small-area partial-thickness burns and are especially useful in the terminal phase of spontaneous healing of small burns.

Tissue-engineered delivery systems: Tissue-engineered delivery systems also exist which contain cultured autologous keratinocytes with or without fibroblasts. These products are not suitable for initial placement on severe and extensive, deep and full-thickness burn wounds due to the time needed for manufacturing.

Xenografts: Traditional xenografts are an animal-derived skin graft alternative to human cadaver allograft. Although various animal skins have been used for many years to provide temporary coverage of wounds, only porcine xenograft is widely used today. It has been used as primary temporary cover and as a scaffold for dermal regeneration efforts. Porcine xenograft is commonly distributed as a reconstituted product consisting of homogenized porcine dermis which is fashioned into sheets and meshed, such as EZ-Derm. Split-thickness porcine skin is also used fresh, after brief refrigeration, after cryopreservation, or after glycerol preservation. It effectively provides temporary coverage of clean wounds such as superficial second-degree burns and donor sites. Porcine xenografts on the market today are terminally sterilized, rendering the cells inactive, which limits their therapeutic capability by not allowing the graft to vascularize to the underlying wound bed. In contrast to Xeno-Skin® which is intended for treatment of severe and extensive, deep and full-thickness burn wounds, these xenografts are intended only for superficial burns.

Clinicians have long sought alternative treatment options that address the persistent shortcomings of allograft material to provide the same fundamental mechanism of action of wound closure and temporary restoration of barrier function. Aspects of the present disclosure may be leveraged to identify a suitable treatment option for a patient or patient population.

B. Ideal Solution: Xenotransplantation

Identify the Ideal Donor Animal

The intuitive approach to xenotransplantation would utilize a donor species that lacks disparities from humans, such as non-human primates. In theory, this would likely decrease the chance of hyperacute rejection. However, the success rate with organs from primates implanted in man has not been high, and there are several other practical and theoretical reasons why primates may not be a desirable source of organs. For instance, primates have a comparatively long gestation time of 170-193 days. This would affect the rate of reproduction and so restrict the rate at which colonies of suitable donor animals could be built up. The end result of this scenario would be a high cost to keep and breed primates. Furthermore, relatively few primates are of suitable size to provide organs that are similar to human organs. There are additional compatibility issues as well: for instance, baboons only have blood groups A, B, and AB, but not the O blood group (universal donor). Chimpanzees do have the O group but are already rare in the wild. Lastly, the more closely related a species is to humans, the greater the risk of transfer of disease organisms unique to the donor.

Pigs, by contrast, hold great promise as an ideal donor animal for xenotransplantation, and substantially address the formerly discussed limitations associated with non-human primates. Pigs share many genetic and physiologic characteristics with humans. Favorable breeding characteristics, the ability to genetically modify the genome of prospective source animals, as well as physical and structural similarities between pigs and human organs are compelling. Furthermore, clinically relevant scalability of swine colonies is validated via well-established agriculture and food-industry practices, which demonstrate daily that swine can be bred in sufficiently large numbers, and more importantly, to specific, prescribed standards. If intentionally bred for addressing the gap in transplantable organs, swine could present a reliable and scalable alternative to a current system reliant on—and handicapped by—donations from a finite cohort of medically acceptable human altruists.

Advantages and Disadvantages of Different Animal Sources for Xenotransplantation Despite the numerous structural similarities between pigs and humans, fundamental differences exist at the cellular level that cause naturally occurring wild-type porcine xenotransplants to hyperacutely reject and become rapidly destroyed by the recipient via ischemia. Specifically, antibody-mediated immune mechanisms lead to rapid rejection of xenotransplants. The existence of preformed "natural" antibodies to foreign antigens causes humans and non-human primates to recognize swine-derived xenograft tissues as innately foreign. This results in a rapid inflammatory response involving complement activation, exacerbating the already intense activation of the coagulation cascade that damages the graft endothelium, leading in turn to graft ischemia and necrosis. Another contributing factor to hyperacute rejection is the fact that porcine xenografts are prone to physiologically incongruous coagulation. Normally, procoagulant positive feedback loops downregulate damaging thrombus formation through the action of endothelial thromboregulatory molecules. However, human coagulation pathway molecules and porcine thromboregulatory pathways are molecularly incompatible, resulting in inefficient regulatory inhibition of said feedback loops.

Alpha Gal

One of the most common and well-studied agonists of hyperacute rejection is the alpha-1,3-galactose sugar (alpha-1,3-Gal), expressed on all nucleated cells except those of humans and primates. When human patients are exposed to it through transplantation of xeno-derived materials, preformed antibodies quickly recognize the alpha-1,3-Gal as a foreign body and subsequently initiate the process of hyperacute rejection of the xenotransplant within minutes to hours.

Extensive research suggests that genetic modification of source animals, such as removing alpha-1,3-Gal, may provide a solution to the challenge of organ rejection that currently plagues xenotransplantation. Through genetic engineering, removal of the offending alpha-1,3-Gal in the well-studied GalT-KO (knockout) swine model, dramatically reduces—but does not eliminate—the immediate host immune response. This dramatic reduction in reactivity is enough to shift the rejection response to an acute reaction (occurring within days to weeks), which is clinically useful in certain applications. Hyperacute rejection of organs derived from these GalT-KO animals is rare, and numerous studies have reinforced the promise for the treatment of human patients in need of transplants.

Xenotransplantation of vital porcine skin grafts is a promising alternative for the treatment of burns; it may help to minimize mortality and morbidity from preventable infections and fluid loss. Further, it may improve outcomes by reducing scarring and improving restoration of normal bodily functions. Porcine organs have long been considered to be favorable resources for xenotransplantation because they are physically and structurally similar to human organs, and pigs can be bred in large numbers. However, live-cell, wild-type xenogeneic materials yielded poor results in previous examinations due to immunologic incompatibilities between donors and recipients. Indeed, whenever live-cell porcine tissues were used as temporary coverage to provide barrier function in burn wounds in the past, they were applied only as a superficial dressing and required frequent changing. Although these products contained viable cells, wild-type xenogeneic tissues undergo hyperacute rejection via a rapid (minutes to hours) antibody-mediated, immunological process resulting in premature loss of the foreign graft due to ischemia. This phenomenon is triggered by recognition of an alpha-galactose (Alpha-Gal) epitope, an antigen expressed on the surface of all nucleated cells of non-human origin. Humans and non-human primates do not express this epitope, and have preformed antibodies that are catalyzed upon exposure to it.

A rapid inflammatory attack ensues that targets the cells comprising the graft endothelium. This results in destruction of the blood vessels and vascular network leading to ischemia and graft necrosis, preventing prolonged survival of a live-cell xenograft. In short, without intervention, wild type live-cell xenografts are rapidly destroyed in human hosts, and the significant clinical benefit that a comparable alternative to human cadaveric allograft could provide is lost.

Implementation of Needed Genetic Modification

To address this noticeable gap in treatment options, a specialized herd of genetically engineered, alpha 1,3 galactosyltransferase knockout (GalT-KO) porcine donors has been developed over the past 40 years by using selective breeding to establish porcine donors with defined major histocompatibility complex (MHC) genes as a large animal model for studies of transplantation biology. The objective of this program was to knock out expression of the gene that encodes the enzyme, galactose-$\alpha$-1,3-galactosyltransferase (GGTA1) and was initiated approximately 20 years ago. GGTA1 adds $\alpha$-1,3-galactose as the terminal sugar on glycoproteins found on cell surfaces of the pigs. In humans and non-human primates, natural antibodies against galactosyl-$\alpha$-1,3-galactose residues on the cell surface glycoproteins mediate hyperacute rejection of porcine organs and are the most immediate barrier to successful xenotransplantation.

The initial step used to knock out GGTA1 was to generate fibroblast cell lines from wild type miniature pig fetuses and transfect the cells with a gene trap targeting vector. A gene trap targeting vector, pGalGT, was used for homologous replacement of an endogenous GGTA1 allele. The vector contains about 21 kb of homology to the GGTA1 locus, with the coding region upstream of the catalytic domain disrupted by insertion of a selection cassette consisting of a Bip internal ribosome entry site followed by sequences encoding G418 resistance.

In some embodiments, the swine from which xenotransplantation product materials are derived include "knockout" and/or "knock-in" swine such as are disclosed in U.S. Pat. No. 7,795,493 ("Phelps"), the entire disclosure of which is incorporated herein by reference. Such swine lack active a-(1,3) galactosyl epitopes responsible for hyperacute rejection in humans upon transplantation. Multiple methods of production of knockout/knock-in swine are disclosed in Phelps including: the inactivation of one or both alleles of the alpha-1,3-GT gene by one or more point mutations (for example by a T-to-G point mutation at the second base of exon 9) and/or genetic targeting events as disclosed at col. 9, line 6 to col. 10, line 13; col. 21, line 53 to col. 28, line 47; and col. 31, line 48 to col. 38, line 22.

Confirmation of the Needed Genetic Modification

Confirmation of the absence of the galactosyl-a-1,3-galactose (Alpha-Gal) epitope on cells will be determined using fluorescence activated flow cytometry. White blood cells in whole blood are stained with a fluorochrome labeled isolectin-B4 (FITC-I-B4) and comparisons are made against blood obtained from wild type positive controls and the GalT-KO source animal twice. First, all source animals are tested at birth. Second, the same test will be performed from whole blood collected at sacrifice of the source animal and tested for stability of the gene knockout, and the negative phenotype for Alpha-Gal. The isolectin binds to the epitope on cells from the wild type pig but no binding occurs on the cells from the GalT-KO pigs. The assay serves to confirm alpha-gal epitope is not present in the genetically engineered source animal. Spontaneous re-activation of the gene, and re-expression of the Alpha-Gal moiety post sacrifice is highly improbable and unreasonable to expect; its inclusion would only deteriorate the efficacy of the xenotransplantation skin product causing it to resemble wild-type porcine tissue and hyperacutely reject as previously demonstrated.

Testing Methods

Testing was performed in controlled method FMCM2018-06. There were no changes to the critical reagents listed in the controlled method.

Porcine whole blood was lysed using RBC lysis buffer. PBMCs were then stained for viability using Live/Dead Fixable Violet dye. After staining, cells were washed to remove excess dye. Cells were then stained with conjugated isolectin B4 (for gating control, isolectin B4 was omitted). Upon completion of staining, cells were washed twice and fixed with stabilizing fixative. Cells were acquired via LSRFortessa cytometer within 24 hours of fixation.

For intra-assay precision, 6 replicates from one wild-type and one knockout sample were stained with the panel by one analyst. The results from the wild-type sample are the primary data.

For inter-analyst precision, two analysts simultaneously prepared one whole blood sample each from three wild-type and three knockout blood samples. The results from the wild-type samples are the primary data.

For lower limit of quantitation (LLOQ) and dilutability, one analyst lysed blood from one sample each of wild-type and knockout blood. The analyst used the samples to prepare the following dilutions (shown as wild-type:knockout): 1:1, 1:2, 1:4, 1:8, 1:16, 1:32, 1:64, 1:128, 1:256, and 1:512. Wild-type only and knockout only controls were also prepared.

Samples arrived within one day of the blood draw (D0). For sample stability, one analyst tested each of 3 wild-type and 3 knockout blood samples at three timepoints (D1, D2, D3).

The acquisition data generated on the LSRFortessa flow cytometer are stored in a network folder labelled "18-4709G". All laboratory methodology were recorded on worksheets 18-4709G-01 and 18-4709G-02.

Leukocytes were selected based on forward- and side-scatter profiles. Then, doublets were excluded based on the linear relationship of forward-scatter height and area. Next, live cells were selected for the negative or dim detection of Live/Dead Violet. Finally, Isolectin B4 positive events were gated based on FITC fluorescence. A single reportable was validated (percentage of Isolectin B4 positive events, based on live leukocytes).

Screening of Animal Genome

DNA is first extracted/purified, libraries are then prepared from the extracted DNA, and quality controlled (QC) for presence of suitable DNA. QC involves reviewing Bioanalyzer data for size distribution of fragments after the initial amplification as well as the size distribution of the final, prepared, barcoded libraries. After QC of prepared libraries is verified, samples will be quantified using qPCR. Templating and Sequencing will be performed on the Ion Chef and Ion GeneStudio S5 Prime instrumentation. Samples will be sequenced on a minimum of two Ion 550 sequencing chips. De novo assembly will be performed using Ion Torrent software.

Specific Screening Location:

```
MSC Cell Line GGTA1 KO via
point mutation in Exon 6
200 base pairs (bps) 5' upstream of edit:
                                    (SEQ ID NO: 1)
AAGCCACTCCACCTCCCCAAAGCTGAATGACTGAATGGTGGA

GAGTAGCTGGGAATGTTACAGCAACAGACGTCTCTCATCCAG

GATGGGGAAAAATCATTCCTTTCCTAAACTGCAAAATACAGA

CTAGATGATAATAGCATATTGTCTCCTCTAGAAATCCCAGAG

GTTACATTTACCCCATTCTTCTTTATTTCAGA

Edited site (1 bp):T --> G
200 bps 3' downstream of edit:
                                    (SEQ ID NO: 2)
ACATTGAGCATTACTTGGAGGAGTTCTTAATATCTGCAAATA

CATACTTCATGGTTGGCCACAAAGTCATCTTTTACATCATGG

TGGATGATATCTCCAGGATGCCTTTGATAGAGCTGGGTCCTC

TGCGTTCCTTTAAAGTGTTTGAGATCAAGTCCGAGAAGAGGT

GGCAAGACATCAGCATGATGCGCATGAAGACC
```

In addition to addressing a serious or life-threatening condition in severe burns, a skin transplant would serve as an ideal proof-of-principle for xenotransplantation. Revisiting the idealized characteristics discussed, we examine a skin transplant in this context.

First, skin is both an organ and a transplant. Biologically, it is the body's largest and fastest-growing organ and is classified as the primary component of the integumentary system, one of the ten macro-organ systems found in "advanced" animals. Skin fulfills several critical roles including regulating temperature, providing a dynamic barrier to the external world, and serving as a conduit to support an immense network of sensory receptors. Anthony Atala describes skin as an optimized, flat, vital structure, that was also the first "organ" to be successfully engineered ex-vivo. Further, United States Code Title 42, Section 274 and Section 301, explicitly list skin in its formal definition of human organs. Similarly, the Human Organ Transplant Ordinance (HOTO), an internationally ratified ordinance to prevent organ trading and protect donor and recipient rights to self-determination. This global legislation lists skin—and whole segments of the integumentary system—formally as an organ, and more broadly defines an organ as "any part of the human body consisting of a structured arrangement of tissues which, if wholly removed, cannot be regenerated by the body . . . ". Following the formal medical definition of a transplant is: "the removal of tissue from one part of the body or from one individual and its implantation or insertion in another especially by surgery." The HOTO defines a transplant as "the transfer of an organ from one person to another during a transplant operation, regardless of permanence."

Often, skin is classified as merely a tissue, and commonly, the term transplant is interchangeably referred to as a graft, which is more broadly defined as the implantation of a portion of living tissue "so as to form an organic union." The origin of these mischaracterizations is understandable. Grafts commonly encountered in clinical practice consist of decellularized and/or reconstituted sheets of homogenized dermis that are used to achieve temporary, superficial wound coverage. Such grafts do not retain the original tissue structure nor the metabolically active, otherwise naturally present cells, and thus do not become vascularized; no capillary ingrowth or vessel-to-vessel connections are made. Consequently, immune rejection is not a concern—the skin graft becomes "ejected" rather than rejected by the growth of a complete [host] epithelium underneath. Thus, the term graft can be correctly applied to such solutions. However, the primary qualities that differentiate a transplant from a graft are that of heightened complexity, organization, and inclusion of one or more type of tissue. In the present case, a skin transplant is fundamentally differentiated from the traditional graft counterpart. It would be comprised of live cells that perform the same function as the patient's original skin before eventually experiencing immune-mediated rejection. Thus, in this context, skin would be more accurately classified as an organ transplant.

One distinct advantage afforded to skin transplants would be the elimination of concomitant immunosuppression therapy. As discussed above, the primary function of skin is to serve as a barrier between internal and external environments. Skin performs additional, critical roles related to homeostasis, temperature regulation, fluid exchange, and infection prevention. The absence of a sufficient amount of skin can compromise the ability to perform these functions leading to high incidences of mortality and morbidity from infections and fluid loss. Skin transplants have been reliably used with notable clinical benefit to prevent these outcomes in patients with significant wounds; regardless of whether the graft is temporary or permanent. Thus, unlike other proposed transplants, use of immunosuppressive drugs would not be necessary. In fact, such regimens would be contraindicated in burn patients whose injuries already exhibit some level of comprised immune function. This is an important consideration in the paramount balance of risk-benefit to the patient.

The envisioned porcine skin transplant would be procured from the donor in a manner that does not alter its intrinsic function and would serve the identical purpose in the recipient as it did in the donor. The epidermis would remain fully intact, and dermal components would be maintained without change to structural morphology or organization of the various cells and tissues. Thus, a skin transplant would meet the fundamental standards of both minimal manipulation and homologous use, both of which are believed to be highly favorable with respect to regulatory evaluation. Xeno-Skin® is a biologically active, split-thickness, xeno-transplantation skin product. Xeno-Skin® is derived from specialized, genetically engineered (alpha 1,3 galactosyl-transferase knockout [GalT-KO]), Designated Pathogen Free (DPF), porcine donors, containing vital, metabolically active (i.e. non-terminally sterilized) porcine cells within the dermal and epidermal tissue layers. Maintenance of GE Source Animals It will be understood that the phrase "designated pathogen free," as used herein, can be used to describe animals, animal herds, animal products derived therefrom, and/or animal facilities that are free of one or more specified pathogens. Preferably, such "designated pathogen free" animals, animal herds, animal products derived therefrom, and/or animal facilities are maintained using well-defined routines of testing for such designated pathogens, utilizing proper standard operating procedures (SOPs) and practices of herd husbandry and veterinary care to assure the absence and/or destruction of such designated pathogens, including, but not limited to, routines, testing, procedures, husbandry, and veterinary care disclosed and described herein. It will be further understood that as used herein the terms "free," "substantially free" and like terms when used in connection with "pathogen free" are meant to indicate that the subject pathogens are not present, not alive, not active, or otherwise not detectable by standard or other testing methods for the subject pathogens.

Designated pathogens may include any number of pathogens, including, but not limited to, viruses, bacteria, fungi, protozoa, parasites, and/or prions (and/or other pathogens associated with transmissible spongiform encephalopathies (TSEs)). Designated pathogens could include, but not be limited to, any and all zoonotic viruses and viruses from the following families: adenoviridae, anelloviridae, astroviridae, caliciviridae, circoviridae, coronaviridae, parvoviridae, picornaviridae, and reoviridae.

Designated pathogens could also include, but not be limited to, adenovirus, arbovirus, arterivirus, bovine viral diarrhea virus, calicivirus, cardiovirus, circovirus 2, circovirus 1, coronavirus, encephalomyocarditus virus, eperytherozoon, *Haemophilus suis*, herpes and herpes-related viruses, iridovirus, kobuvirus, leptospirillum, *listeria, mycobacterium* TB, *mycoplasma*, orthomyxovirus, papovirus, parainfluenza virus 3, paramyxovirus, parvovirus, pasavirus-1, pestivirus, picobirnavirus (PBV), picornavirus, porcine circovirus-like (po-circo-like) virus, porcine astrovirus, porcine bacovirus, porcine bocavirus-2, porcine bocavirus-4, porcine enterovirus-9, porcine epidemic diarrhea virus (PEDV), porcine polio virus, porcine lymphotropic herpes virus (PLHV), porcine stool associated circular virus (PoSCV), posavirus-1, pox virus, rabies-related viruses, reovirus, rhabdovirus, *rickettsia*, sapelovirus, sapovirus, *Staphylococcus hyicus, Staphylococcus intermedius, Staphylococcus epidermidis*, coagulase-negative staphylococci, suipoxvirus, swine influenza, teschen, torovirus, torque teno sus virus-2 (TTSuV-2), transmissible gastroenteritus virus, vesicular stomatitis virus, and/or any and/or all other viruses, bacteria, fungi, protozoa, parasites, and/or prions (and/or other pathogens associated with TSEs). In some aspects, particularly in swine herds, testing for TSEs is not performed because TSEs are not reported in natural conditions in swine. In other aspects, testing for TSEs is performed as part of the methods of the present disclosure.

There are huge numbers of pathogens that could possibly be tested for in animal herds, and there is no regulatory guidance or standard, or understanding in the field as to what specific group of pathogens should be tested for in donor animals, and which specific group of pathogens should be removed from donor animal populations in order to ensure safe and effective xenotransplantation.

All swine are known to be positive for PERV A and B, and animals of this breeding colony are known to be positive for PERV C (Fishman and Patience, 2004). PERV mRNAs are expressed in all porcine tissues and in all breeds of swine tested to date.

Confirmatory detection of PERV in littermates of the source animals intended for clinical use within XenoTherapeutics' closed colony was performed. Consistent with expectations and previous experience, PERV was detected in the tissues obtained from XenoTherapeutics closed colony; this finding also coincides with findings in published scientific literature.

Final, confirmatory detection of PERV, analysis, and co-culture assays are performed as part of the Drug Product release criteria.

Feed

Records for storage and delivery of feed, water, and other consumables are maintained, and include manufacturer, batch numbers, and other pertinent information, per protocol.

Animal records have been maintained to describe the feed provided to source animals for at least two generations before their use as a source for live cells, tissues, or organs used in xenotransplantation. This includes source, vendor, and the type of feed used (including its contents). Use of feed that has been derived from animals is prohibited. Source Animals are not provided feeds containing animal proteins or other cattle materials that are prohibited by the FDA feed ban as expanded in 2008 as source animals (21 CFR 589.2000) or feeds containing significant drug contamination or pesticide or herbicide residues for source animals (21 CFR 589.2001).

Purified water is provided in sufficient quality to prevent unnecessary exposure of animals to infectious or adventitious agents, drugs, pesticides, herbicides, and fertilizers. Newborn animals are provided colostrum specifically qualified for herd qualification.

Piglets are first fed freshly made sterile colostrum (Bovine Colostrum IgG formulated for swine, Sterling Nursemate ASAP) using a feeding tube every 1-2 hours until piglet is self-feeding from feeder. During the early days, the piglet is weighed twice a day and well-being is checked and recorded twice a day. At about 2 weeks, piglets are fed 3 times per day with a Milk Replacer (Ralco Birthright) which is further supplemented with irradiated piglet grain (antibiotic free creep feed, Blue Seal 813). The amount each piglet eats at each feeding is recorded.

Cryopreservation

Product materials will be placed in the appropriate freezer rack containing cryovials with product as described above, and placed in a certified, Q-A control rate-phase freezer. Using a certified, Q-A control rate-phase freezer, the entire product is cryopreserved via one standardized control-rate freezing process:

a. Starting at 4° C., internal chamber and sample temperature probe will lower at a rate of 1° Celsius per minute until a temperature of −40° C. is achieved.

b. Once temperature of −40° C. has been reached in a controlled rate, control-rate freezer sample temperature probe should lower rapidly from −40° C. to −80° C.

c. Material is then transferred to a GLP certified, −80° C. freezer until use.

Taking 40 minutes per batch time from room temperature to −80° C. (understanding the time could be less or more, and up to 2 hours). In some aspects, penetrative cryoprotectants such as DMSO, may be used to protect morphology and tissue structure, and retain metabolic activity levels comparable to that of fresh skin. In some aspects, cryopreservation may alternatively or additionally include one or more of glycerol, gentamicin, Nystatin, L-glutamine, and other processing solutions. In some aspects, β-lactam antibiotics are not used.

Inclusion of the cryoprotective-media packaging component is intended to support cell survival during the freeze-thaw cycle required for the xenotransplantation product. Failure to include the cryoprotective media packaging component of xenotransplantation product during packaging may disrupt the integrity of the xenotransplantation product or impede the cryopreservation process, and may potentially reduce the xenotransplantation product viability below acceptance criteria. Cryopreservation of the xenotransplantation product without inclusion a cryoprotective media results in destruction of biologically active cells contained in the xenotransplantation product. Rapid formation of ice crystals and disruption of cellular membranes and mitochondrial organelle barriers occurs during the freezing process, and the dimethyl-sulfoxide ingredient acts to displace intracellular fluid. Thus, the cryoprotective media reduces the formation of such ice crystals and rapid, disruptive increase in total cellular volume that would negatively impact the cellular viability and, thus, the efficacy of the Drug Product.

During the course of a number of experiments, including the monkey studies in Example 1 herein, use of this cryoprotective-media packaging component has never been observed to cause an adverse, undesired reaction with the xenotransplantation product, or degrade and contaminate the final xenotransplantation product causing adverse reactions or outcomes to the recipient. Thus, selection of the specific material and associated specifications were chosen to meet appropriate standards necessary of a xenotransplantation product intended for human, clinical use. This including identifying a cryoprotective media with minimal, subclinical levels of DMSO, one that would satisfactorily perform without the need for inclusion of an additional xenotransplantation material (porcine serum) in the formulation. The cryoprotective media-packaging component is not used in the grafting procedure. Upon thawing, and prior to use of the xenotransplantation for therapeutic uses including as a drug product, it is discarded. CryoStor CS5 is manufactured per cGMP standards and was selected because of its certified acceptability for human, clinical use.

Cryologistics

Shipping the product to the clinical site should be done to maintain the xenotransplantation skin product material at −80° C. storage condition. One example shipping container is the EXP-6 Standard Dry Vapor Shipper having an extensive, having the following specifications:
Dynamic Holding Time 10 Days
Holding Temperature −150° C. or Colder
Core Technology Dry Vapor Liquid Nitrogen
Specimen Chamber 2.8" (71 mm) Diameter
11.5" (292 mm) Depth
Weight Dry 9.7 lbs/4.4 kg
Charged 18.3 lbs/8.3 kg
Domestic Dimensional 21.07 lbs/9.56 kg
International Dimensional 24.87 lbs/11.28 kg
Outer Box 12"×12"×22"
(305×305×559 mm)

Aspects of the shipping process include, but are not limited to, (1) cryopreservation storage; (2) xenotransplantation product in cryovial and media as described herein while in cryopreservation storage; (3) cryovial placed in dry vapor shipping container (or secondary closure system); (4) container and vial shipped via courier; (5) xenotransplantation product controlled and monitored at delivery location (can last at least 10 days at minus (−) 150 degrees Celsius or colder); (6) xenotransplantation product in cryovial and media as described herein removed from container/secondary closure system; (7) xenotransplantation product in cryovial and media as described herein placed in freezer at location being stored at −80° C.

Creation of Prototypes and Manufacturing Process

The manufacture of the Xeno-Skin, a xenotransplantation skin product, is a continuous process that begins with a designated pathogen free (DPF) source animal (GalT-KO genetically engineered miniature swine) that has been euthanized by a captive bolt. The source animal carcass is brought into a surgical suite, which has been previously sterilized with gaseous chlorine dioxide per SOP and staged with the appropriate equipment to harvest the xenotransplantation product tissue consisting of the minimally manipulated, dermal and epidermal layers from the source animal. Once harvested, the skin is processed into individual skin graft squares of two different dimensions.

Through the continuous manufacturing event, source animals are processed into aseptic xenotransplantation products. Several items are involved in the manufacture of the product relating to the source animals, including, but not limited to:

a. care and husbandry of the source animals (including, as described herein, providing certain vaccinations, carefully maintaining and analyzing pedigree records, performing proper animal husbandry, and maintaining the animals in isolation barrier conditions);

b. product manufacturing (including, as described herein, processing the source animals into the subject product from euthanizing to harvest);

c. analytical testing of the source animals (including, as described herein, screening for adventitious agents including parasitology, bacteriology, and virology assays);

d. analytical testing of the source animals (including, as described herein, confirming the source animal is an alpha-1,3-galactotransferase knockout or has other characteristics that are desired for a given application); and e. analytical testing of the source animals (including, as described herein, viral assay for Endogenous Viruses (PERV)).

Several items are also involved in the manufacture and release testing of the resulting products, including, but not limited to:

a. product manufacturing (including, as described herein, processing the drug product, storing the drug product, and releasing the drug product);
b. analytical testing of the drug product (including, as described herein, viability testing (via, e.g., MTT assay)),
c. sterility testing (including, as described herein, aerobic bacteria culture, anaerobic bacteria culture, fungal culture, *mycoplasma* assay, endotoxin test, USP <71>)),
d. adventitious agent testing (including, as described herein, PCR Assay for e.g., Endogenous Viruses (PERV)); and
e. analytical testing of the drug product (including, as described herein, histology).

For skin, the quantity of product yield from each animal can vary depending on the size of each animal. By way of example, some animals could yield between 3,000 and 6,000 cm2 in product. In one aspect, a single batch of skin product is harvested from a single source animal in a continuous process.

Product Processing Following Harvesting

The previously harvested and minimally manipulated xenotransplantation skin product (here the skin integrity being minimally manipulated dermal and epidermal tissue layers with standard cellular morphology and organization) enters the separate, adjacent room with positive pressure above that of the surgical suite, designated as the Class 10,000 (ISO-7) product processing room.

The operating room will be setup per operating preparation procedures and the operating personnel will be dressed in Tyvex suits for fume hood work. If requested, an assistant will also be dressed in a Tyvex suit. Gowning and Dressing is done with aseptic techniques. Gloves and sleeves will be sprayed with alcohol if needed. The ABSL-2 laminar flow hood, having been prior sterilized via gaseous chlorine dioxide sterilization process, will be sprayed with alcohol, e.g, 70% ethanol, and the laminar flow exhaust will be initiated. Utilizing aseptic techniques, previously sterilized via autoclave, surgical instrument, cryovials, cryotray, flasks, syringes, needles, additional containers, and all processing equipment will be placed within the laminar flow hood. Exterior packaging is sprayed with alcohol prior to being transferred to the operator As described herein, prior to operation, nylon mesh graft backing should be cut into squares of appropriate size for the dosage levels, sealed in an autoclavable pouch, and sterilized via steam. Exterior of pouch will then be sterilized with 70% ethanol and placed in the fume hood. Exterior package of 10 mL Cryovials will be decontaminated with 70% ethanol and placed into the fume hood. Sterile, autoclaved surgical instrument package should be sprayed with 70% ethanol and transferred to the operator.

Sterile syringes and needles should be sprayed with 70% ethanol and transferred to the operator. Graft tissue recently harvest form the porcine donor will be transferred to the hood. Anything entering the sterile field is wiped down with 70% ethanol prior to transfer to the operator. Operator will have access to all required materials in the fume hood: Grafts (in sterile container), Cryovials, 10 mL syringes and needles, Phase Freezer holding rack, and cut Nylon mesh. Operator should be seated at the fume hood in compliance with sterile, aseptic technique.

Each cryovial will be sterilized and labeled in advance to reduce processing time and unnecessary material exposure to DMSO prior to cryopreservation. Pans containing each xenotransplantation product and the RPMI 1640 Tissue Culture Media at room temperature with antibiotics (e.g., antipathogen bath) is placed under the laminar flow hood. The products had been bathing in the anti-pathogen bath for not less than 30 minutes to sterilize the xenotransplantation product.

In one aspect, when using UV light sterilization, the cryovials are sterilized using the UV lamp as described above. After the product is inserted into each vial, each new cap is placed on each new vial and screwed on securely. Each vial is placed under the lamp and periodically rolled for desired even exposure to light on the exterior of the vial. The vials are placed inside a glass jar that has an interior that has been previously sterilized and the exterior is sterilized by the operator with alcohol and chlorhexidine, including threads and caps. Vials are wiped down with alcohol and are placed into glass jars. The exteriors of the glass jars are drenched with alcohol outside of the hood. Under the hood, the operator bathes the glass jar lids and plunges the open ends of the jars into alcohol and wipes the exterior of the jars with alcohol (and optionally chlorhexidine) including threads of the jar. The vials are wiped with alcohol utilizing gauze and placed inside each glass jar with an instrument. The lids of the glass jars are then secured and the jars are handed to the assistant. Frequently and on a periodic basis throughout these processes, the assistant sprays the operator's gloves and arms with alcohol.

In this example, the xenotransplantation skin product, which was cut to form in the surgical suite with sterile scissors and was trimmed with 10-blade scalpel, will be re-measured with a sterile, stainless steel ruler to verify technical specifications and dimensions have been met. The xenotransplantation skin product is visually inspected to ensure no rips, tears, observable defects, or excessive or insufficient thickness are present.

Under the laminar flow hood the operator will use forceps to take a single xenotransplantation skin product from the antipathogen bath and place it upon a piece of nylon mesh that has been previously cut to fit the cryovial, centered on the nylon mesh, with the dermis side in contact with the mesh (e.g., dermis side down), taking 1 minute for each product (understanding the time could be less or more, and up to 5 minutes for each product). It will be understood that the sterile nylon mesh packaging component is utilized, among other things, to support the xenotransplantation product and prevent self-adhesion of the xenotransplantation product when rolled.

It will be further understood that the sterile nylon mesh packaging component can be of any dimension that would allow the xenotransplantation product to be placed onto the sterile nylon mesh packaging component and fit within the two dimensional surface area (i.e., the length and width not including the thickness) of the sterile nylon mesh packaging component (e.g., the two dimensional area dimension of the xenotransplantation product would be less than the two dimensional area dimension of the sterile nylon mesh packaging component).

It will be further understood that the dimensions of the sterile nylon mesh packaging component would be sized in accordance with the xenotransplantation product size and dosage. For example, the sterile nylon mesh packaging component is 8 cm×7.5 cm (60 cm2) to fit a 5 cm×5 cm xenotransplantation skin product (25 cm2) (7.5 grams) utilizing 7 ml of cryoprotective media when placed in the cryovial. It will be even further understood that the dimensions of the sterile nylon mesh packaging component is 8 cm×22.5 cm (180 cm2) to fit a 5 cm×15 cm xenotransplantation skin product (75 cm2) (22.5 grams) utilizing 5 ml of cryoprotective media when placed in the cryovial.

Unintentional adhesion of epidermal or dermal regions of the xenotransplantation skin product during packaging may disrupt the integrity of the xenotransplantation skin product and potentially reduce its therapeutic viability. Inclusion of the sterile nylon-mesh packaging component is intended to provide internal physical support to and prevent self-adhesion. The sterile nylon-mesh packaging component is not biologically or chemically active and does not directly impact the metabolic activity or efficacy of the xenotransplantation skin product itself.

During the course of numerous experiments, including the monkey studies described in Example 1 herein, use of this sterile nylon-mesh packaging component has never been observed to cause an adverse, undesired reaction with the xenotransplantation product, or degrade and contaminate the final xenotransplantation product causing adverse reactions or outcomes to the recipient. The sterile, nylon-mesh packaging component is not used in the grafting procedure. Following cryopreservation and thawing, and prior to use of the xenotransplantation product, it is discarded. Thus, selection of the specific material and associated specifications were carefully chosen for the given application. Medifab 100-Micron Nylon Mesh (Part #03-100/32-Medifab) is manufactured per cGMP standards and was selected because of its physical characteristics and certified acceptability for human, clinical use.

Under the laminar flow hood, the operator will then tightly roll this combination of xenotransplantation product and nylon mesh packaging component and place the combination within a cryovial (e.g., 10 ml vial) taking 1 minute for each product (understanding the time could be less or more, and up to 5 minutes for each product). In this aspect, the mesh material is rolled to ensure that the vertical height of the cylinder is 8 cm and uniformly fits within the 10 ml cryovial (e.g., 10 cm length and 17 mm diameter) and once completed, can be secured with a threaded seal cap. The mesh material is oriented such that the protective mesh material is on the exterior of the xenotransplantation product, and that once the rolled is complete there is no exposed or visible xenotransplantation material and it is fully encased in the protective insert. The intrinsic tensile and material properties of the sterile nylon-mesh packaging component are homogenous, and the inelasticity or stiffness of the material causes it to expand to fill the volume of the cryovial. Thus, regardless of the initial "roll-density", the material will uniformly loosen and is therefore standardized.

Under the laminar flow hood the operator will then use a sterile syringe to draw up enough sterile cryoprotective media (e.g., 5-7 ml of the media with 5% dimethyl sulfoxide (DMSO) (Cryostor CS5, BioLife Solutions)) to fill the cryovial until the skin product roll is fully immersed, ensuring that the combination of xenotransplantation skin material, mesh backing, and cryoprotectant media is flush with the 10 ml fill line, taking 1 minute for each product (understanding the time could be less or more, and up to 5 minutes for each product).

Under the laminar flow hood, the operator will seal the cryovial with the threaded cap. The identity of the contents and label information are confirmed by the operator. Labels are prepopulated and applied to the exterior of the cryovials containing the product in advance of the product processing.

Cryopreservation

Product materials will be placed in the appropriate freezer rack containing cryovials with product as described above, and placed in a certified, Q-A control rate-phase freezer. Using a certified, Q-A control rate-phase freezer, the entire product is cryopreserved via one standardized control-rate freezing process:

a. Starting at 4° C., internal chamber and sample temperature probe will lower at a rate of 1° Celsius per minute until a temperature of −40° C. is achieved.

b. Once temperature of −40° C. has been reached in a controlled rate, control-rate freezer sample temperature probe should lower rapidly from −40° C. to −80° C. c. Material is then transferred to a GLP certified, −80° C. freezer until use.

Taking 40 minutes per batch time from room temperature to −80° C. (understanding the time could be less or more, and up to 2 hours). In some aspects, penetrative cryoprotectants such as DMSO, may be used to protect morphology and tissue structure, and retain metabolic activity levels comparable to that of fresh skin. In some aspects, cryopreservation may alternatively or additionally include one or more of glycerol, gentamicin, Nystatin, L-glutamine, and other processing solutions. In some aspects, β-lactam antibiotics are not used.

Inclusion of the cryoprotective-media packaging component is intended to support cell survival during the freeze-thaw cycle required for the xenotransplantation product. Failure to include the cryoprotective media packaging component of xenotransplantation product during packaging may disrupt the integrity of the xenotransplantation product or impede the cryopreservation process and may potentially reduce the xenotransplantation product viability below acceptance criteria. Cryopreservation of the xenotransplantation product without inclusion a cryoprotective media results in destruction of biologically active cells contained in the xenotransplantation product. Rapid formation of ice crystals and disruption of cellular membranes and mitochondrial organelle barriers occurs during the freezing process, and the dimethyl-sulfoxide ingredient acts to displace intracellular fluid. Thus, the cryoprotective media reduces the formation of such ice crystals and rapid, disruptive increase in total cellular volume that would negatively impact the cellular viability and, thus, the efficacy of the Drug Product.

During the course of a number of experiments, including the monkey studies in Example 1 herein, use of this cryoprotective-media packaging component has never been observed to cause an adverse, undesired reaction with the xenotransplantation product, or degrade and contaminate the final xenotransplantation product causing adverse reactions or outcomes to the recipient. Thus, selection of the specific material and associated specifications were chosen to meet appropriate standards necessary of a xenotransplantation product intended for human, clinical use. This including identifying a cryoprotective media with minimal, subclinical levels of DMSO, one that would satisfactorily perform without the need for inclusion of an additional xenotransplantation material (porcine serum) in the formulation. The cryoprotective media-packaging component is not used in the grafting procedure. Upon thawing, and prior to use of the xenotransplantation for therapeutic uses including as a drug product, it is discarded. CryoStor CS5 is manufactured per cGMP standards and was selected because of its certified acceptability for human, clinical use.

Shipping to Clinical Site

Shipping the product to the clinical site should be done to maintain the xenotransplantation skin product material at −80° C. storage condition. One example shipping container is the EXP-6 Standard Dry Vapor Shipper having an extensive, having the following specifications:

Dynamic Holding Time 10 Days
Holding Temperature −150° C. or Colder
Core Technology Dry Vapor Liquid Nitrogen
Specimen Chamber 2.8" (71 mm) Diameter
11.5" (292 mm) Depth
Weight Dry 9.7 lbs/4.4 kg
Charged 18.3 lbs/8.3 kg
Domestic Dimensional 21.07 lbs/9.56 kg
International Dimensional 24.87 lbs/11.28 kg
Outer Box 12"×12"×22"
(305×305×559 mm)

Aspects of the shipping process include, but not limited to, (1) cryopreservation storage; (2) xenotransplantation product in cryovial and media as described herein while in cryopreservation storage; (3) cryovial placed in dry vapor shipping container (or secondary closure system); (4) container and vial shipped via courier; (5) xenotransplantation product controlled and monitored at delivery location (can last at least 10 days at minus (−) 150 degrees Celsius or colder); (6) xenotransplantation product in cryovial and media as described herein removed from container/secondary closure system; (7) xenotransplantation product in cryovial and media as described herein placed in freezer at location being stored at −80° C.

Prototype Testing Methods and FDA Product Batch/Test Release Analysis

USP<71> Sterility

Samples are transferred to Tryptic Soy Broth (TSB) or Fluid Thioglycollate Medium (FTM) as appropriate. For Bacteriostasis and fungistasis, TSB samples are spiked with an inoculum of <100 Colony Forming Units (CFUs) of 24-hour cultures of *Bactillus subtilis, Candida albicans*, and with <100 spores of *Aspergilius braseiliensis*. The FTM samples will be spiked with an inoculum of <100 CFU's of 24-hour cultures of *Staphyloccocus aureus, Pseudomonas aeruginosa*, and *Clostridium sporogenes*. If growth is not observed, the product is found to be bacteriostatic or fungistatic and fails the USP <71> Sterility Test.

Aerobic and Anaerobic Bacteriological Cultures

Samples are transferred to Tryptic Soy Broth (TSB) or Fluid Thioglycollate Medium (FTM) as appropriate. Vessels will be incubated to allow for potential growth. If no evidence of microbial growth is found, the product will be judged to comply with the test for sterility as described by USP<71>.

*Mycoplasma* Assay USP <63>

Fresh samples will be added to 100 mL of *Mycoplasma* hayflick broth and incubated at 37° C. for up to 21 days. The sample is subcultured after 2-4 days, 7-10 days, 14 days, and 21 days. The plates are then incubated at 37° C. for up to 14 days and checked for the presence of *Mycoplasma* colonies. If none are detected, the product is found to be in compliance with USP<63> and is *mycoplasma* free.

Endotoxin USP<85>

Three samples from the same lot will be tested for the Inhibition/Enhancement of the Limulus amoebocyte lysate (LAL) test. Samples will be extracted with 40 mL of WFI per sample at 37° C. for 1 hour. Samples will then be tested in the LAL Kinetic Chromogenic Test with a standard curve ranging from 5-50 EU/mL at a validated dilution. Assays will be performed in compliance with USP<85>.

MTT Assay for Cell Viability

The metabolic activity of the drug product is tested relative to control tissue samples using a biochemical assay for [3-4,5 dimethylthiazol-2-yl]-2,5 diphenyltetrazolium bromide (MTT) metabolism. Positive and negative control samples of fresh xenotransplantation product tissue (positive control) or heat inactivated discs of xenotransplantation product tissue (negative control) or the test article of Xenotransplantation product are placed in amber microcentrifuge tubes containing MTT solution (0.3 m g/mL in DMEM, 0.5 mL). The discs are treated with MTT formazan and incubated for 180±15 minutes at 37° C. and an atmosphere of 5% $CO_2$ in air. The reaction is terminated by removal of the discs and the formazan is extracted by incubation at either ambient temperature for ≤24 hours or refrigerated at 4° C. for ≤72 hours. Samples are protected from light during this time. Aliquots are taken after the extraction is complete and the absorbance at 550 nm (with a reference wavelength of 630 nm) is measured and compared to a standard curve. IB4 Assay for Alpha-Gal epitope The absence of the galactosyl-α-1,3-galactose (Alpha-Gal) epitope on cells will be determined using fluorescence activated flow cytometry. White blood cells in whole blood are stained with a fluorochrome labeled isolectin-B4 (FITC-I-B4) and comparisons are made against blood obtained from wild type positive controls and the Gal-T-KO source animal twice. First, all source animals are tested at birth. Second, the same test will be performed from whole blood collected at sacrifice of the source animal and tested for stability of the gene knockout, and the negative phenotype for Alpha-Gal. The isolectin binds to the epitope on cells from the wild type pig but no binding occurs on the cells from the Gal-T-KO pigs. The assay serves to confirm alpha-gal epitope is not present in the genetically engineered source animal. Spontaneous re-activation of the gene, and re-expression of the Alpha-Gal moiety post sacrifice is highly improbable and unreasonable to expect; its inclusion would only deteriorate the efficacy of the xenotransplantation product causing it to resemble wild-type porcine tissue and hyperacutely reject as previously demonstrated.

Porcine Endogenous Retroviral Detection Assay

PERV pol quantitation 10 uL of a 1:625 dilution of the RT reaction was amplified in a 50 cycle PERV polymerase quantitative TaqMan PCR in triplicate using a Stratagene MX300P real-time thermocycler (Agilent Technologies). 10 uL of a 1:25 dilution of the "No RT enzyme" control RT reaction was similarly treated. PCR conditions included PERV pol forward and reverse primers at 800 nM final concentration and PERV pol probe at 200 nM final concentration. Brilliant III Ultra Fast master mix (600880 Agilent Technologies) was used supplemented to 20 nM with ROX reporter dye (600880 Agilent Technologies) and 0.04 Units/µL UNG nuclease (N8080096, Life Technologies). Cycling conditions included 1 cycle of 10 minutes at 50° C. followed by one cycle of 10 minutes at 95° C. and 50 cycles of 10 seconds at 95° C. followed by 30 seconds at 60° C. with data collected at the end of each cycle. Absolute copies of PERV pol, and of porcine MHC-I and porcine GAPDH nucleic acids were measured per nanogram of input cDNA. Punch biopsies of thawed as described herein and washed xenotransplantation product are tested for the presence of PERV DNA and RNA.

Histology and Morphology

Samples of Drug Product, following the described manufacturing process, are sampled for examination for cell morphology and organization. Verification under microscope via visible examination of Hematoxylin and Eosin section staining of the epidermal and dermal layers, to ensure correct cell morphology and organization of the skin tissues and absent for abnormal cell infiltrate populations.
Process Improvements The xenotransplantation product may be further processed to ensure that it remains free of aerobic and anaerobic bacteria, fungi, viruses, and *mycoplasma*. Under sterile conditions in a laminar flow hood in a drug product processing suite using applicable aseptic techniques, immediately after, within 1, 2, 3, 4, 5, 6, 7, 8, 9, 10 seconds, within 10 seconds to 1 minute, within 1 minute to 1 hour, within 1 hour to 15 hours, or within 15 hours to 24 hours following harvest, the xenotransplantation product is sterilized, e.g., using one or more of UV irradiation or an anti-microbial/anti-fungal. In one aspect, the product may be placed into an anti-microbial/anti-fungal bath ("antipathogen bath"). The antipathogen bath may include: one or more anti-bacterial agents, e.g., ampicillin, ceftazidime, neomycin, streptomycin, chloramphenicol, cephalosporin, penicillin, tetracycline, vancomyocin, and the like; one or more anti-fungal agents, e.g., amphotericin-B, azoles, imidazoles, triazoles, thiazoles, candicidin, hamycin, natamycin, nystatin, rimocidin, allylamines, echinocandins, and the like; and/or one or more anti-viral agents. The anti-pathogen bath may include a carrier or medium as a diluent, e.g., RPMI-1640 medium. In some aspects, the anti-pathogen bath may include at least 2 anti-bacterial agents. In some aspects, the anti-pathogen bath may include at least 2 anti-bacterial agents and at least one anti-fungal agent. In some aspects, the anti-pathogen bath may include at least four agents. In some aspects, the anti-pathogen bath may include no more than 4, 5, 6, 7, 8, 9, or 10 agents. In some aspects, the anti-pathogen bath may include any combination of the foregoing.

The product may be sterilized using UV light sterilization. For example, the product is placed under the UV lamp for a desired period of time, e.g., 0.5, 1, 1.5, 2, 3, 4, 5, 6, minutes or more, then turned over to the other side, and put under the UV lamp for the same or a different period of time on opposite side. The time period for exposing a given sample to the UV may be varied based on the specific biological agents or the types of biological agents to be sterilized. For example, the product may be sterilized using a UV lamp having a UV-C intensity of at least 100 uW/cm2 for at least 2 minutes and up to 15, 12, 10, 8, 6, 5, 4, 3, or 2.5 minutes, and turned over such that its opposite surface is exposed to the UV lamp for at least 2 minutes and up to 15, 12, 10, 8, 6, 5, 4, 3, or 2.5 minutes to obtain a UV-treated product; a UV-C dosage of at least 100,000 uW sec/cm2 and up to 800,000, 700,000, 600,000, 500,000, 400,000, 300,000 or 200,000 uW sec/cm2; a UV-C dosage of at least 200,000 uW sec/cm2 and up to 800,000, 700,000, 600,000, 500,000, 400,000, or 300,000 uW sec/cm2; a UV lamp having a UV-C intensity of at least 100 uW/cm2 for at least 2 minutes and up to 15, 12, 10, 8, 6, 5, 4, 3, or 2.5 minutes.
Summary of Process Improvements
1. Animal preparation was more extensive with the addition of ethanol rinse and being repeated 2 times.
2. The use of the Amalgatome instead of the Zimmer to harvest skin.
3. Harvesting of skin on the donor.
4. Harvesting skin on one side first, then repeating the scrubs and harvest for the subsequent side.
5. Cryomedia changes from 5% and 10% with and without serum to only 5% DMSO.
6. Changes in antibiotics and antimycotics with an increased incubation time.
7. The addition of UV light at the end of the process before placing the skin into the vials

Release Assay Sampling Methodology

Once all units of the final xenotransplantation product lot have been created, units are independently, randomly selected for use in manufacturing release assays for the required acceptance criteria. These units will be marked for lot release to the various laboratory contractors, and the various analytical tests will be performed per the required cGMP conditions.

Similarly, prior to validation for human clinical use, all final xenotransplantation product must meet acceptance criteria for selecting a donor pig for material including (i) reviewing the medical record for a defined pedigree, (ii) reviewing the medical record for the test results for alpha-1,3-galactose by Flowmetrics, (iii) reviewing the medical record for a history of full vaccinations; (iv) reviewing the medical record for the surveillance tests performed over the lifetime of the pig; (v) adventitious agent screening of source animal; (vi) reviewing the medical record for infections over the lifetime of the pig; and (vi) reviewing the medical record for any skin abnormalities noted in the animal's history.

The final xenotransplantation product control strategy and analytical testing is conducted at the conclusion of the manufacturing process prior to release for clinical use. Results of the required analytical tests will be documented via a xenotransplantation product drug product Certificate of Analysis (COA) that is maintained with a master batch record pertaining to each lot of xenotransplantation product drug product.

In another aspect it will be understood that there includes an adventitious agent control strategy developed based on the source animal, including the species, strain, geographic origin, type of tissue, and proposed indication. Analytical Tests are conducted for adventitious agents, to include bacteria, fungi, *mycoplasma*, and viral microorganisms, including as follows:

Bacteriological Free Status

The bacteriological screen is conducted to confirm the drug product is free of potential biological agents of concern Humans. Both Aerobic and Anaerobic screens are conducted to ensure sterility. Samples are thawed as described herein and transferred to Tryptic Soy Broth (TSB) or Fluid Thioglycollate Medium (FTM) as appropriate. Vessels will be incubated to allow for potential growth. If no evidence of microbial growth is found, the product will be judged to comply with the test for sterility.

Mycological (Fungal) Free Status

The mycological screen is conducted to confirm the Drug Product is free of potential fungal agents of concern. Samples are thawed as described herein. After thawing, samples are transferred to a soybean-casein digest agar. Vessels will be incubated to allow for potential growth. If no evidence of fungal growth is found, the product will be judged to comply with the test for sterility per USP<71>.

*Mycoplasma* Free Status

The *mycoplasma* screen is conducted to confirm the drug product is free of *mycoplasma*. Samples are thawed as described herein and added to 100 mL of *Mycoplasma* broth and incubated at 37° C. for up to 21 days. The sample is subcultured after 2-4 days, 7-10 days, 14 days, and 21 days. The plates are then incubated at 37° C. for up to 14 days and checked for the presence of *Mycoplasma* colonies. If none are detected, the product is found to be in compliance with USP<63> and is *mycoplasma* free.

Endotoxin Free Status

The endotoxin free status is conducted to confirm the drug product is free of endotoxins and related agents of concern. Three samples from the same lot will be tested for the Inhibition/Enhancement of the Limulus amoebocyte lysate (LAL) test. Samples will be thawed as described herein and extracted with 40 mL of WFI per sample at 37° C. for 1 hour. Samples will then be tested in the LAL Kinetic Chromogenic Test with a standard curve ranging from 5-50 EU/mL at a validated dilution. Assays will be performed in compliance with USP<85>.

Viral Assays Conducted

The viral assays are conducted to confirm the source animal is free of potential viral agents of concern, confirmation of endogenous viruses (see below). This includes co-culturing and RT-PCR testing for specific latent endogenous viruses including PERV. In vivo assays are also conducted on the animal source to monitor animal health and freedom from viral infection as key aspects of the lot release criteria. Due to the endemic nature of PERV in porcine tissue, this qualifies as a positive result that does not preclude the use of such tissue. However, the virus is identified and characterized in lot release to provide information for monitoring the recipient of the xenotransplantation product.

Cell Viability Assay

The MTT assay is conducted to confirm the biologically active status of cells in the xenotransplantation product. Evidence of viability is provided through surrogate markers of mitochondrial activity as compared to positive (fresh, not cryopreserved) and negative (heat-denatured) controls. The activity of the cells is required for the xenotransplantation product to afford the intended clinical function. This is required as a lot release criteria, and is currently established that tissue viability should not be less than 50% of the metabolic activity demonstrated by the fresh tissue control comparator.

Histology and Morphology

Verification under microscope via visible examination of Hematoxylin and Eosin (H&E) section staining of the epidermal and dermal layers, to ensure correct cell morphology and organization of the xenotransplantation product tissues and cell infiltrate populations. This is conducted to confirm the appropriate physiologic appearance and identity of cells present in the xenotransplantation product. The xenotransplantation product is composed of minimally manipulated porcine dermal and epidermal tissue layers. This is required as a lot release criteria. Evidence of the following cell layers (from most superficial to deepest), in the epidermal layer are verified:
  i. Stratum Corneum
  ii. Stratum *Granulosum*
  iii. Stratum *Spinosum*
  iv. Stratum Basale
Evidence of the following cellular structures in the dermal layer are verified:
  v. Blood vessels, evidence of vasculature
  vi. Nerves
  vii. Various glands
  viii. Hair follicles
  ix. Collagen The genetically engineered source animals do not contain any foreign, introduced DNA into the genome; the gene modification employed is exclusively a knock-out of a single gene that was responsible for encoding for an enzyme that causes ubiquitous expression of a cell-surface antigen. It will be understood that the xenotransplantation product in one or more aspects do not incorporate transgene technologies, such as CD-46 or CD-55 transgenic constructs.

An endotoxin free status is conducted to confirm the drug product is free of endotoxins and related agents of concern. Protocols for the assurance of Endotoxin free status are as follows: Three samples from the same lot are tested for Inhibition/Enhancement of the Limulus amoebocyte lysate (LAL) test. Samples are thawed, extracted, and tested in the LAL Kinetic Chromogenic Test with a standard curve ranging from 5-50 EU/mL at a validated dilution in compliance with USP<85>.

The MTT assay is conducted to confirm the biologically active status of cells in the product. Evidence of viability is provided through surrogate markers of mitochondrial activity as compared to positive (fresh, not cryopreserved) and negative (heat-denatured) controls. The activity of the cells is required for the product to afford the intended clinical function and the viability parameters for one aspect ranging from 50% to 100% mitochondrial activity.

Verification under microscope via visible examination of Hematoxylin and Eosin (H&E) section staining of the epidermal and dermal layers, to ensure correct cell morphology and organization of the xenotransplantation product tissues and cell infiltrate populations. This is conducted to confirm the appropriate physiologic appearance and identity of cells present in the product.

For skin xenotransplantation products, evidence of the following cell layers (from most superficial to deepest), in the epidermal layer are verified: Stratum Corneum; Stratum *Granulosum*; Stratum *Spinosum*; Stratum Basale. Evidence of the following cellular structures in the dermal layer are verified: Blood vessels, evidence of vasculature; Nerves; Various glands; Hair follicles; Collagen.

Product processing occurs in a single, continuous, and self-contained, segregated manufacturing event that begins with the sacrifice of the source animal through completion of the production of the final product. The animal is euthanized via captive bolt euthanasia, may be moved, if necessary, in a sterile, non-porous bag, to an operating room where the procedure to harvest biological product from the source animal will occur. All members of the operating team should be in full sterile surgical gear, e.g., dressed in sterile dress to maintain designated pathogen free conditions prior to receiving the source animal and in some instanced be double-gloved to minimize contamination, and surgical areas and tools are sterilized. The source animal is removed from the bag and container in an aseptic fashion. The source animal is scrubbed by operating staff, e.g., for at least 1-10 minutes with antiseptic, e.g., Chlorhexidine, brushes over the entire area of the animal where the operation will occur, periodically pouring Chlorhexidine over the area to ensure coverage. Surgical area(s) of the animal are scrubbed with opened Betadine brushes and sterile water rinse over the entire area of the animal where the operation will occur for, e.g., 1-10 minutes.

Clinical Site Preparation

In one aspect, the drug product arrives at the clinical site as a cryopreserved xenotransplantation product. Prior to use, the xenotransplantation product must be thawed in a 37° C. water bath, removed from the vial and washed in a series of 3 sterile 0.9% saline baths at room temperature.

For the thawing process, sterile equipment and aseptic techniques are used:
 a. Prepare 200 mL of normal saline into each of three 500 mL sterile, surgical bowls.
 b. Place the unopened cryovial with the skin product in water bath having a temperature of about 25° C. In some embodiments, the temperature is about 37° C.
 c. In the bath, swirl gently for approximately 5 minutes or until tissue is mobile within the cryovial, taking care to minimize unnecessary exposure time the xenotransplantation skin product tissue is suspended in the thawed DMSO as much as possible.
 d. Open the cryovial and use sterile forceps to quickly remove tissue and mesh to transfer into a bowl of normal saline.
 e. Using sterile forceps, ensure tissue is fully submerged in saline for 15 seconds, agitating by swirling gently to maximize coverage. The underlying, supportive mesh material should be separated from the skin xenotransplantation skin product material. Use a second pair of sterile forceps to separate if necessary. Mesh can be left in the bowl, or discarded.
 f. Using sterile forceps, transfer the skin into a second bowl wash. Submerge fully and gently swirl for 15 seconds; this is a serial dilution or "rinse".
 g. Repeat the previous step, using sterile forceps to transfer the skin into a third wash of normal saline. Submerge fully and gently swirl for about 15 seconds.
 h. The entire duration of the rinse process should be completed within 60 seconds to minimize unnecessary exposure time the product is suspended in thawed DMSO in order to maximize product efficacy.
 i. Tissue is now thawed, rinsed, and ready for application. Leave in normal saline until use, not to exceed 2 hours at about 25° C.

After the complete, thaw and rinse process is complete, the xenotransplantation product is ready for placement on the wound site. Serial washes in saline, once thawed provide ample dilutive solvent to remove the residual cryoprotectant (5% DMSO solution, CryoStor CS5) and replace the intracellular fluid levels to normal homeostatic conditions. Such dilution and use of a cryoprotective media containing a sub-clinical level of DMSO ensures that any minimal, residual DMSO remaining on the xenotransplantation skin product material post-thaw would be non-appreciable and would be highly unlikely to be clinically significant. This process also ensures retention of the maximum amount of metabolically active cells, and thereby maximizing the efficacy of the xenotransplantation product.

Thawing

Following is one example of a thawing procedure for a xenotransplantation product. Thawing can occur in a Bio-Safety Cabinet with operator in sterile gloves as follows: (i) prepare 200 mL of Normal saline into each of three 500 mL surgical bowls; (ii) prepare the water bath by wiping it clean with chlorhexidine then spraying it down with 70% ethanol; (iii) after the ethanol has dried add sterile water solution into the water bath and heat to 37° C.+/−2° C.; (iv) the xenotransplantation drug product is in a double bag, leave it unopened and place it into the 37° C. water bath; (v) swirl gently for approximately 5 minutes or until the tissue is mobile within the cryovial; (vi) minimize the time the tissue spends in thawed DMSO as much as possible; (vii) spray the outside bags with ethanol and remove the vial from the outer bags and spray the xenotransplantation drug product cryovials with 70% ethanol before placing into Biosafety Cabinet; (viii) unscrew the cryovial and use forceps to quickly remove tissue and mesh to transfer into a bowl of normal saline; (ix) use forceps to ensure tissue is fully submerged in saline for 60 seconds, agitating by swirling gently to maximize coverage; (x) the mesh should be separated from the skin, using a second pair of forceps to separate if necessary; (xi) the mesh can be left in the bowl, or discarded; (xii) using forceps transfer the skin into the second bowl wash; (xiii) submerge fully and gently swirl for 60 seconds; (xiv) using forceps transfer the skin into the third bowl wash and submerge fully and gently swirl for 60 seconds. Tissue is now thawed and ready for application. Keep it moist with sterile saline in a sterile pan.

The process of rolling the inert, nylon mesh backing and the xenotransplantation skin product results in uniform "roll-density" of the xenotransplantation product. All mesh materials are cut to uniform dimensions, according to the prescribed dimensions for the given application, and are obtained from the same material lot, thus affording uniform material properties for all units of the skin product manufactured within a specific lot.

The intrinsic tensile and material properties of the nylon mesh insert are homogenous, and the inelasticity or stiffness of the material causes it to expand to fill the volume of the primary container closure system (cryovial). Thus, regardless of the initial "roll-density", the material will uniformly loosen and is therefore standardized.

The indicated amount of CryoStor CS5 media (per Dosage Strength) is applied via 10 ml-syringe with the cryovial in the vertical position, under Class 100, IS05 conditions within an ABSL-2 laminar flow hood.

Cryomedia fills the voided space(s), and gravity ensures that the fill-process begins from the base of the vertically oriented cryovial towards the fill line at the apex. Volume is added until it reaches the manufacturers demarcated 10 ml fill line. Filling the vial in this manner also facilitates the removal of air bubbles.

Once complete, the threaded cap is sealed. Visual and physical assurance of saturation and fill is accomplished by the shaking the skin product ensuring that contents are unable to shift internally. Aspects of the cryovial include, among other things, 10 ml volume, size of 17 mm×84 mm, vertical ribs facilitating cap removal, silicone washer, cap and tube made of the same polypropylene material with the same coefficient of expansion ensuring seal at all temperatures, 1 and ¼ turn thread design, thick wall, large white marking area, and round bottom allowing for ease of emptying contents.

Aspects of the secondary closure system can include, among other things, Tyvek-1073B medical grade construction, 5 inches wide×12" high, storage ability of 15 cames or 2 cryovial boxes, holding temperature of −150 degrees Celsius or colder, utilization of dry vapor liquid nitrogen, IATA rated 10 days of dynamic holding time under normal shipping conditions, specimen chamber diameter of 2.8 inches (71 mm), specimen chamber depth of 11.5 inches (292 mm), dry weight of 9.7 lbs/4.4 kg, charged weight of 18.3 lbs./8.3 kg, domestic dimensional weight of 21.07 lbs./9.56 kg, international dimensional weight of 24.87 lbs./11.28 kg, outer box dimensions of 12"×12"×22."

No additional or external impurities in the product are anticipated to be present since processing involves only the minimal mechanical manipulation of the product, and no other chemical or biological agents are introduced during this closed process. Acceptance criteria testing required for use of the source animals for the product manufacturing process is conducted as described herein and documented via the Drug Product COA. The final product is evaluated for viral adventitious agents as described herein.

In terms of shelf life, continuous storage of the xenotransplantation product as described support a shelf life long-term stability (cell-viability) of up to at least 7 years (in one embodiment is a shelf life of 6 months) when stored continuously at −80° C. The shelf-life duration of continued cryopreservation of the xenotransplantation product with of at least 7 years.

Evaluation of Prototypes

Preclinical Analysis

Xeno-Skin™ was tested under GLP conditions for safety and efficacy in non-human primate models (PSK17-01 and PSK18-01) using the same formulation and route of administration intended for human use. Non-human primates are the only suitable nonclinical subjects for the development of Xeno-Skin™ as they mimic human patient graft-host immune response and can receive treatment using the same route of administration necessitated by human burn patients. Like human patients, these animals have the preformed antibodies against alpha-gal antigens that mediate graft rejection. Data derived from these nonclinical studies are therefore highly predictive of the results in future human trials.

Animal Data: Preclinical Study PSK17-01

Study PSK17-01 was a GLP-compliant study conducted in cynomolgus monkeys utilizing 5 cm×5 cm Xeno-Skin from the 13 Nov. 2017 lot, CCBAACA1, cryopreserved in cryostor-5. Graft acceptance/rejection assessments indicated that all allogeneic grafts and Xeno-Skin™ grafts were completely adherent to the surrounding wound bed and exhibited equivalent minimal to moderate epidermolysis at the time of removal.

Primary endpoints included the screening of graft recipients for PERV pre- and post-graft placement and evaluation of xenograft and allograft rejection. Secondary endpoints included microbiologic and histopathologic analysis of kidney, spleen, liver, lung, grafts, and wound bed tissues collected at necropsy. Grafts were biopsied on Days 5 and 15. On Day 15, after the graft biopsies, the xeno- and allografts were removed and replaced with cryopreserved autologous grafts saved from Day 0 for 2 of 4 animals. Surviving animals were euthanized per study design on Day 22 for blood and tissue collections. A gross necropsy was performed when possible. Microbiological analysis was performed on blood, and select tissue samples were collected. Histopathological analysis was performed on select tissue samples collected.

Graft acceptance/rejection assessments indicated that all allogeneic grafts and Xeno-Skin™ grafts were completely adherent to the surrounding wound bed and exhibited equivalent minimal to moderate epidermolysis at the time of removal. No PERV or porcine cytomegalovirus (PCMV) transmission into the circulation or major organs was detected. No bacterial or fungal contaminants were detected in any of the grafts. As anticipated, PERV was detected in the xenografts and residual cells in the wound bed; however, co-culture with a permissive human cell line did not show transmission from porcine to human cells.

Animal Data: Preclinical Study PSK18-01

A second GLP-compliant study (PSK18-01) was conducted in cynomolgus monkeys to evaluate the safety and immunogenicity of Xeno-Skin™ further utilizing 5 cm×5 cm skin transplants from the October 2017 lot, AAAAAAAA, cryopreserved in cryostor-5. In this study, signs of graft rejection were noted by Day 21; however, grafts were not completely rejected on Day 30, as indicated by evidence of residual xenograft dermal tissue. Immunologic assays and histopathological evaluation showed no evidence of a systemic response. Microscopic evaluation of the xenograft wound beds at Day 30 or 31 demonstrated good filling of the wound defect with host and xenograft tissue. A generally mild ongoing local host inflammatory response to the residual xenograft dermal tissue, with mild to marked epithelial ulceration in 50% of sites. There was no evidence of systemic effects of xenograft application.

Primary endpoints also included screening for porcine endogenous retroviruses (PERV) pre- and post-graft placement and evaluation of the xenograft rejection. The study consisted of 2 male and 2 female cynomolgus monkeys. On Day 0, the animals had two 4 cm2 (females) or 6.25 cm2 (males) full-thickness wounds surgically created on the dorsal region. Xeno-Skin™ was placed on the wounds. The left side was identified as Site #1, and the right side was identified as Site #2. Each graft was fenestrated and secured to the surrounding tissue with sutures and bandages. Bandages were then secured with pressure dressings. Bandages were removed, and wounds were photographed and assessed on Days 7, 14, 21, and 30. Blood was also collected during the study to provide serum for immunogenicity and PBMCs for PERV testing.

Animals tolerated the surgical procedure and placement of bilateral xenografts with no significant clinical issues. Signs of graft rejection were noted by Day 21; however, grafts were not completely rejected by Day 30, as noted by evidence of residual xenograft dermal tissue. Immunologic assays showed no evidence of a systemic response. Microscopic evaluation of the xenograft implanted wound beds at Day 30 or 31 demonstrated good filling of the wound defect with host and xenograft tissue. There was a generally mild ongoing host inflammatory response to the residual xenograft dermal tissue, with mild to marked epithelial ulceration in 50% of sites. There was no histopathologic evidence of a systemic response. As seen in PSK-17-01, PERV was detected in the xenografts and residual cells in the wound bed; however, co-culture with a permissive human cell line did not show transmission from porcine to human cells.

Treatment in Humans

Clinical Study Design

XenoTherapeutics is currently conducting a Phase 1 clinical study to assess the safety and tolerability of Xeno-Skin® for the treatment of severe and extensive, deep partial and full-thickness burn wounds as a first-line treatment and temporary coverage prior to definitive wound closure XENO-001 (NCT03695939).

This study is a two cohort, six patient open-label, dose-escalation study, evaluating safety, tolerability, and efficacy of Xeno-Skin® in patients who have experienced severe and extensive, deep partial and full-thickness burn wounds requiring excision, grafting, and hospitalization.

Xeno-Skin® is placed on the excised burn wound and secured in place via suturing or stapling. The remaining excised burn wound is covered with human cadaver allograft and treated according to the local standard of care while avoiding any overlap or physical contact between the two grafts.

Inclusion Criteria:
1. The subject provides written informed consent to participate in this study
2. Males or females age greater than 18 years old
3. Females must have a negative serum pregnancy test at Screening and at Baseline and must not be nursing.
4. Male and female subjects must agree to use a protocol-approved method of contraception for a minimum of 3 months following Xeno-Skin™ placement, which includes a barrier method plus one or more of the following:
   a. Hormonal contraceptives (e.g., birth control pills, skin patches, vaginal rings, and the Depo-Provera shot)
   b. Intrauterine device (IUD)
   c. Male or female condoms with spermicide
   d. Diaphragm with spermicide
   e. Permanent tubal occlusive birth control system
5. Total Burn Surface Area (TBSA) <30% to include deep partial-thickness or full-thickness burn wound
6. Burn injury requiring excision
7. Burn injury requiring temporary allograft coverage of wound based on clinical judgment prior to definitive wound closure with autologous skin grafts
8. Sufficient burn wound area for Xeno-Skin™ placement and not located on face or hands or having a target graft site centered on high-impact areas such as joints, weight-bearing areas (e.g., soles of feet), or the inguinal region, per Investigator's judgment.

Exclusion Criteria:
1. Pregnant or lactating women
2. Documented history of infection with human immunodeficiency virus (HIV) or other condition(s) that, in the Investigator's opinion, may compromise patient safety or study objectives.
3. Immunosuppressive medication regimens, e.g., antineoplastics, high dose steroids (>10 mg prednisone/day), TNF alpha inhibitors, calcineurin inhibitors (cyclosporine, tacrolimus), anti-proliferative agents, and other immunomodulators
4. Known allergy to penicillins (such as ampicillin), ceftazidime or aztreonam, glycopeptide antibiotics (such as vancomycin) or amphotericin B.
5. Active malignancy, including those requiring surgery, chemotherapy, and/or radiation in the past 5 years. Non-metastatic basal or squamous cell carcinoma of the skin and cervical carcinoma in situ are allowed
6. Use of any experimental or investigational drugs within 30 days prior to placement of Xeno-Skin®
7. Previously received a porcine or other xenogeneic tissue product, including but not limited to: glutaraldehyde fixed porcine or bovine bioprosthetic heart valve replacements, and glutaraldehyde fixed porcine dermal matrix (e.g., EZ Derm)
8. BMI >40 kg/m2
9. HbA1c ≥7.0%
10. Treatment with systemic corticosteroids within 30 days before screening (not including inhaled steroids)
11. Electrical, chemical, or radiation burns
12. History of chronic end-stage renal disease defined as an MDRD CrCl<15 mL/min, or receiving chronic dialysis
13. History of chronic liver disease or cirrhosis (Child-Pugh Score C). Evidence of acute or chronic hepatitis B infection based on documented HBV serology testing
14. Known documented history of Hepatitis B, Hepatitis C, *Treponema pallidum*, Cytomegalovirus, herpes or varicella zoster
   a. Note: Successfully treated hepatitis C patients without evidence of end-stage liver disease is allowed. If HCV antibody reactive, then HCV RNA must be undetectable.
15. Recent (within 3 months prior to study enrollment) MI, unstable angina leading to hospitalization, uncontrolled, CABG, PCI, carotid surgery or stenting, cerebrovascular accident, transient ischemic attack, endovascular procedure or surgical intervention for peripheral vascular disease or plans to undergo a major surgical or interventional procedure (e.g., PCI, CABG, carotid or peripheral revascularization)
16. Presence of venous or arterial vascular disorder directly affecting the area of burn wound
17. Pre-existing hemolytic anemia
18. Chronic malnourishment as determined by Investigator
19. Significant pulmonary compromise
20. Systemic anticoagulation at the time of treatment or INR >2
21. Documented evidence of wound infection at Screening or Baseline
22. Evidence of sepsis and/or end organ damage
23. Acute lung injury
24. Life expectancy of less than 180 days
25. Subject who is unable to self-consent Human Patient Assessment Methods Patients are evaluated for safety and efficacy outcome measures at distinct phases of treatment: pre-operative, peri-operative, and post-operatively at the time of autografting and clinically directed follow-up appointments.

Study Evaluations and Procedures

Demographics and Medical History

Demographic information to be obtained will include date of birth, sex, ethnicity, race as described by the subject, smoking status, and caffeine consumption of the subject at Screening.

Medical history to be obtained will include determining whether the subject has any significant conditions or diseases that stopped at or prior to signing the informed consent. Ongoing conditions are considered concurrent medical conditions.

Physical Examination (Including Height and Weight)

Abnormalities identified at the Screening Visit will be documented in the subject's source documents and on the physical exam CRF. Changes that represent a worsening of condition since the Screening Visit will be captured as AEs on the AE CRF page, as deemed by the Investigator.

Adverse Event Collection

At each study visit, subjects will be questioned in a general way to ascertain if AEs have occurred since the previous visit (e.g., "Have you had any health problems since your last visit?"). Adverse events are collected from the time informed consent is signed.

Vital Signs

Vital signs shall be recorded after the subject has been in a rested position for at least 10 minutes. Blood pressure should be determined by cuff (using the same method, the same arm, and in the same position throughout the study). Any clinically significant deviations from baseline vital signs that are deemed clinically significant in the opinion of the Investigator are recorded as an AE.

Clinical Laboratory Evaluations

All clinical laboratory assays will be performed according to the laboratory's normal procedures. Reference ranges are supplied by the laboratory and used to assess the clinical laboratory data for clinical significance and out-of-range pathological changes. The Investigator should assess out-of-range clinical laboratory values for clinical significance, indicating if the value(s) is/are not clinically significant (NCS) or clinically significant (CS). Abnormal clinical laboratory values, which are unexpected or not explained by the subject's clinical condition may be, at the discretion of the Investigator or Sponsor, repeated until confirmed, explained, or resolved as soon as possible.

The Branski clinical assessment score 1 was selected to quantify relevant clinical outcomes for each patient. These scores were generated and recorded at the time of assessment, and photographs were obtained and reviewed independently by a second investigator.

Visually assessed parameters such as graft adherence, graft dislocation, presence of hyper-granulation, hematoma, and fibrin deposition reflect physically observable and unambiguous clinical signs of efficacy and represent strong, positively correlated indices with a significant capacity to predict clinical benefit.

Use of the Branski clinical assessment score allows for quantification of clinical outcomes using an ordinal scale ranging from 0 to 5. These data are then grouped into paired dichotomous, 2×2 contingency tables and are appropriate for use in statistical calculations using McNemar's test.

Scarring will be defined as the incidence and severity of scarring as assessed by the Investigator (or designee) using of the modified Vancouver Scar Scale (mVSS) at 28 days, 7 weeks, 3 months, 6 months, and 1 year post temporary graft placement. The mVSS will be recorded as not applicable for any visits that occur prior to autograft placement.

Electrocardiogram

Standard 12-lead ECGs will be recorded at certain time points. Triplicate ECGs will be taken at each scheduled time. Additional unscheduled ECGs may be recorded where clinically necessary for subject safety.

All stationary 12-lead ECG machines will be supplied by the site. Subjects should be in a supine position following an approximate 10-minute rest period for ECG recordings. Should technical difficulties occur during recording of the ECG, a reasonable attempt should be made to repeat the ECG shortly after the failed attempt.

ECGs will be read automatically and also, the Investigator will manually interpret the ECG using 1 of the following categories: within normal limits, abnormal but not CS, or abnormal and CS. Abnormal QTc readings will be manually recalculated and reported by the Investigator on the eCRF. All 12-lead ECGs will be stored for manual measurement of intervals, if necessary. Twelve-lead ECGs will be recorded using an ECG machine that automatically calculates the heart rate and measures PR interval, RR interval, QRS interval, QT interval, and QTcF and QTcB (Fridericia's and Bazett's correction) intervals. Paper ECG traces will be recorded for 10 seconds at a standard paper speed of 25 mm/sec and gain of 10 m/mV or digital recordings will be used.

One copy of the 12-lead ECG with the physician's signature and date of assessment will be filed with the source documents and captured in the appropriate eCRF. If the original ECG is printed on thermal paper, the ECG report must be photocopied and certified. The photocopy will be filed with the original ECG in the source.

All ECGs will be recorded at the determined time points.

Estimated Volume of Blood to be Drawn from Each Subject

During this study, it is expected that approximately 222.5 mL of blood will be taken from all subjects, regardless of sex.

Note: The above amount of blood to be taken for each assessment is an estimate. The amount of blood to be taken may vary according to the instructions provided by the manufacturer or laboratory for an individual assessment. However, the total volume drawn over the course of the study should be approximately 222.5 mL. When more than 1 blood assessment is to be done at the time point/period, if they require the same type of tube, the assessments may be combined.

PCR of recipient's PBMC for PERV DNA sequence,
RT-PCR of recipient's PBMC for PERV RNA, and
Serologic analysis for PERV-specific antibodies.

Assessment of barrier function, graft site and definitive wound closure (Clinical Wound Assessment Scale)

Barrier function provisioned by Xeno-Skin™, graft site and definitive wound closure will be assessed by the Investigator (or designee) using the Clinical Wound Assessment Scale at the determined time points.

Clinical assessment of the graft sites (wound beds) will be performed by the Investigator to confirm that, in the opinion of the Investigator, both the cadaver graft site/bed and the xenograft site/bed are as clean as possible, free of dead tissue, and adequately vascularized (Thornton, 2004).

Scarring Assessment (mVSS)

Incidence and severity of scaring will be assessed by the Investigator (or designee) using the modified Vancouver Scar Scale (mVSS) at the determined time points. The scale is provided in Appendix 2. The mVSS will be recorded as not applicable for any visits that occur prior to autograft placement.

PERV and Immunogenicity Testing

PERV will be monitored by assays at indicated timepoints, which assess the following:

Results of these PERV-specific assays, obtained at the time of autograft placement, will be reviewed for all patients in a cohort before the next cohort is enrolled in the study.

Immunogenicity monitoring will include assays of serum total IgG and IgM levels, human anti-porcine antibodies, and assays to determine whether cell-mediated immune reactions are occurring in response to Xeno-Skin® placement.

Clinical Outcomes

To date, four patients have been enrolled and treated in XENO-001. The three patients in Cohort 1 received a 25 cm2 graft of Xeno-Skin®, and patients in Cohort 2 receive an increased dose of 75 cm2 Xeno-Skin®, each with a human cadaver allograft comparator in a side-by-side comparison.

Surgeries to implant Xeno-Skin® were performed under the care of Dr. Jeremy Goverman (Principal Investigator) and Dr. John Schulz at the Massachusetts General Hospital (MGH) Sumner Redstone Burn Center.

Xeno-Skin® has been well tolerated by all patients, with zero adverse events or safety issues, including no evidence of zoonotic disease transmission. PERV was not detected in the plasma and peripheral blood mononuclear cells (PBMC).

In all four cases to date, Xeno-Skin® has appeared indistinguishable from the human allograft comparator. At the time of autografting, both wound dressings were fully vascularized and adherent to the wound bed. As of this application, Xeno-Skin® continues to demonstrate equivalence against the clinical gold standard of care, performing indistinguishable from the allograft comparators.

Case Study: Patient 001

Patient 001 sustained a flame-induced burn injury resulting in 10% total body surface area (TBSA), deep partial burn wounds to the lower extremities requiring tangential excision and debridement.

To preserve viable dermis, treatment included application, fixation via staples, of human cadaver allograft (HCA) as the active control versus Xeno-Skin®. On Post-Operative Day-5, Xeno-Skin® and HCA appeared indistinguishable with no graft dislocation. Both grafts were fully adherent and required mechanical removal in preparation for autografting.

Following surgical removal, the appearance of the underlying Xeno-Skin® and human cadaver allograft wound beds appeared indistinguishable. Both wound beds were equally perfused (with visible punctate bleeding) and otherwise appeared equivalent.

Definitive closure of the wounds was achieved via autologous grafting per standard of care. On evaluation Post-Operative Day-28, there were no discernible differences in wound healing between the areas covered temporarily by Xeno-Skin® and human cadaver allograft.

There have been no adverse events (AEs) related to the use of Xeno-Skin® observed or reported, and independent analysis of PERV data and medical record by the Safety Review Committee indicated no evidence of zoonotic transmission.

Case Study: Patient 002

Patient 002 sustained a flame-induced burn injury resulting in 14% total body surface area (TBSA), deep partial burn wounds to the upper torso requiring tangential excision and debridement.

To preserve viable dermis, treatment included application, fixation via staples, of human cadaver allograft (HCA) as the active control versus Xeno-Skin®. On Post-Operative Day-5, Xeno-Skin® and HCA appeared indistinguishable with no graft dislocation. Both grafts were fully adherent and required mechanical removal in preparation for autografting.

Following surgical removal, the appearance of the underlying Xeno-Skin® and human cadaver allograft wound beds appeared indistinguishable. Both wound beds were equally perfused (with visible punctate bleeding) and otherwise appeared equivalent.

Definitive closure of the wounds was achieved via autologous grafting per standard of care. On evaluation Post-Operative Day-14, there were no discernible differences in wound healing between the areas covered temporarily by Xeno-Skin® and human cadaver allograft.

There have been no adverse events (AEs) related to the use of Xeno-Skin® observed or reported, and independent analysis of PERV data and medical record by the Safety Review Committee indicated no evidence of zoonotic transmission.

Case Study: Patient 003

Patient 003 sustained a flame-induced burn injury resulting in 5-7% total body surface area (TBSA), deep partial burn wounds to the lower back requiring tangential excision and debridement.

To preserve viable dermis, treatment included application, fixation via staples, of human cadaver allograft (HCA) as the active control versus Xeno-Skin®. On Post-Operative Day-5, Xeno-Skin® and HCA appeared indistinguishable with no graft dislocation. Both grafts were fully adherent and required mechanical removal in preparation for autografting.

Following surgical removal, the appearance of the underlying Xeno-Skin® and human cadaver allograft wound beds appeared indistinguishable. Both wound beds were equally perfused (with visible punctate bleeding) and otherwise appeared equivalent.

Definitive closure of the wounds was achieved via autologous grafting per standard of care. On evaluation Post-Operative Day-29, there were no discernible differences in wound healing between the areas covered temporarily by Xeno-Skin® and human cadaver allograft.

There have been no adverse events (AEs) related to the use of Xeno-Skin® observed or reported, and independent analysis of PERV data and medical record by the Safety Review Committee indicated no evidence of zoonotic transmission.

Case Study: Patient 004

Patient 004 sustained a flame-induced burn injury resulting in 20% total body surface area (TBSA), deep partial burn wounds to the upper/middle and lower back requiring tangential excision and debridement.

To preserve viable dermis, treatment included application, fixation via staples, of human cadaver allograft (HCA) as the active control versus Xeno-Skin® (75 cm2). On Post-Operative Day-8, Xeno-Skin® and HCA appeared indistinguishable with no graft dislocation. Both grafts were fully adherent and required mechanical removal in preparation for autografting.

Following surgical removal, the appearance of the underlying Xeno-Skin® and human cadaver allograft wound beds appeared indistinguishable. Both wound beds were equally perfused (with visible punctate bleeding) and otherwise appeared equivalent.

Definitive closure of the wounds was achieved via autologous grafting per standard of care. On evaluation Post-Operative Day-51, there were no discernible differences in wound healing between the areas covered temporarily by Xeno-Skin® and human cadaver allograft.

There have been no adverse events (AEs) related to the use of Xeno-Skin® observed or reported, and independent analysis of PERV data and medical record by the Safety Review Committee indicated no evidence of zoonotic transmission.

Patient 004 may represent the most clinically relevant and significant patient outcome to date in the clinical trial as this was the oldest patient treated (exceed 65 years of age), had the largest flame induced burn wound equivalent to 20% total body surface area (TBSA), received the largest skin xenotransplant to date (75 cm2) for treatment prior to definitive wound closure, representing the maximum FDA-allowable dosage at present, was the most immune-compromised at initial presentation, longest duration in vivo, i.e. greatest length of exposure, and had the worst clinical prognosis of any patient at admission. On evaluation Post-Operative Day-51, there were no discernible differences in wound healing between the areas covered temporarily by the skin xenotransplant and human cadaver allograft. Definitive closure of the wounds was achieved making the surgical intervention a clinical success. No adverse events (AEs) related to the use of the skin xenotransplant have been observed or reported, and independent laboratory analysis indicates no zoonotic transmission.

Example II. Viable Xenogeneic Nerve Transplants Demonstrates Regeneration and Functional Recovery Across Large-Gap Peripheral Nerve Injuries in Non-Human Primates It is estimated that twenty million Americans suffer from peripheral nerve injury (PNI) resulting in nearly 50,000 surgeries annually to repair PNIs. Severe trauma to the extremities frequently results in transection of peripheral nerves, and these injuries have a devastating impact on patients' quality of life. Regeneration of these nerves, even after surgical repair, is slow and often incomplete. Less than half of patients who undergo nerve repair following an injury regain adequate motor or sensory function, and such deficits may result in complete limb paralysis or intractable neuropathic pain.

Successful peripheral nerve regeneration involves improving the rate of nerve regeneration and the reinnervation of composite muscle leading to improved function. Existing treatment options include the use of autologous nerve transplants procured from a donor site from the same patient or decellularized human cadaveric nerve allogeneic transplants. Both treatment options have severe shortcomings and thus, a need for high-quality nerve transplants for large-gap (≥4 cm), segmental peripheral nerve defects exists. Alternatives should ideally contain living Schwann cells and a matrix-rich scaffold similar to human nerves, to potentially facilitate the critical axon regeneration process via the same fundamental mechanism of action that causes autologous nerve transplants to be the current standard of care.

Porcine nerves share many physiological characteristics to human motor and sensory nerves, including size, length, extracellular matrix, and architecture. Viable xenogeneic nerve transplants include living Schwann cells and a matrix-rich scaffold, as well as offer the potential for greater clinical availability, thereby eliminating the necessity and comorbidity associated with an additional surgical procurement procedure. Skin xenotransplants derived from genetically engineered, designated pathogen free (DPF) porcine donors have demonstrated preclinical efficacy and are currently being evaluated in human clinical trials. Therefore, we hypothesized that viable, xenogeneic nerve transplants derived from GalT-KO porcine donors may be used for successful reconstruction and treatment of large-gap (≥4 cm), segmental PNIs.

Ethics

This study's surgical procedures, protocols, and guidelines for animal care were independently IACUC reviewed and monitored, and were conducted in accordance with US-FDA 21 CFR Part 58.351 and GFI 197, USDA Animal Welfare Act (9 CFR Parts 1, 2, and 3), the Guide for the Care and Use of Laboratory Animals.

Animals

All xenogeneic nerve transplants used in this study were sourced from one genetically engineered alpha-1,3-galactosyltransferase knock-out (GalT-KO), designated pathogen free (DPF) porcine donor. Five male and five female naïve rhesus macaques (*Macaca mulatta*) served as xenotransplantation nerve product recipients.

Surgical Procedures

The porcine donor was euthanized and prepared for surgery as previously described. In order to isolate the sciatic nerve prior to harvesting, a linear incision was made midway between the sacrum and the ischium and extended ventrally along the posterior aspect of the femur, longitudinally dissecting the gluteus medius, gluteus maximus, *piriformis*, and biceps femoris muscles, to the proximal tibio-fibular joint. The sciatic nerve was visualized and was harvested by radial transections distal to the nerve origin and proximal to the bifurcation into the tibial and common peroneal nerves.

This process was repeated on the bilateral side. One unmodified sciatic nerve segment was stored in RPMI media and maintained at 4° C. until surgical use 48 hours later. The other was cryopreserved and stored at −80° C. for a period of one week. Prior to transplantation, xenogeneic nerves were trimmed to 4 cm to fit the defect size.

Large-gap (≥4 cm), segmental peripheral nerve defects were surgically introduced bilaterally in all ten non-human primate subjects. Subjects, under anesthesia10, were positioned in lateral recumbency with the shoulder at 90° flexion, full internal rotation, and neutral abduction. The subcutaneous tissue and deep fascia were dissected with a 6-8 cm skin incision along the postero-lateral margin of the proximal arm towards the antecubital fossa, exposing the long and lateral heads of the triceps which converged to form the triceps aponeurosis for anatomical orientation. The intramuscular plane between the long and lateral head of the triceps was developed approximately 2.5 cm proximal to the apex of the aponeurosis. Where the radial nerve and accompanying vessels were observed against the humerus in the radial groove. The surgical plane was extended proximally and distally to minimize unintended injury. Radial nerve was distally transected approximately 1 cm proximal to the origin of the deep branch. A 4 cm segment was removed to create the defect and saved for reattachment or subsequent analysis.

Nerve transplants were attached proximally and distally with four to eight equidistant 8-0 nylon monofilament sutures at each neurorrhaphy site. The incision was then closed in layers using subcuticular, absorbable sutures.

This process was performed bilaterally per each of the ten subjects; both xenogeneic and autologous nerves were transplanted in the same surgical procedure. Limb designation (right/left) for xenogeneic or autologous transplants was randomly assigned and blinded from observers for analysis. The ten subjects were randomly, evenly divided between two surgical series, one week apart. Five fresh xenogeneic transplants were used in the first series, and five thawed viable porcine xenogeneic transplants that had been previously cryopreserved used in the second. Postoperatively, all subjects received tacrolimus for at least six months14 and trough levels were to be below 30 ng/mL.

Functional Evaluation

A previously reported radial nerve injury model was adapted to assess the functional recovery of xenogeneic and autologous nerve transplant recipients. Radial nerve injury proximal to the elbow results in a loss of wrist extension function, or "wrist drop," due to motor denervation of the extensor carpi radialis longus and extensor carpi radialis brevis muscles. Wrist extension functional assessments were performed monthly for each subject and included chair and cage-side observations of active and passive wrist angle flexion during the subject's retrieval of objects requiring wrist angle extension to obtain them. All functional assessments were video-recorded and analyzed by two independent observers to accurately measure maximum wrist angle extension.

This measurement is limited in its precision, but enhanced with the use of ordinal, categorical values instead of continuous, degree values. Angle data were converted to a range-of-motion (ROM) score by assigning a numerical value of 1 to 3 for every 30° of wrist extension from neutral (inline with the forearm, 0°). Thus, the ROM score was defined as: angles <31° (Score 1), 31° to 60° (Score 2), and 61° to 90° (Score 3), respectively.

Electrophysiology

Evaluations and analysis were performed for all ten subjects in both arms at baseline and postoperatively at 5-, 8.5-, and at 12-months for the radial motor and sensory branches by an independent specialist (Natus UltraPro with Synergy Electrodiagnostic software),17 for the following: nerve conduction velocity (NCV), compound muscle action potential (CMAP) amplitude, CMAP duration.

Histomorphometric Analysis

At necropsy, continuous resections of the nerve transplant including proximal and distal native nerve surgical beyond the neurorrhaphy site, were procured, and sectioned longitudinally via microtome to 5 μm thickness and fixed in 10% NBF for histological analysis. Samples were stained with hematoxylin and eosin, Luxol Fast Blue, and NF200.

Statistical Analysis

Data comparisons between autologous and xenogeneic nerve transplant sites, unless otherwise stated, are expressed as mean±SD per group. Statistical comparisons were performed as one-way analysis of variance tests with the Student-Newman-Keuls multiple comparisons method. Statistical analyses were performed in Prism Graph Pad version 9.1.0 software (Prism, San Diego, Calif. USA). P values less than 0.05 were considered statistically significant.

Surgical and Clinical Outcomes

All ten subjects recovered without adverse events related to the procedure. Tacrolimus levels were maintained below 30 ng/mL, however trough levels varied widely between individual subjects (4.9 to 14.2 ng/mL). At 6-months postoperatively, the tacrolimus regimen was ceased for five randomly selected subjects and was maintained for the remaining five. By 8-months, subjects on the tacrolimus regimen presented with progressing symptoms associated with tacrolimus toxicity19 such as limited mobility in knee joints, muscle rigidity, stiffness, atrophy, and significant weight loss. As a result, these five subjects were euthanized8, and the remaining five subjects survived until the end of study without incident.

Functional Recovery

Following surgery, complete loss of functional wrist extension was observed bilaterally in all ten subjects for approximately three months regardless of nerve transplant type used. The distance from the proximal neurorrhaphy site to the site of innervation of the extensor carpi radialis longus and extensor carpi radialis brevis muscles measured 16.0 cm±0.56. At a rate of axonal regeneration of 1 mm/day, 21 functional recovery was anticipated at POD-160.

By 4-months postoperative, six of ten xenogeneic transplants and all autologous began demonstrating varying degrees of functional recovery. By the end of the observation periods (8- and 12-months, respectively), all ten limbs repaired with the autologous nerve transplant demonstrated functional recovery values equal to baseline values, whereas seven limbs treated with the xenogeneic nerve transplant had recovered to preoperative levels. In the three non-responders, two xenogeneic nerves were fresh, and one was cryopreserved.

In the 17 successful cases, the rate of recovery averaged across the subjects appeared to be equivalent between the two nerve types, while the magnitude of recovery was greatest in limbs treated with autologous nerve transplants.

Nerve Conduction Velocity (NCV)

By the end of the 12-month observational period, there were no statistically or physiologically significant differences in motor or sensory conduction velocities between the autologous or xenogeneic reconstructed limbs.

At the first assessment, 5-months postoperative, an overall reduction in motor and sensory conduction velocity (−36% and −53%, respectively) from preoperative values was noted in all ten subjects: motor (64.28 m/s±2.32 to 41.16 m/s±11.63) and sensory (53.55 m/s±2.63 to 25.00 m/s±8.18).

At the second assessment, 8-months postoperative, motor conduction had increased by 48% and 23% (54.07 m/s±6.29 for autologous nerves and 56.33 m/s±5.82 for xenogeneic nerves), indicating partial remyelination of fast conducting fibers.

At the third and final assessment, 12-months postoperative, the remaining five subjects demonstrated motor velocities in both allogeneic and xenogeneic groups recovering to at least 96% of average baseline values. F-waves were elicited for all animals at all timepoints, indicating the presence of motor conduction over long neuronal pathways including the proximal spinal segments and the nerve roots. However, velocities in the sensory nerves were significantly reduced at all evaluations, and never demonstrated recovery for either type of transplant.

Compound Muscle Action Potential (CMAP) Amplitude

Preoperative actional potential amplitudes for all twenty limbs was 19.55 mV±5.03. At 5-months postoperative, a nearly complete loss was observed in both limbs of all subjects. By month 8, amplitudes for the autologous nerve transplants had recovered to 10.14 mV±2.33, whereas limbs treated with xenogeneic nerves only recovered to 6.94 mV±3.62. By the end of study, amplitudes for autologous and xenogeneic transplants were equivalent in the remaining five subjects, however both failed to fully recover to baseline values.

Compound Muscle Action Potential (CMAP) Duration

There were no statistically or physiologically significant differences in the CMAP duration between the xenogeneic and autologous transplants at any of the three timepoints. Baseline CMAP duration were 3.9 ms±0.68 for allogeneic nerve and 3.9 ms±0.55 for xenogeneic nerves. At 5-months postoperative, the duration of the compound muscle action potential was prolonged in both groups (temporal dispersion) and peaked at 8-months postoperative (10.14 mV±2.33, autologous and 6.94 mV±3.62, xenogeneic). For the five remaining subjects at 12-months postoperative, durations recovered partially (−23%, autologous and −41%, xenogeneic) but remained prolonged over baseline values.

Histomorphometric Analysis

At necropsy, neuromas of varying degree were observed at the proximal and distal anastomotic sites for both types of nerve transplants. Microscopic examination at these sites with H&E staining revealed fibrous tissue proliferation with variable inflammation, generally consisting of foreign body reaction around the sutures, as well as multidirectional proliferation of small diameter nerve branches consistent with neuroma formation. Mild fibrosis, with embedded nerve fibers and neurofibrils generally coursing longitudinally, was observed across the original defect site with fibrin deposits at the sites of anastomosis.

At the 8-month end point, the size of the nerve fibers across the defect site for all of the five subjects were comparable for both nerve transplants, ranging from 100 to 300 µm, whereas when measured perioperatively, autologous nerve radius exceeded 300 µm. At the end of study for all ten subjects, xenogeneic axon diameter [2.50 µm±0.40] was smaller than that of the autologous control [3.40 µm±0.55], but neither fully recovered to the perioperative axonal diameter of the native radial nerve [4.00 µm±0.00].

Luxol Fast Blue staining revealed varying degrees of myelination of the transplanted nerves. Overall, for both groups, the regions proximal to the nerve transplant regions demonstrated minimal to mild demyelination, and more severe in the distal regions. At necropsy, evidence of myelination was more prominent in the autologous transplants, whereas demyelination was more severe at sites treated with the xenogeneic nerve transplant. There were no histologically discernable differences between fresh or cryopreserved transplants.

Given the similarities in physiological characteristics to human motor and sensory nerves, and preclinical and early clinical success9 of xenogeneic skin transplants, viable, xenogeneic nerve transplants derived from GalT-KO porcine donors seemed to be a plausible high-quality alternative to autologous nerve in successful reconstruction and treatment of large-gap (≥4 cm), segmental PNIs.

In this study, the onset of functional recovery was observed at 4-months postoperative with both nerve types, but the magnitude of the recovery for the xenogeneic transplants was less than the autologous control. Of the seven successful xenogeneic treated limbs, six demonstrated comparable recovery magnitude and rate to the autologous nerve transplant controls, while the seventh presented a delayed recovery with comparable outcomes in electrophysiology and histological outcomes.

Two of the three non-responders that failed to recover functional wrist activity had noticeable unilateral muscle atrophy, and at necropsy, in situ macroscopic examination revealed non-viable tissues in this region as compared to the homologous area in the contralateral arm. Upon microscopic examination, no nerve fibers were detected, and the continuity of the transplant could not be confirmed. It is not clear as to whether this was technical failure or if the neuromuscular junction had fully degenerated to the degree that reinnervation could not occur.

Although wrist extension measurements are inherently limited by subjectivity and the inability to achieve single-degree precision, but even categorical rankings, these data suggest that the regain of function was less robust overall in the xenogeneic transplant than the autologous control.

The subtherapeutic dose of tacrolimus was administered to all subjects in order to stimulate nerve regeneration, as previously reported, however, the toxicity exhibited by five subjects limited the study's potential analysis and statistical power. Another limitation was the lack of a non-tacrolimus-treated control group necessary to elucidate the relative benefit of the regimen.

Decrease in motor conduction velocity is assumed to be due to both axonotmesis and neurapraxia, whereas an increase suggests a recovery of fast conducting fibers and remyelination, consistent with the corresponding histological observations. However, the presence of nerve conduction does not indicate complete functional muscle innervation, and uneven conduction may indicate localized areas of demyelination, remyelination with immature myelin, loss of fibers, or connective tissue blockages.

The magnitude of the action potential reflects the integrity of the motor neuron, neuromuscular junction, and the strength and number of the motor units responding to stimulation. A decrease in amplitude reflects a combination of axonotmesis, focal demyelination, Wallerian degeneration, and partial conduction block or motor unit impairment, all which can present as weakness. The return of amplitude, albeit incomplete, suggests that motor units between the two groups were reinnervated and return of fast conducting axons.

An increase in CMAP duration (temporal dispersion) can indicate segmental or uneven demyelination. In such cases, the action potential duration will be longer with a lower amplitude, both signs observed at each timepoint.

These data indicate a trend towards the recovery of motor nerves. In contrast, radial sensory nerve conduction showed no such trend. While in some cases, sensory action potentials were weakly elicited indicating possible sensory reinnervation from collateral sensory nerves, it is likely that sensory deficits were present in all subjects at all postoperative observations.

Overall, a generally more favorable outcome in the functional recovery, larger nerve fibers, and a greater degree of remyelination was observed with the reconstructions involving autologous nerves, but otherwise there were no statistically significant or meaningful differences observed by electrophysiology and histologic assessments. Possible contributing factors include variable axon diameter and bundle quantity between the non-human primate and porcine nerves, especially given the use of the sciatic nerve as the transplant source to repair a radial nerve, as well as the inherent immunological difference which likely contributed to the observed edema, cell infiltrates, and tertiary lymphoid nodules and thus a subtle impact on overall axonal regeneration. Lastly, the observed 2:1 ratio between the fresh and cryopreserved xenotransplants which failed is not statistically significant, and there was no histological evidence of negative impact to the clinical outcome based on the preservation method.

In this study, peripheral nerve defects were successfully reconstructed with the use of genetically engineered, DPF porcine donor xenogeneic nerve transplants, without adverse event or impacts to safety attributed to the xenogeneic transplant. These data demonstrate that the transplantation of viable, xenogeneic nerve transplants derived from genetically engineered, DPF porcine donors, may be a promising source of viable donor nerves for transplantation across large-gap (≥4 cm), segmental peripheral nerve injuries, and the promising findings warrant further evaluation.

Additional Analysis of Data and Conclusions

In one 12-month study, the safety and efficacy of viable, large-caliber, mixed-modal xenogeneic nerve transplants derived from genetically engineered, designated pathogen free porcine donors were evaluated as a potential method of reconstructing large-gap (≥4 cm) peripheral nerve neurotmesis in non-human primates. Twenty million Americans suffer from peripheral nerve injury (PNI) resulting in nearly 50,000 surgeries annually. Successful early intervention improves the rate of nerve regeneration and reinnervation, but existing treatments have severe shortcomings. There is a critical need for high-quality surgical therapeutics. Candidate therapies should ideally contain viable Schwann cells and a matrix-rich scaffold. Porcine nerves share many physiological characteristics with human motor and sensory nerves and offer the potential for greater clinical availability. We thus hypothesized that viable porcine nerve transplants may be an effective alternative to existing surgical therapeutics. We published the study's clinical outcomes (e.g. regain of function, electrophysiology). Here we specifically assess the histological and immunological responses to xenogeneic transplantation.

Bilateral, 4 cm radial nerve neurotmesis, the complete physiological and anatomical transection of axons and connective tissue, was surgically introduced in ten Rhesus monkeys. For each subject, one limb was repaired with an autologous nerve transplant and the contralateral limb with xenogeneic in a blinded manner. Over a 12-month observational period, samples of nerve, spleen, liver, kidney, lung, and heart were evaluated for various macro-and-microscopic histomorphological characteristics. Subjects were iteratively assessed for anti-GalT-KO porcine IgG and IgM antibodies and the presence of porcine cells by qPCR.

Previously reported functional recovery was observed in both autologous and xenogeneic treated limbs Inflammation was greater at xenogeneic transplant sites, including infiltrating populations of lymphocytes, macrophages, and histiocytes, with the notable presence of tertiary lymphoid nodules along the exterior myelin sheath. Anti-GalT-KO porcine IgG and IgM levels and trends were consistent with our previous experience, and our ongoing clinical trial. Micro-chimerism was not detected in any tissues sampled, nor was there evidence of any systemic effects attributed to the xenogeneic transplant.

These long-term, in vivo data suggest promising safety and tolerability following reconstruction with viable, porcine nerve transplants. Key findings include the lack of systemic porcine cell migration over 12-months in subjects and complete elimination of the transplanted porcine tissue. Combined, these data are encouraging for neural xenotransplantation therapies and more broadly support the clinical feasibility of xenotransplantation.

In the same 12-month study, a standardized experimental model was adapted to evaluate the safety and efficacy of viable, large-caliber, mixed-modal xenogeneic nerve transplants derived from genetically engineered, designated pathogen free porcine donors as a potential method of reconstructing large-gap (≥4 cm) peripheral nerve neurotmesis in non-human primates (NHP). Previously reported[1] functional recovery was observed. There were no statistically significant differences between autologous or xenogeneic treated limbs in conduction velocity of motor or sensory nerves, compound muscle action potential (CMAP) amplitude, or CMAP duration. No evidence of systemic effects or adverse events were attributed to the xenogeneic transplants in any of the ten subjects. Given the promise of xenogeneic nerve transplants demonstrated in this preclinical study, we present here an analysis of the microbiological safety, with particular emphasis on porcine endogenous retrovirus (PERV), of viable porcine nerve transplants as a safe alternative to currently available surgical therapeutics for large-gap (≥4 cm) peripheral nerve injuries in NHPs.

PERV copy number and expression were analyzed alongside micro-chimerism to assess the presence of porcine cells by qPCR. Samples analyzed included xenogeneic (n=5) and autologous (n=5) nerve tissues harvested at 8- and 12-months post-treatment, sera and PBMCs from subjects (n=10) obtained at various timepoints over the 12-month study, and spleen, kidney, liver, and lung sections obtained at necropsy.

The genetically engineered, designated pathogen free porcine nerve transplant donor was negative for *Toxoplasma gondii*, leptospirosis, influenza A, PCMV, PRV, PRCV, and PRRSV, consistent with the microbiological profile of our clinical xenotransplant donors. No PERV or micro-chimerism amplification was observed in porcine xenogeneic or NHP autologous nerve samples. Recipient PBMCs, sera, and tissues tested negative for PERV RNA and/or DNA amplification. There was no evidence of circulating porcine cells in any tissues analyzed. All samples met the quality criteria for analysis.

These long-term, in vivo data suggest promising microbiological safety following reconstruction with viable porcine nerve transplants. There was no evidence of transmission of nor infection with PERV in any tissues or samples analyzed, at any time, in any subject. One limitation of the study is the use of Rhesus monkeys, which have previously been found to exhibit inefficient PERV infectability. Interestingly, no porcine cells were detected in any nerve samples obtained at necropsy from any xenogeneic treated limbs. This aligns with histological evidence of complete remodeling of the xenogeneic nerve transplant in vivo. These findings are encouraging for the safety and tolerability of neural xenotransplantation therapies and more broadly support the promising clinical feasibility of xenotransplantation.

Example III. Creation of Hypoimmunogenic Porcine Cells Via CRISPR Reprogramming at MHC Class II Locus—A Proof of Concept for Methods of Engineering Transplantable, Personalized Cells from Non-Human Donors

Porcine Cell Lines

Swine pulmonary alveolar cell line (clone 34D/21) was purchased from American Typed Culture Condition (ATCC) and cultured in RPMI 1640 and 20% FBS. The porcine mesenchymal stem cells pMSCs were derived from porcine bone-marrow material and cultured in 10% FBS w/1% Pen/Strep in DMEM media, and Ficoll-Paque Plus (d=1.077 g/mL) to room temperature.

Whole Genome Sequencing

The Next Generation Sequencing (NGS) of the entire porcine alveolar macrophage's genome was completed. Total DNA was isolated directly from the porcine alveolar macrophage using the FastDNA SPIN Kit as recommended by the manufacturers. The DNA concentrations were assessed using the Qubit 2.0 fluorometer, which uses fluorescent dyes to determine the concentration of nucleic acids, with the Qubit dsDNA HS Assay Kit. All PCR reactions were executed in a Bio-Rad C1000 Thermal Cycler. PCR reactions performed to amplified porcine alveolar macrophages and were carried out with the Qubit dsDNA HS Assay Kit. Quality control (QC) was performed to exclude the possibility of cross-contamination and in each PCR reaction. QC involves reviewing bioanalyzer data for the size distribution of fragments after the initial amplification and the size distribution of the final, prepared, barcoded libraries. After the QC of prepared libraries was verified, samples were quantified and normalized. Templating and sequencing were performed on the Ion Chef and Ion GeneStudio S5 Prime instrumentation. Each sample was sequenced using two Ion 550 sequencing chips. Porcine genome assembly and bioinformatics were performed, interpreted, and converted into a single selection consensus with annotations for the specific genes of interest.

HLA-Typing

Identifying the specific allele possessed by each of the five donors was done by the University of Massachusetts. These anonymous donor genetic samples were provided by the Xeno Diagnostics, LLC through its Institutional Review Board (IRB), and the Next Generation Sequencing (NGS) of each of the five donors' genomes were completed.

CRISPR Reprogramming at MHC Class II

Point Mutation Genetic Knock-Out

To eliminate the SLA-DR gene, a point mutation was created in exon 1 of the DRB1 region. First, a gRNA based on the genomic sequence, determined using Sanger Sequencing, was created to designate the specific spot to perform this mutation. Next, CRISPR-Cas9 was used to change the base pair (bp) at the desired location so that the codon it resided in was now a premature stop codon. This prevented the entire coding sequence (CDS) from being transcribed, and subsequently, its protein from being translated.

Fragment Deletion Genetic Knock-Out

Using the SLA-DR knockout-edited cell as a starting point, its SLA-DQ gene was additionally knocked out. Again, a gRNA was designed, this time to find a specific 263 bp sequence in the second exon of the SLA-DQB1 region. This section was then cut out using CRISPR-Cas9 to abolish protein translation from this gene as well. More specifically, this was done to prevent the SLA-DQB1 binding region, the section that recognizes pathogens in the body, from forming, thereby terminating the function of the SLA-DQ groove and SLA-DQ overall. The gRNA used here is as follows: GUGUCCCUGGCCAAAGCCAA (SEQ ID NO: 3); cut location: chr7:29,125,345.

Fragment Insertion Genetic Humanization

The double knock-out SLA-DR−/−SLA-DQ−/− cell was then further built upon to make the cell act more closely to a human cell. To humanize the cell and return function and expression of the DQ molecule, the human analog to the removed porcine section of SLA-DQB1, HLA-DQB1, was inserted where the original porcine section was removed. For this, a 263 bp section was inserted. A specific allele was used so that testing against human recipients with the same or different alleles (03:01:01) could be tested. The gRNAs and cut location are as follows: Guide RNA Sequence 1: GGCACGACCCUGCAGCGGCG (SEQ ID NO: 4), and cut location: chr7:29,186,966; Guide RNA Sequence 2: CGGUACACGAAAUCCUCUG (SEQ ID NO: 5), and cut location: chr7:29,187,231.

Fragment Deletion of SLA-DQA1

Parallel to the HLA-DQB1 knock-in, another experiment was run. The SLA-DQA1 gene was knocked out utilizing the same method as the fragment deletion for the B1 region. The gRNAs and cut location data are as follows: Guide RNA Sequence 1: UUAAGCCAUAGGAGGCAACA (SEQ ID NO: 6) and cut location: chr7:29,168,790; Guide RNA Sequence 2: UGAUGUGAACGGGUAAAGAA (SEQ ID NO: 7) and cut location: chr7:29,169,054. This was done in tandem with the HLA-DQB1 knock-in, not built upon it, in order to create a triple knock-out cell line lacking SLA-DRB and SLA-DQB1, and DQA1.

Analysis of Editing Efficiency Via Sanger Sequencing

Guide RNAs used in the genetic editing process are complexed together with sp Cas9 to form a ribonucleoprotein (RNP). RNPs and donors are then delivered to the cells via the optimized electroporation setting using a 200 point optimization. The cells are then recovered for two days before the edits created are evaluated. Positive control sgRNA (RELA) is always transfected at the same time. The percentage of knock-in sequences of the genetic target(s) are rigorously assessed. To achieve this, the edited site is PCR-amplified. The resulting clones are screened and sequenced to precisely identify those that harbor the edits required. Two clones are then selected for further expansion and final QC.

Flow Cytometry

Wild-type and genome-edited porcine alveolar macrophage (PAM) cells were cultured for 48 hours in RPMI- 1640/20% FBS, 2 mM L-Glutamine with/without 100 ng/mL IFNg and stained by anti-pig SLA class I, SLA class II DR, SLA class II DQ antibodies and CD152 (CTLA-4) fusion protein (binds to porcine CD80/CD86). Samples were acquired in Novacyte flow cytometry, and data were analyzed using NovoExpress. To verify that the initial knock-out of both the DR and DQ genes was a success, phenotypic testing was done. Flow cytometry was performed on cells after knock-out to verify that there was no expression of either knocked-out gene.

Preparation of Gel Electrophoresis of PCR Products

4% and 6% agarose gels were prepared using low EEO agarose of 95% purity (Sigma-Aldrich, A5093) dissolved in 1× Tris-Acetate EDTA (TAE) buffer (40 mM Tris-acetate, 1 mM EDTA, pH 8.3, Fisher Bioregents BP13324) by heating the solution in a microwave oven for 2-3 minutes. 5 µl of ethidium bromide (10 mg/ml) (OmniPur, Calbiochem, 4410) was added to the melted agarose, and it was immediately poured on a UV transparent gel casting tray of 15×10 cm size (BioRad, 1704416) fitted with a 20 well comb. High concentration agarose gels should be poured rapidly as the gel solidifies quickly. The gel tray was placed on a wide mini-sub cell GT horizontal electrophoresis system (Bio-Rad, 1704468) and the electrophoresis chamber filled with 1×TAE buffer till about 1 cm above the gel.

10 µl of each PCR sample was loaded into each well and electrophoresis was performed for 1 hour and 10 minutes at 6.7 volts/cm (based on distance between the electrodes). Our power supply (1000/500 power supply, Bio-Rad) was set to 100 V. 4% agarose gels were run at room temperature (25° C.) while 6% gels were run at 4° C. The percent of agarose used (4-6%) and time of electrophoresis (30 min to 2 h) may need to be adapted to the size of amplicon and electrophoresis apparatus used. A DNA size marker (Gene ruler 1 kB plus, Thermo Scientific, SM1331) was used. No separate dye or loading buffer is needed since the GoTaq green master-mix is a ready-to-use solution containing two dyes. Gel images were acquired using a regular gel-documentation system (Syngene, InGenius3).

Cell Isolation, Culturing, and CD4+ T Cell MLR

Flow cytometry data was analyzed using NovoExpress flow cytometry analysis software. A pseudocolor plot of FSC-H and SSC-H was created with the former on the x-axis. A gate that included the cells but not the events between −0.2×10^6 and −0.8×10^6 on the x-axis (mostly debris) was drawn. A second plot of FSC-H on both axes was created on the Main gate. On this second plot a Single Cell gate using Polygon Gate was drawn. High area containing cells were excluded. Next, a histogram for "Fluorochrome/Reagent" (x-axis) and Count (y-axis) on the "Single" gate plot (the second one created). The Median Fluorescence Intensity (MFI) was then calculated by drawing a "Range Gate" that included all cells. The number of positive and negative populations relative to the limit of blank (LOB) was found using a "Bi-Range Gate". The MFI values were recorded and rMFI was calculated for each target.

Somatic Cell Nuclear Transfer (SCNT) (Creation of Prototypes)

Porcine mesenchymal stem cells pMSCs were used as nuclear donors and cultured. For enucleation, denuded oocytes were enucleated by aspirating the polar body and metaphase chromosomes in a small amount (<15% of the oocyte volume) of cytoplasm using a 25-µm beveled glass pipette. After enucleation using a fine injecting pipette, a single donor cell was inserted into the perivitelline space of the enucleated oocyte. Membrane fusion was induced by applying an alternating current field of 2 V cycling at 1 MHz for 2 s, followed by a DC pulse of 200 V/mm for 20 µs, using a cell fusion generator. Following fusion, the reconstructed embryos were placed in bicarbonate-buffered porcine zygote medium 5 (PZM-5) containing 0.4 mg/mL bovine serum albumin (BSA) for 1 h prior to activation. Activation was performed by applying DC pulses of 150 V/mm for 100 µs in 297 mM mannitol containing 0.1 mM CaCl2, 0.05 mM MgSO4, 0.01% PVA (w/v), and 0.5 mM HEPES. After activation, the reconstructed embryos were cultured in bicarbonate-buffered PZM-5 containing 0.4 mg/mL BSA and 7.5 µg/mL CB for 3 h to suppress extrusion of the pseudo-second polar body. After culture, the reconstructed embryos were thoroughly washed and cultured in bicarbonate-buffered PZM-5 supplemented with 0.4 mg/mL BSA in 4-well dishes for 7 days at 38.5° C. under 5% CO2 without changing the medium. The development of the reconstructed embryos into blastocysts was examined 7 days after activation.

Example IV. Creation of Hypoimmunogenic Porcine Cells Via CRISPR Reprogramming at Beta-2-Microglobulin, MHC Class I Locus—A Proof of Concept for Methods of Engineering Transplantable, Personalized Cells from Non-Human Donors Swine Cell Lines Swine pulmonary alveolar cell line (clone 34D/21) was purchased from American Typed Culture Condition (ATCC) and cultured in RPMI 1640 and 20% FBS.

Whole Genome Sequencing

The Next Generation Sequencing (NGS) of the entire porcine alveolar macrophage's genome was completed. Total DNA was isolated directly from the porcine alveolar macrophage using the FastDNA SPIN Kit as recommended by the manufacturers. The DNA concentrations were assessed using the Qubit 2.0 fluorometer, which uses fluorescent dyes to determine the concentration of nucleic acids, with the Qubit dsDNA HS Assay Kit. All PCR reactions were executed in a Bio-Rad C1000 Thermal Cycler. PCR reactions performed to amplified porcine alveolar macrophages and were carried out with the Qubit dsDNA HS Assay Kit. Quality control (QC) was performed to exclude the possibility of cross-contamination and in each PCR reaction. QC involves reviewing bioanalyzer data for the size distribution of fragments after the initial amplification and the size distribution of the final, prepared, barcoded libraries. After the QC of prepared libraries was verified, samples were quantified and normalized. Templating and sequencing were performed on the Ion Chef and Ion GeneStudio S5 Prime instrumentation. Each sample was sequenced using two Ion 550 sequencing chips. Porcine genome assembly and bioinformatics were performed, interpreted, and converted into a single selection consensus with annotations for the specific genes of interest.

HLA-Typing

Identifying the specific allele possessed by each of the five donors was done by the University of Massachusetts.

These anonymous donor genetic samples were provided by the Xeno Diagnostics, LLC through its Institutional Review Board (IRB), and the Next Generation Sequencing (NGS) of each of the five donors' genomes were completed.

Knock-Out of Beta-2-microglobulin Via CRISPR

We targeted both copies of B2M with the same sgRNA to obtain a full B2M knock-out cell line. We cannot confirm the successful editing of B2M due to the lack of specific primers and similarities between the two copies present. However, we can deliver a 96-well plate of KO clones generated with a single sgRNA.

Analysis of Editing Efficiency Via Sanger Sequencing

Guide RNAs used in the genetic editing process are complexed together with sp Cas9 to form a ribonucleoprotein (RNP). RNPs and donors are then delivered to the cells via the optimized electroporation setting using a 200-point optimization. The cells are then recovered for two days before the edits created are evaluated. Positive control sgRNA (RELA) is always transfected at the same time. The percentage of knock-in sequences of the genetic target(s) are rigorously assessed. To achieve this, the edited site is PCR-amplified. The resulting clones are screened and sequenced to precisely identify those that harbor the edits required. Two clones are then selected for further expansion and final QC.

SnapGene Sequencing Software

SnapGene sequencing software was used to align and compare our PAM cell genome with our five human donors in order to verify that the genes of interest were similar between species. Once this was confirmed, the aligned sequences were used to identify the homologous human sequence of B2M to be inserted into the Rosa26 safe harbor.

Before insertion, the pB2M promoter was first tacked onto the beginning of the hB2M sequence. This upstream region has been well characterized in literature, with specific sequences mapped out in the genome. These known sequences were used and compared with our PAM genome to find this unique porcine donor's promoter region. The base pair sequence for the human was then spliced together with this promoter sequence using SnapGene sequence analysis software to ensure that the promoter and coding sequence fit together as desired.

Rosa26 Safe Harbor

The complete insertion sequence of the human B2M and the porcine promoter was sent to Synthego for genetic insertion. There, they were able to place the fragment of DNA into the Rosa26 safe harbor.

Recombinant Human Beta-2 Microglobulin

Human as Beta-2-microglobulin (B2M) is a component of MHC class I molecules which belongs to the beta-2-microglobulin family. Human B2M is present on all nucleated cells. B2M associates not only with the alpha chain of MHC class I molecules, but also with class I-like molecules such as CD1 and Qa. Loss of this function causes iron excess and hemochromatosis. Defects in B2M are the cause of hypercatabolic hypoproteinemia (HYCATHYP). This protein is generated from a DNA sequence encoding the human B2M (NP_004039.1) with a polyhistidine tag at the C-terminus. The recombinant human B2M consists of 110 amino acids and migrates as an approximately 13.2 kDa band in SDS-PAGE under reducing conditions as predicted.

Cytosol B2M protein concentration in lysate was determined for both the WT PAM cell and the B2M knock-out clones. An enzyme-linked immunosorbent assay (ELISA) test was used to determine how much B2M was present in the cell and secreted into the media. Both WT and PAM clones were cultured 80% confluency on a 24-well plate. Cells were then washed with 500 uL ice-cold 1×PBS two times. This same solution was then added into the wells (200-300 uL) and adherent cells were scraped into a pre-cooled microfuge tube using a cold plastic cell scraper. Two freeze-thaw cycles (−80° C.) were done in order to break the cell membrane and lysates centrifuged for five minutes at 5000×g at 4° C.

The total protein concentration in each lysate was determined using the BioTek Take 3 Micro-Volume Plate and assayed immediately in an ELISA experiment. Quantitative sandwich ELISA experiment was performed per manufacturer protocol. First, a microplate was pre-coated with a B2M specific antibody. Standards and samples were then pipetted into wells and incubated for two hours at 37° C. Next, any unbound substance was removed and a biotin-conjugated antibody specific for B2M was added to the well and again incubated (2 hours at 37° C.). After washing, avidin conjugated Horseradish Peroxidase (HRP) was added to the wells and incubated for an hour. Unbound HRP enzyme was removed and a substrate solution was added. Color development was stopped and intensity of 450 nm and 570 nm color was measured. BrdU incorporation was measured using Synergy H1 Hybrid Reader and absorbances were read at 450 nm and 570 nm.

Flow Cytometry

Phenotyping of clones was done to test for cell surface expression of B2M and SLA Class I on WT PAM and B2M KO clones. Cells were prepared in a flow buffer (1×PBS pH=7.4, 2 mM EDTA, 0.5% BSA) in a way of 100 uL cell addition. They were then spun down and the buffer and medium removed from the wells. The master mix was prepared in a flow running buffer using 10 ug/mL SLA-class I and B2M per well. This buffer concentration was determined experimentally. Staining buffer was then transferred into the wells (100 uL), and cells were mixed with a gentle pipette up-down and incubated for 30 minutes at 4° C. Next, cells were spun down (~300×g for three minutes) and washed 2× (200 uL flow buffer). Cells were stained with a secondary antibody solution (10 ug/mL) inflow buffer for 30 minutes at 4° C. and washed twice using the same buffer as previously stated. Lastly, cells were then resuspended in 200 uL 0.5% PFA containing MACS buffer and acquired in Novocyte Flow Cytometry.

Preparation of Gel Electrophoresis of PCR Products

4% and 6% agarose gels were prepared using low EEO agarose of 95% purity (Sigma-Aldrich, A5093) dissolved in 1× Tris-Acetate EDTA (TAE) buffer (40 mM Tris-acetate, 1 mM EDTA, pH 8.3, Fisher Bioregents BP13324) by heating the solution in a microwave oven for 2-3 minutes. 5 µl of ethidium bromide (10 mg/ml) (OmniPur, Calbiochem, 4410) was added to the melted agarose, and it was immediately poured on a UV transparent gel casting tray of 15×10 cm size (BioRad, 1704416) fitted with a 20 well comb. High concentration agarose gels should be poured rapidly as the gel solidifies quickly. The gel tray was placed on a wide mini-sub cell GT horizontal electrophoresis system (Bio-Rad, 1704468) and the electrophoresis chamber filled with 1×TAE buffer till about 1 cm above the gel.

10 µl of each PCR sample was loaded into each well and electrophoresis was performed for 1 hour and 10 minutes at 6.7 volts/cm (based on distance between the electrodes). Our power supply (1000/500 power supply, Bio-Rad) was set to 100 V. 4% agarose gels were run at room temperature (25° C.) while 6% gels were run at 4° C. The percent of agarose used (4-6%) and time of electrophoresis (30 min to 2 h) may need to be adapted to the size of amplicon and electrophoresis apparatus used. A DNA size marker (Gene ruler 1 kB plus, Thermo Scientific, SM1331) was used. No separate dye or loading buffer is needed since the GoTaq green master-mix is a ready-to-use solution containing two dyes. Gel images were acquired using a regular gel-documentation system (Syngene, InGenius3).

Cell Isolation, Culturing, and CD4+ T Cell MLR

Human PBMCs from five IRB donors (Donor #11, #19, #29, #50, and #57) sourced by Xeno Diagnostics, LLC through its Institutional Review Board (IRB) program were used in this study. Isolated PBMCs were cryopreserved and stored in LN2 until use. Prior to use, the cryopreserved PBMCs were thawed and rested overnight in a 37° C. CO2 incubator. Human CD8(+) T cells were isolated using a CD8(+) T-cell isolation kit (StemCell Technology). CD4(+) T cells were labeled using CellTrace™ Violet (CTV) Cell Proliferation Kit and were co-cultured with untreated and IFNg treated PAM (Mitomycin C treated-WT and genetically modified cells) cells in the presence and absence of anti-CD28. All cultures were in CTS™ T-cell expansion culture medium (CTS-OPT) with 2 mM L-glutamine addition. On day eight of co-culturing, cells were stained using CD4-FITC, CD69-APC, and CD25-APC/Cy7 markers. Cells were analyzed on a Novocyte Flow Cytometer.12,15 On Day 6, media was collected for cytokine (IFNg and TNF-a) production analysis using MagPix™ (Luminex™) technology.

Somatic Cell Nuclear Transfer (SCNT) (Creation of Prototypes)

Porcine mesenchymal stem cells pMSCs were used as nuclear donors and cultured. For enucleation, denuded oocytes were enucleated by aspirating the polar body and metaphase chromosomes in a small amount (<15% of the oocyte volume) of cytoplasm using a 25-µm beveled glass pipette. After enucleation using a fine injecting pipette, a single donor cell was inserted into the perivitelline space of the enucleated oocyte. Membrane fusion was induced by applying an alternating current field of 2 V cycling at 1 MHz for 2 s, followed by a DC pulse of 200 V/mm for 20 µs, using a cell fusion generator. Following fusion, the reconstructed embryos were placed in bicarbonate-buffered porcine zygote medium 5 (PZM-5) containing 0.4 mg/mL bovine serum albumin (BSA) for 1 h prior to activation. Activation was performed by applying DC pulses of 150 V/mm for 100 µs in 297 mM mannitol containing 0.1 mM CaCl2, 0.05 mM MgSO4, 0.01% PVA (w/v), and 0.5 mM HEPES. After activation, the reconstructed embryos were cultured in bicarbonate-buffered PZM-5 containing 0.4 mg/mL BSA and 7.5 µg/mL CB for 3 h to suppress extrusion of the pseudo-second polar body. After culture, the reconstructed embryos were thoroughly washed and cultured in bicarbonate-buffered PZM-5 supplemented with 0.4 mg/mL BSA in 4-well dishes for 7 days at 38.5° C. under 5% CO2 without changing the medium. The development of the reconstructed embryos into blastocysts was examined 7 days after activation.

Figure 13:
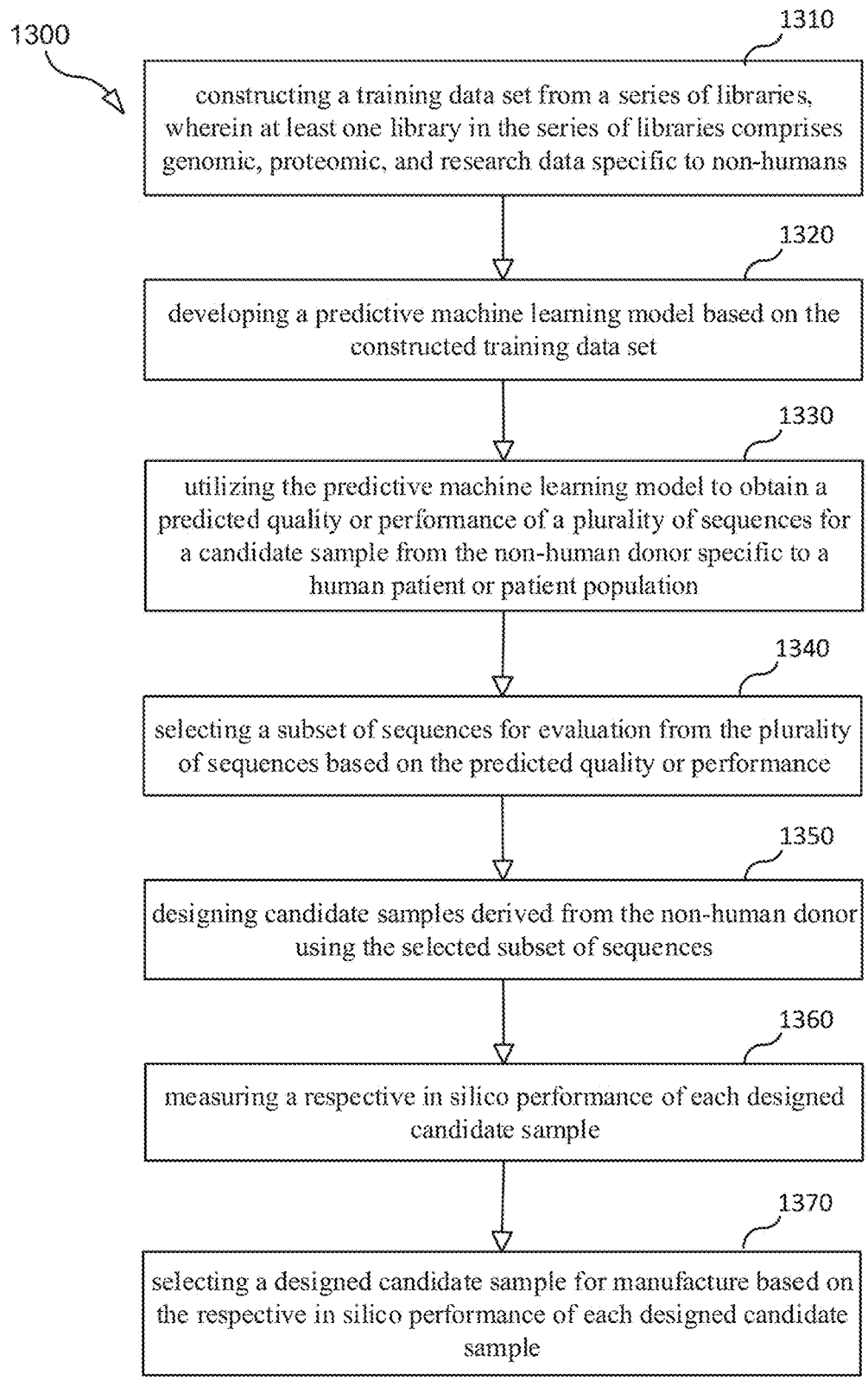
FIG. 13 illustrates an exemplary flow chart according to some embodiments.

FIG. 13 illustrates an exemplary flow chart according to some embodiments. In some embodiments, method 1300 is performed by the computer system 600 for predictive engineering of a sample derived from a genetically optimized non-human donor suitable for xenotransplantation into a human having improved quality or performance.

At step 1310, the method includes the step of constructing a training data set from a series of libraries, wherein at least one library in the series of libraries comprises genomic, proteomic, and research data specific to non-humans.

At step 1320, the method includes the step of developing a predictive machine learning model based on the constructed training data set.

At step 1330, the method includes utilizing the predictive machine learning model to obtain a predicted quality or performance of a plurality of sequences for a candidate sample from the non-human donor specific to a human patient or patient population. Quality or performance may relate to, but is not limited by, one or more of the following: 1. reduced immunogenicity; 2. reduced telomerase activity (such as longer lifespan of the cell, more cell mitosis events, increased availability, reduced microbiological burden, adventitious agents, etc.); 3. lacking innate genetic defects (such as removing or deleting the presence of disease etiology in the donor animal, and thus having no deleterious mutations in somatic transplanted cells); 4. lacking the cancer-causing agents (Oct4/Sox2/cMyc/Klf4) required to make human autologous or allogeneic iPSCs; 5. cell, tissue, and/or organ of the porcine donor at any stage of cell differentiation (such as blastocyst, embryonic, fetal, neonatal, juvenile, and adult); 6. inclusion of advantageous extracellular epitopes or upregulation; 7. a patient-specific candidate sample, e.g. truly personalized medicine; and 8. the candidate sample can be stored for future use for long durations and/or in greater quantities.

At step 1340, the method includes the step of selecting a subset of sequences for evaluation from the plurality of sequences based on the predicted quality or performance.

At step 1350, the method includes the step of designing candidate samples derived from the non-human donor using the selected subset of sequences.

At step 1360, the method includes the step of measuring a respective in silico performance of each designed candidate sample.

At step 1370, the method includes the step of selecting a designed candidate sample for manufacture based on the respective in silico performance of each designed candidate sample.

EMBODIMENTS

1. A method for predicting a non-human candidate donor organ or tissue sample suitable for xenotransplantation into a human, the method comprising:

obtaining a first human leucocyte antigen (HLA) sequence for a first human recipient in electronic format;

submitting the first HLA sequence to a computer, wherein the computer correlates the first HLA sequences to one or more major histocompatibility complex (MHC) sequences of non-humans based on experimental data; and obtaining from the computer an indication of a match of a first non-human candidate donor to the first human recipient based on the correlating.

2. The method of embodiment 1, wherein the experimental data comprises a plurality of training data, wherein each training data comprises a MHC sequence for a non-human donor, a HLA sequence for a human recipient, and a mixed lymphocyte reaction (MLR) assay result, wherein the MLR assay result comprises an indication of xenotransplantation compatibility of the MHC sequence with the HLA sequence.

3. The method of embodiment 1, wherein the non-human candidate donor is a swine and the MHC sequence is a SLA sequence.

4. The method of embodiment 3, wherein the non-human candidate donor is a genetically engineered swine.

5. A method for predicting a non-human candidate tissue or organ sample suitable for xenotransplantation into a human, the method comprising obtaining experimental sequencing data from one or more sources, wherein the experimental data comprises a plurality of training data, each training data comprising a set of (i) a major histocompatibility complex (MHC) sequence for a non-human donor, (ii) a first human leucocyte antigen (HLA) sequence for a human recipient, and (iii) a mixed lymphocyte reaction (MLR) assay result, wherein the MLR assay result comprises an indication of xenotransplantation compatibility of the first MHC system with the first HLA system;

submitting the training data to a computer; and constructing a machine learning model used to predict a xenotransplantation compatibility of a non-human donor and a human recipient by iterating, using the computer, over the training data.

6. The method of embodiment 5, further comprising:

obtaining an first HLA sequence for a first human recipient in electronic format;

submitting the first HLA sequence to the computer, wherein the computer correlates the first HLA sequence to MHC sequences of non-humans using the machine learning model; and obtaining from the computer an indication of a match of a non-human candidate donor to the first human recipient based on the correlating.

7. A computer program product configured to perform any of the methods of embodiments 1-6.

8. A system comprising:

a processor;

a non-transitory computer-readable memory coupled to the processor, wherein the processor is configured to perform any of the methods of embodiment 1-6.

9. A method for prognostic monitoring of a grafted engineered organ from a non-human donor in a human recipient, the method comprising:

obtaining observation data of the human recipient with the grafted engineered organ in electronic format;

submitting the observation data to a computer, wherein the computer correlates the observation data to one or more recipient health statuses based on experimental data; and obtaining from the computer a predictive health status of the first recipient based on the correlating.

10. The method of embodiment 9, wherein the predictive health status of the human recipient indicates one or more of: a status of the grafted engineered organ xenotransplantation or a status of the health of the human recipient.

11. The method of embodiment 9, wherein the observation data comprises one or more of accumulated or real-time observation data of the human recipient.

12. The method of embodiment 9, wherein the grafted engineered organ is from a genetically engineered swine.

13. A method for prognostic monitoring of a grafted engineered organ from a non-human donor in a human recipient, the method comprising:

obtaining experimental data from one or more sources, wherein the experimental data comprises a plurality of training data, each training data comprising a set of (i) observation data of a human recipient with a grafted engineered organ and (ii) a health status of one or more of the human recipient or the grafted engineered organ;

submitting the training data to a computer; and constructing a machine learning model used to predict a health status of one or more of a human recipient or a grafted engineered organ by iterating, using the computer, over the training data.

14. The method of embodiment 13, further comprising:

obtaining a first observation data for a first human recipient in electronic format;

submitting the first observation data to the computer, wherein the computer correlates the first observation data to one or more health statuses using the machine learning model; and obtaining from the computer a predictive health status of the first human recipient based on the correlating.

15. A method for identifying classes of non-human candidate donor organ or tissue samples suitable for xenotransplantation into a human, the method comprising:

obtaining a plurality of human leucocyte antigen (HLA) sequences in electronic format;

assigning each HLA sequence of the plurality of HLA sequences to a recipient class, wherein each recipient class corresponds to a respective human population; and, correlating each recipient class to one or more non-human candidate donor classes.

16. A computer programmed product configured to perform any one of the methods of embodiments 9-15.

17. A system comprising:

a processor;

a non-transitory computer-readable memory coupled to the processor, wherein the processor is configured to perform any one of the methods of embodiment 9-15.

While various embodiments of the present disclosure are described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context. It will be apparent to those skilled in the art that various modifications and variations can be made in the method and system for suggesting revisions to an electronic document without departing from the spirit or scope of the invention. Thus, it is intended that embodiments of the invention cover the modifications and variations of this invention provided they come within the scope of the appended claims and their equivalents.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

The invention claimed is:

1. A method for predictive engineering of a non-human tissue or organ sample derived from a genetically optimized non-human donor to have improved quality and performance for xenotransplantation into a human, the method comprising:
   constructing a training data set from a series of libraries, wherein the training data set comprises genomic, proteomic, and research data specific to non-humans, information specific to a human patient or patient population, and one or more of:
   protein variant data,
   genomic, proteomic, and research data specific to human vertebrates, or
   genomic, proteomic, and research data specific to known pathogens and diseases;
   developing a predictive machine learning model based on the constructed training data set, wherein the predictive machine learning model is selected from a set of: a neural network model, a Bayesian network model, a support vector machine model, a k-nearest neighbors model, or a combination thereof;
   utilizing the predictive machine learning model to obtain a predicted quality or performance of a plurality of nucleotide sequences for introduction into a genome of a genetically optimized non-human donor specific to the human patient or patient population;
   selecting a subset of nucleotide sequences from the plurality of nucleotide sequences for evaluation based on the predicted quality or performance;
   designing candidate non-human tissue or organ samples for xenotransplantation in the human patient or patient population using the selected subset of nucleotide sequences;
   performing iterative simulations for prognostic health outcomes or predicted health status for the human patient or human patient population as a result of treatment with each designed candidate non-human tissue or organ sample;
   measuring, based on the iterative simulations, a respective in silico performance of each designed candidate non-human tissue or organ sample for xenotransplantation in the human patient or patient population; and
   selecting a designed candidate non-human tissue or organ sample for manufacture and xenotransplantation in the human patient or patient population based on the respective in silico performance of each designed candidate non-human tissue or organ sample;
   manufacturing a prototype sample using the selected designed candidate non-human tissue or organ sample; and
   treating the human patient or patient population with a tissue or organ transplant comprising the manufactured prototype sample.

2. The method of claim 1, further comprising:
   measuring an in vitro performance of the manufactured prototype sample.

3. The method of claim 2, further comprising:
   evaluating the in vitro performance as compared to the in silico performance; and
   refining the predictive machine learning model based on the evaluating.

4. The method of claim 1, wherein the information specific to the human patient or patient population comprises clinical qualities or attributes specific to the human patient or patient population, wherein the clinical qualities comprise one or more of:
   genomic, nucleotide or proteomic, amino acid sequences,
   HLA sequences to one or more major histocompatibility complexes (MHC) serotype,
   titers,
   viability,
   density,
   concentration,
   demographics,
   results of diagnostic assays, in vitro assays, mixed lymphocyte reaction (MLR) assays,
   current and past medical and family histories,
   current and past medical diagnoses,
   current and past clinical documentation,
   current and past medications, or
   observational or experimental data of a human recipient with an engineered sample.

5. The method of claim 1, wherein the plurality of nucleotide sequences comprise one or more genomic alterations to be introduced into the genome of the non-human donor.

6. The method of claim 1, wherein the predictive machine learning model performs design of experiments (DOE) to systematically correlate data from the series of libraries in the training data set.

7. The method of claim 1, wherein the predictive machine learning model develops a sequence-activity model for predicting a clinical relevance, therapeutic optimization, or xenotransplantation compatibility of a candidate non-human tissue or organ sample to be derived from the non-human donor, as a function of multiple independent variables.

8. The method of claim 7, wherein the multiple independent variables comprise a plurality of linear terms and one or more non-linear terms.

9. The method of claim 8, wherein the non-linear term comprises a coefficient and two or more dummy independent variables.

10. The method of claim 9, wherein the coefficient indicates a relative impact on an activity by an interaction of the two or more dummy independent variables.

11. The method of claim 9, wherein each of the two or more dummy independent variables specifies a presence or absence of one residue or codon at a different sequence position of two or more sequence positions.

12. The method of claim 7, further comprising:
selecting one or more non-linear terms from a group of potential non-linear terms, where each comprises a product of multiple factors comprising different coefficients, two or more dummy independent variables, and one or more non-linear terms; and
iterating to select one or more genomic, nucleotide or proteomic, amino acid sequences based upon a predictive ability of the sequence-activity model.

13. The method of claim 12, wherein the sequence-activity model comprises a regression model, which comprises a support vector regression model, and the coefficients are obtained by a support vector machine.

14. The method of claim 13, wherein the predictive machine learning model identifies, from the genomic, nucleotide or proteomic, amino acid sequences provided by the sequence-activity model, one or more amino acid residues or codons to be varied or to remain fixed in the genome of the non-human donor, based on a rank-scored value of residue positions in order of their impact to clinical relevance, therapeutic optimization, and xenotransplantation compatibility.

15. The method of claim 7, wherein the clinical relevance relates to one or more of:
whether the candidate non-human tissue or organ sample works for its intended purpose;
whether the candidate non-human tissue or organ sample treats a disease or has negative side-effects;
a long-term benefit, or
an extended life span or improved clinical outcome.

16. The method of claim 7, wherein the therapeutic optimization relates to one or more of:
number of cells required;
type of cell required;
cells, tissues, and/or organs required;
dosage regimen;
elimination or reduction in undesirable concomitant medications or therapies; or
xenotransplantation compatibility of a candidate non-human tissue or organ sample to be derived from the non-human donor.

17. The method of claim 1, wherein the utilizing the predictive machine learning model further comprises:
inputting a variable representing one or more genomic nucleotide or proteomic, amino acid sequences specific to the human patient or patient populations to be introduced as genomic alterations to create an optimized non-human donor suitable for xenotransplantation.

18. The method of claim 17, wherein the one or more genomic alterations comprise at least one alteration selected from the group consisting of: a single nucleotide polymorphism, nucleotide sequence insertion, nucleotide sequence deletion, or nucleotide sequence replacements, or site-directed mutagenic substitution.

19. The method of claim 18, wherein the one or more genomic alterations comprise sequences from human and non-human major histocompatibility complexes (MHC).

20. The method of claim 1, wherein the predicted quality or performance is based upon an introduced genetic alteration.

21. The method of claim 1, wherein the predicted health status indicates
a status of the candidate non-human tissue or organ sample derived from the non-human donor,
or a status of health of the human patient or patient population.

22. The method of claim 1, wherein one or more genetic alterations are introduced into the designed candidate non-human tissue or organ sample for manufacture.

23. The method of claim 1, further comprising iterating over the constructing, developing, utilizing, selecting, and designing steps until a determined level of improved quality or performance of the designed candidate non-human tissue or organ sample is achieved.

24. The method of claim 1, wherein the prototype sample comprises a skin graft from the non-human donor.

25. The method of claim 1, wherein the prototype sample comprises a nerve transplant from the non-human donor.

26. The method of claim 1, wherein the non-human donor is a porcine donor.

27. The method of claim 1, wherein the improved quality or performance relates to one or more of the following:
reduced immunogenicity;
reduced telomerase activity;
lacking innate genetic defects;
lacking cancer-causing agents;
cell, tissue, and/or organ of the non-human donor at any stage of cell differentiation inclusion of advantageous extracellular epitopes or upregulation;
a patient-specific candidate tissue or organ sample;
storage for longer durations and/or in greater quantities.

28. The method of claim 1, wherein the predictive machine learning model is a neural network model.

* * * * *

SEQUENCE LISTING

<160> NUMBER OF SEQ ID NOS: 7

<210> SEQ ID NO 1
<211> LENGTH: 200
<212> TYPE: DNA
<213> ORGANISM: Artificial Sequence
<220> FEATURE:
<223> OTHER INFORMATION: MSC Cell Line GGTA1 KO via point mutation in
      Exon 6 (200 bps 5' upstream of edit)

<400> SEQUENCE: 1
aagccactcc acctccccaa agctgaatga ctgaatggtg gagagtagct gggaatgtta      60
cagcaacaga cgtctctcat ccaggatggg gaaaaatcat tcctttccta aactgcaaaa    120
tacagactag atgataatag catattgtct cctctagaaa tcccagaggt tacatttacc    180
ccattcttct ttatttcaga                                                 200

<210> SEQ ID NO 2
<211> LENGTH: 200
<212> TYPE: DNA
<213> ORGANISM: Artificial Sequence
<220> FEATURE:
<223> OTHER INFORMATION: MSC Cell Line GGTA1 KO via point mutation in
      Exon 6 (200 bps 3' downstream of edit:)

<400> SEQUENCE: 2
acattgagca ttacttggag gagttcttaa tatctgcaaa tacatacttc atggttggcc      60
acaaagtcat cttttacatc atggtggatg atatctccag gatgcctttg atagagctgg    120
gtcctctgcg ttcctttaaa gtgtttgaga tcaagtccga gaagaggtgg caagacatca    180
gcatgatgcg catgaagacc                                                 200

<210> SEQ ID NO 3
<211> LENGTH: 20
<212> TYPE: RNA
<213> ORGANISM: Artificial Sequence
<220> FEATURE:
<223> OTHER INFORMATION: Fragment Deletion SLA-DQ gene  gRNA

<400> SEQUENCE: 3
gugucccugg ccaaagccaa                                                  20

<210> SEQ ID NO 4
<211> LENGTH: 20
<212> TYPE: RNA
<213> ORGANISM: Artificial Sequence
<220> FEATURE:
<223> OTHER INFORMATION: Fragment Insertion Genetic Humanization Guide
      RNA Sequence 1

<400> SEQUENCE: 4
ggcacgaccc ugcagcggcg                                                  20

<210> SEQ ID NO 5
<211> LENGTH: 19
<212> TYPE: RNA
<213> ORGANISM: Artificial Sequence
<220> FEATURE:
<223> OTHER INFORMATION: Fragment Insertion Genetic Humanization Guide
      RNA Sequence 2

<400> SEQUENCE: 5
cgguacacga aauccucug                                                   19

```
<210> SEQ ID NO 6
<211> LENGTH: 20
<212> TYPE: RNA
<213> ORGANISM: Artificial Sequence
<220> FEATURE:
<223> OTHER INFORMATION: Fragment Deletion of SLA-DQA1 Guide RNA
      Sequence 1

<400> SEQUENCE: 6
uuaagccaua ggaggcaaca                                              20

<210> SEQ ID NO 7
<211> LENGTH: 20
<212> TYPE: RNA
<213> ORGANISM: Artificial Sequence
<220> FEATURE:
<223> OTHER INFORMATION: Fragment Deletion of SLA-DQA1 Guide RNA
      Sequence 2

<400> SEQUENCE: 7
ugaugugaac ggguaaagaa                                              20
```